US008987433B2

(12) United States Patent
Mendez et al.

(10) Patent No.: US 8,987,433 B2
(45) Date of Patent: Mar. 24, 2015

(54) VARIANT ISOPRENOID PRODUCING ENZYMES AND USES THEREOF

(75) Inventors: Michael Mendez, San Diego, CA (US);
Craig A. Behnke, San Diego, CA (US);
Nicole A. Heaps, San Diego, CA (US)

(73) Assignee: Sapphire Energy, Inc., San Diego, CA (US)

( * ) Notice: Subject to any disclaimer, the term of this patent is extended or adjusted under 35 U.S.C. 154(b) by 54 days.

(21) Appl. No.: 13/260,696

(22) PCT Filed: Mar. 29, 2010

(86) PCT No.: PCT/US2010/029071
§ 371 (c)(1),
(2), (4) Date: Dec. 5, 2011

(87) PCT Pub. No.: WO2010/111707
PCT Pub. Date: Sep. 30, 2010

(65) Prior Publication Data
US 2012/0064629 A1   Mar. 15, 2012

Related U.S. Application Data

(60) Provisional application No. 61/164,369, filed on Mar. 27, 2009.

(51) Int. Cl.
*C07H 21/04* (2006.01)
*C12P 9/00* (2006.01)
*C12N 9/10* (2006.01)
*C12N 9/88* (2006.01)

(52) U.S. Cl.
CPC .................. *C12P 9/00* (2013.01); *C12N 9/1085* (2013.01); *C12N 9/88* (2013.01)
USPC ....................................................... 536/23.2

(58) Field of Classification Search
USPC .......................................... 800/278; 536/23.2
See application file for complete search history.

(56) References Cited

U.S. PATENT DOCUMENTS

| 5,798,208 A | 8/1998 | Crea |
| 5,830,650 A | 11/1998 | Crea |
| 6,649,340 B1 | 11/2003 | Crea |
| 2005/0108791 A1* | 5/2005 | Edgerton ..................... 800/284 |
| 2008/0214406 A1 | 9/2008 | Crea |

FOREIGN PATENT DOCUMENTS

WO   WO 2010/051489 A1   5/2010

OTHER PUBLICATIONS

GenBank Accession No. AA00599 ([online], [retrieved on Jun. 4, 2013], retrieved from the internet <http://www.ncbi.nlm.nih.gov/protein/216584>).*
Zhang et al. (Two different farnesyl diphosphate synthase genes exist in the genome of the green peach aphid, *Myzus persicae*, 51 Genome, 501-510 at Figure 2 on 505 (2008).*
Szkopinska et al. (Farnesyl diphosphate synthase; regulation of product specificity, 52 Acta Biochimica Polonica No. 1, 45-55 at Figure 3 on 47 (2005).*
Lee et al., Directed evolution of *Escherichia coli* farnesyl diphosphate synthase (IspA) reveals novel structural determinants of chain length specificity, 7 Metabolic Engineering, 18-26 at Figure 3 on 24 (2005).*
Ohto et al., A thermophilic cyanobacterium Synechococcus elongates has three different Class I prenyltransferase genes, 40 Plant Molecular Biology, 307-321 at Figure 2 on p. 314 (1999).*
Ashby et al., "COQ2 is a candidate for the structural gene encoding para-Hydroxybenzoate:Polyprenyltransferease." The Journal of Biological Chemistry, 1992, vol. 267, pp. 4128-4136.
Cheng et al., "Isoprenyl diphosphate synthases: Protein sequence comparisons, a phylogenetic tree, and predictions of secondary structure." Protein Science, 1994, vol. 3, pp. 600-607.
EMBL Accession No. AF461050, Create date of Jan. 8, 2002.
EMBL Accession No. BC120218, Create date of Aug. 7, 2006.
Fu et al., "Identification of a cysteine residue essential for activity of protein farnesyltransferase." The Journal of Biological Chemistry, , 1996, vol. 271, pp. 28541-28548.
Joly et al., "Effect of site-directed mutagenesis of conserved aspartate and arginine residues upon farnesyl diphosphate sythase activity." The Journal of Biological Chemistry, 1993, vol. 268, pp. 26983-26989.
Koyama et al., "Identification of significant residues in the substrate binding site of *Bacillus stearothermphilus* farnesyl diphosphate synthase." Biochemistry, 1996, vol. 35, pp. 9533-9538.

(Continued)

*Primary Examiner* — Cynthia Collins
*Assistant Examiner* — Rebecca Coobs
(74) *Attorney, Agent, or Firm* — Sapphire Energy, Inc.

(57) ABSTRACT

This disclosure provides methods of designing and generating polypeptide variants that have altered properties compared to a parent polypeptide. The present disclosure provides methods of generating polypeptide variants, for example, variant isoprenoid synthases and/or variant prenyl transferases that have at least one desired property not present in the parent polypeptide. The present disclosure further provides polypeptides and polynucleotides encoding variant polypeptides, as well as vectors and host cells comprising the polynucleotides that encode the variant polypeptides. In other embodiments, the present disclosure provides methods of using the variant polypeptides to generate useful products, such as isoprenoid compounds and/or isoprenoid products.

4 Claims, 16 Drawing Sheets

(56) References Cited

OTHER PUBLICATIONS

Koyama et al., "Significant of PHE-220 and GLN-221 in the catalytic mechanism of farnesyl diphosphate synthase of *Bacillus stearothermophilus*." Biochemical and Biophysical Research Communications, 1995, vol. 212, pp. 681-686.

Koyama et al., "Thermostable farnesyl diphosphate synthase of *Bacillus stearothermophilus*: Molecular cloning, sequence determination, overproduction and purification.:" J. Biochem., 1993, vol. 113, pp. 355-363.

Koyama et al., Structural and functional roles of the cysteine residues of *Bacillus stearothermophilus* farnesyl diphosphate synthase. Biochemistry, 1994, vol. 33, pp. 12644-12648.

Liang et al., "Structure, mechanism and function of prenyltransferases." Eur. J. Biochem., 2002, vol. 269, pp. 3339-3354.

Marrero et al., "Effects of site-directed mutagenesis of the highly conserved aspartate residues in Domain II of farnesyl diphosphat synthase activity." The Journal of Biological Chemistry, 1992, vol. 267, pp. 21873-21878.

Park et al., "Crystal structure of protein farnesyltransferase at 2.25 angstrom resolution." Science, 1994, vol. 275, pp. 1800-1804.

Rajpal et al., "A general method for greatly improving the affinity of antibodies by using combinatorial libraries." Proc. Natl. Acad. Sci. USA, 2005, vol. 102, pp. 8466-8471.

Song et al., "Yeast farnesyl-diphosphate synthase: Site-directed mutagenesis of residues in highly conserved prenyltransferase domains I and II." Proc. Natl. Acad. Sci. USA, 1994, vol. 91, pp. 3044-3048.

Tarshis et al., "Cyrstal structure of recombinant farnesyl diphosphate sunthase at 2.6-Å resolution." Biochemistry, 1994, vol. 33, pp. 10871-10877.

Trapp et al., Genomic Organization of Plant Terpene Synthases and Molecular Evolutionary Implications. Genetics, 2001, vol. 158, pp. 811-832.

UniProt Accession No. P08836, Integrated into UniProtKB Nov. 1, 1988.

Wang et al.,"Chain-length detemination mechanism of isoprenyl diphosophate synthases and implications for molecular evolution." Trends. Biochem. Sci., 1999, vol. 24, pp. 445-451.

\* cited by examiner

| Enzyme / Organism | | III | VIII | XI | XII | XIII | XIV | (length) |
|---|---|---|---|---|---|---|---|---|
| Vetispiradiene Synthase *A. thaliana* (putative protein) | M | 84 / RK | 92 / H | 126 / H | 74 / H | 48 / DDXXD | 83 | 100 (607) |
| Casbene Synthase *R. communis* C₂₀ | M | 86 / RP | 91 / H | 125 / H | 73 / H | 47 / DDXXD | 83 | 96 (601) |
| 5-*epi*-Aristolochene *A. thaliana* (putative protein) | M | 84 / RK | 92 / H | 126 / H | 74 / H | 47 / DDXXD | 84 | 97 (604) |
| 5-*epi*-Aristolochene *N. tabacum* C₁₅ | M | 37 / RP | 88 / H | 124 / H | 73 / H | 46 / DDXXD | 82 | 98 (550) |
| Vestispiradiene Synthase *H. muticus* C₁₅ | M M | 39 / RP | 92 / H | 126 / H | 73 / H | 47 / DDXXD | 82 | 98 (555) |
| δ-Cadinene Synthase *G. arboreum* C₁₅ | M MM | 43 / RP | 87 / H | 126 / H | 73 / H | 47 / DDXXD | 83 | 97 (556) |
| δ-Cadinene Synthase *A. thaliana* (putative protein) | M | 80 / RK | 92 / H | 126 / H | 73 / H | 48 / DDXXD | 82 | 99 (600) |
| Limonene Synthase B *A. thaliana* (putative protein) | M | 49 / RR | 94 / H | 124 / H | 73 / H | 47 / DDXXD | 80 | 98 (565) |
| Limonene Synthase A1 *A. thaliana* (putative protein) | M | 39 / TT | 89 / H | 132 / H | 73 / H | 47 / DDXXD | 83 | 100 (563) |
| Limonene Synthase A2 *A. thaliana* (putative protein) | M | 78 / RR | 89 / H | 132 / H | 73 / H | 47 / DDXXD | 83 | 100 (602) |
| Limonene Synthase *M. spicata* C₁₀ | M M | 81 / RR | 92 / H | 126 / H | 73 / H | 47 / DDXXD | 83 | 97 (599) |
| Limonene Synthase *P. frutescens* C₁₀ | M MM | 84 / RR | 87 / H | 132 / H | 73 / H | 47 / DDXXD | 83 | 97 (603) |

Class III Terpene Synthase Genes

Figure 5A

| | | | | | | | | | | | |
|---|---|---|---|---|---|---|---|---|---|---|---|
| (-) Limonene Synthase<br>*A. grandis*<br>C₁₀ | M<br> | M M III<br>93<br>RR | VII VIII<br>66 39<br>H H | IX X XI<br>71 34 33<br>H | XII XIII<br>72 47<br>DDXXD | XIV<br>83 | 99 (637) | | | | |

Figure 5B (Class II Terpene Synthase Genes)

- (-) Limonene Synthase, *A. grandis*, C₁₀: M | M M III (93) | VII VIII (66 | 39) | IX X XI (71 | 34 | 33) | XII XIII (72 | 47) | XIV (83) | (99) (637); RR H H H DDXXD

- (-) Pinene Synthase, *A. grandis*, C₁₀: M | M M III (87) | VII VIII (67 | 38) | IX X XI (71 | 31 | 33) | XII XIII (72 | 47) | XIV (83) | (99) (628); RR H H H DDXXD

- δ-Selinene Synthase 2, *A. grandis*, C₁₅: M | III (34) | VII VIII (62 | 39) | IX XI (79 | 10) | XII XIII (71 | 47) | XIV (83) | (100) (525); RR H H H DDXXD DDXXD

- δ-Selinene Synthase 1, *A. grandis*, C₁₅: M | III (34) | VII VIII (64 | 39) | IX X XI (79 | 32 | 32) | XII XIII (72 | 47) | XIV (83) | (100) (581); RR H H H DDXXD DDXXD

```
chrysanthemin_synthase  ---------------------------------------------MASFISLSS
IS-45 FPPS/GPPS         --------------------------------------------------------
artemisia_FPPS          --------------------------------------------------------
Corn GGPPS              --------------------------------------------------------
Kluyveromyces FPPS      --------------------------------------------------------
saccharomyces FPPS      --------------------------------------------------------
IS-9 FPPS               ------------------------------------MHKFTGVNAKFQ
Bos FPPS                -------------------------------------EYPSNNLDLQ
Myzus FPPS              -----------------------------------MNKMLTFTRA
Myzus_bifunctional      --------------------------------------------------------
Anthonomus FPPS         MFSVKLCRNRSCRELIKNIRRGITKTSTDSNSDAISRAQDHNQMNNFNLE chrysanthemin_synthase  KSASWNASSCPHPSVQPFVTRKNVVRYHKPTSSEPSYSPLTTTLSSNLNS
IS-45 FPPS/GPPS         ----------------------------------------TTTLSSNLNS
artemisia_FPPS          -------------------------------------------MSSTDLKS
Corn GGPPS              -----------------------------------MAAGGNGAGGDTRA
Kluyveromyces FPPS      -----------------------------------------MSDN----RA
saccharomyces FPPS      ----------------------------------------MASEKEIRRE
IS-9 FPPS               QPALRN-------------------LSPVVVE-------------RERE
Bos FPPS                -PASRNRA-----------------FYSSLRVNGDQKLDA----YAQERQ
Myzus FPPS              LSRRSAFLLCDS----AVVRNNNFRAMSTVRAPPVPPVITGTAVSKDETR
Myzus_bifunctional      ----------------------------MSTVRAPPVPPVITGTAVSKDETR
Anthonomus FPPS         GPSSQYHTNVNNKRWHKQMQFNNLRALSTIQQTIPKPSHSSTLVSKEQSR chrysanthemin_synthase  QFMQVYETLKSELIHDPL-FEFDDDSRQWVERMIDYTVPGGKMVRGYSVV
IS-45 FPPS/GPPS         QFMQVYETLKSELIHDPL-FEFDDDSRQWVERMIDYTVPGGKMVRGYSVV
artemisia_FPPS          KFLKVYDTLKSELINDPA-FEFDDDSRQWIEKMLDYNVPGGKLNRGLSVV
Corn GGPPS              AFARIYKTLKEELLTDPA-FEFTEESRQWIDRMVDYNVLGGKCNRGLSVV
Kluyveromyces FPPS      QFLEVFPSLVQELRDILAGYGMPEEAIEWYEKSLNYNTPGGKLNRGLSVV
saccharomyces FPPS      RFLNVFPKLVEELNASLLAYGMPKEACDWYAHSLNYNTPGGKLNRGLSVV
IS-9 FPPS               EFVGFFPQIVRDLTEDGIGHPEVGDAVARLKEVLQYNAPGGKCNRGLTVV
Bos FPPS                DFIQHFSQIVKVLTEEDIGHPEIGDAITRLKEVLEYNAIGGKYNRGLTVV
Myzus FPPS              DFMAVFPDVVRDLTDTGR-NLDVPDVTKWLAKLLQYNVPGGKKNRGLALV
Myzus_bifunctional      DFMAVFPDVVRDLTDTGR-NLDVPDVTKWLAKLLQYNVPGGKKNRGLALV
Anthonomus FPPS         DFMALFPDLVRELTELGR-NPELPDVMRRVARVLQYNVPNGKKNRGLILI
                         *   :   *         :       . :.*.. .** ** ::

chrysanthemin_synthase  DSYQLLK---GEE-LTEEEAFLACALGWCTEWFQAFILLHDDMMDGSHTR
IS-45 FPPS/GPPS         DSYQLLK---GEE-LTEEEAFLACALGWCTEWFQAFILLHDDMMDGSHTR
artemisia_FPPS          DSYQLLK---GGE-LSDDEIFLSSALGWCIEWLQAYFLVLDDIMDESHTR
Corn GGPPS              DSYKLLK---GADALGEEETFLACTLGWCIEWLQAFFLVLDDIMDDSHTR
Kluyveromyces FPPS      DTYALLKGYKSVSELSAEEYKKVAILGWCIELLQAYFLVADOMMDQSITR
saccharomyces FPPS      DTYAILS-KKTVEQLGQEEYEKVAILGWCIELLQAYFLVADDMMDKSITR
IS-9 FPPS               AAYRELS---GPGQKDAESLRCALAVGWCIELFQAFFLVADDIMDQSLTR
Bos FPPS                ITFRELV---EPGKQDPDSLQRALTVGWCVELLQAFFLVSDDIMDSSLTR
Myzus FPPS              LSYKMLS---SPSDQTDENLKLSYILGWCVEILQAYQLVLDDIMDNAITR
Myzus_bifunctional      LSYKMLS---SPSDQTDENLKLSYILGWCVEILQAYQLVLDDIMDNAITR
Anthonomus FPPS         SAYKMLE---DPKNLTPENIKLASVLGWCLEMIHSCFLVLDDIMDNSETR
                        ::  *           :,      .*** *  ::  *: **.** . **
```

Figure 6 (CONT'D)

```
chrysanthemin_synthase   RGQPCWFRLPEVGAVAINDGVLLRNHVHRILKKHFQGKAYYVHLVDLFNE
IS-45 FPPS/GPPS          RGQPCWFRLPEVGAVAINDGVLLRNHVHRILKKHFQGKAYYVHLVDLFNE
artemisia_FPPS           RGQPCWFRLPKVGMIAANDGILLRNHVPRILKKHFRGKPYYVDLVDLFNE
Corn GGPPS               RGQPCWFRVPQVGLIAANDGIILRNHISRILRRHFKGKPYYADLLDLFNE
Kluyveromyces FPPS       RGQPCWYKVENVGDIAINDAFMLEGAIYCLLKKHFRTEPYYVDLLELFHD
saccharomyces FPPS       RGQPCWYKVPEVGEIAINDAFMLEAAIYKLLKSHFRNEKYYIDITELFHE
IS-9 FPPS                RGQLCWYKKEGVGLDAINDSFLLESSVYRVLKKYCRQRPYYVHLLELFLQ
Bos FPPS                 RGQTCWYQKPGIGLDAINDAFLLESSIYRLLKLYCREQPYYLDLIELFLQ
Myzus FPPS               RGRPCWYRHNDIGLMAVNDGVLLEQAIYQLIKKYFKDKPYYTHILELFFD
Myzus_bifunctional       RGRPCWYRHNDIGLMAVNDGVLLEQAIYQLIKKYFKDKPYYTHILELFFD
Anthonomus FPPS          RGSLCWYRQNGIGLSAINDGLILENAVYTLLKMHLRDHPAYVPIIELFHE
                         **  **::    :*   *  **..:*.  :   ::  :  :  .  * : :**  :

chrysanthemin_synthase   TEFQTISGQMIDTISRLA-GQKELSKYSMSLNRRIVQYKGAYYSCYLPIA
IS-45 FPPS/GPPS          TEFQTISGQMIDLITTLV-GEKDLSKYSLSIHRRIVQYKTAYYSFYLPVA
artemisia_FPPS           VEFQTASGQMIDLITTLV-GEKDLSKYSLSIHRRIVQYKTAYYSFYLPVA
Corn GGPPS               VEFKTASGQLLDLITTHE-GEKDLTKYNITVHGRIVQYKTAYYSFYLPVA
Kluyveromyces FPPS       VTFQTELGQLLDLITAPE-DKVDLSKFSLEKHSFIVIFKTAYYSFYLAVA
saccharomyces FPPS       VTFQTELGQLMDLITAPE-DKVDLSKFSLKKHSFIVTFKTAYYSFYLPVA
IS-9 FPPS                TAYQTELGQMLDLITAPV-SKVDLSHFSEERYKAIVKYKTAFYSFYLPVA
Bos FPPS                 SSYQTEIGQTLDLITAPQ-GNVDLGRFTEKRYKSIVKYKTAFYSFYLPVA
Myzus FPPS               VTMKTAMGQCLDMLTANSFKSKKLEKYTMENYTAIVKYKTAYYSFFLPVC
Myzus_bifunctional       VTMKTAMGQCLDMLTANSFKSKKLEKYTMENYTAIVKYKTAYYSFFLPVC
Anthonomus FPPS          TVSKTTLGQCLDSMCLDSDGKPKLEMFSMSRYTSIVKYKTAYYSFHMPVA
                         :*  **  :*  :       .*   :         **  :*  *:**  ....:

chrysanthemin_synthase   CALLMFGE-NLDDYVQVKDILVELGMYYQIQNDYLDTFGDPNVFGKTGTD
IS-45 FPPS/GPPS          CALLMFGE-DLDKHVEVKNVLVEMGTYFQVQDDYLDCFGAPEVIGKIGTD
artemisia_FPPS           CALLMFGE-DLDKHVEVKNVLVEMGTYFQVQDDYLDCFGAPEVIGKIGTD
Corn GGPPS               CALLLSGE-NLDNYGDVENILVEMGTYFQVQDDYLDCYGDPEFIGKIGTD
Kluyveromyces FPPS       LAMFAAGITDSKDLKQASDVLIPLGEYFQIQDDFLDCFGKPEDIGKIGTD
saccharomyces FPPS       LAMYVAGITDEKDLKQARDVLIPLGEYFQIQDDYLDCFGTPEQIGKIGTD
IS-9 FPPS                AAMYMVGIDSKEEHENAKAILLEMGEYFQIQDDYLDCFGDPALTGKVGTD
Bos FPPS                 AAMYMAGIDGEKEHAHAKKILLEMGEFFQIQDDYLDLFGDPSMTGKIGTD
Myzus FPPS               LAMRMTNINDPEIFRQAKTILLEMGHFFQVQDDFLDCYGDPDVMGKIGTD
Myzus_bifunctional       LAMRMTNINDPEIFRQAKTILLEMGHFFQVQDDFLDCYGDPDVMGKIGTD
Anthonomus FPPS          VAMYLAGMNDPEQHRQAKTILLEMGEFFQIQDDFLDCFGDPAVTGKKGTD
                         *:    .   .    . ..   :*: :* ::*:*:*.**   :*  *    * chrysanthemin_synthase   IEECKCSWLIAKALELANEEQKKILSENYGIKDPAKVAKVKEIYHALNLK
IS-45 FPPS/GPPS          IEDFKCSWLVVKALELANEEQKKTLHENYGKKDPASVAKVKEVYHTLNLQ
artemisia_FPPS           IEDFKCSWLVVKALELPNEEQKKTLHENYGKKDPASVAKVKEVYHTLNLQ
Corn GGPPS               IEDYKCSWLVVQALERADESQKRILFENYGKKDPACVAKVKNLYKELDLE
Kluyveromyces FPPS       IQDNKCSWVINVALKNATKEQRDILDENYGRKDSEKEQKCRAVFNELNIQ
saccharomyces FPPS       IQDNKCSWVINKALELASAEQRKTLDENYGKKDSVAEAKCKKIFNDLKIE
IS-9 FPPS                IQDNKCSWLVVQCLQRVTPEQRQLLEDNYGRKEPEKVAKVKELYEAVGMR
Bos FPPS                 IQDNKCSWLVVQCLQRASPEQRQILQENYGQKEAEKVARVKALYEEMNLS
Myzus FPPS               IEDGKCSWLAVVALQKVNSEQKKIMEDNYGIDDPANVAIIKDLYAQLKLA
Myzus_bifunctional       IEDGKCSWLAVVALQKVNSEQKKIMEDNYGIDDPANVAIIKDLYAQLKLA
Anthonomus FPPS          IQEGKCSWLAVVALQRASAAQRKIMEEHYGVDDPNSVAIIKKLYEDLSLP
                         *::.****:   .*:   *:        * : ::**  ..       :  ::  : :

chrysanthemin_synthase   GAYEDYETNLYENSMKAIKAHP-SIAVQA-VLKSCLEKMYKGHK-
```

Figure 6 (CONT'D)

```
IS-45 FPPS/GPPS      AVFEDYEATSYKKLITSIENHP-SKAVQA-VLKSFLGKIYKRQKG
artemisia_FPPS       AVFEDYEATSYKKLITSIENHP-SKAVQA-VLKSFLGKIYKRQK-
Corn GGPPS           AVFQEYENESYKKLIADIEAQP-SIAVQK-VLKSFLHKIYKRQK-
Kluyveromyces FPPS   DIYHKYEEETASNLREKIANIDESRGFKAEVLTLFLNKIYHRKK-
saccharomyces FPPS   QLYHEYEESIAKDLKAKISQVDESRGFKADVLTAFLNKVYKRSK-
IS-9 FPPS            AAFQQYEESSYRRLQELIEKHS--NRLPKEIFLGLAQKIYKRQK-
Bos FPPS             AVYMQYEEDSYNHIMGLIEQYA--APLPPAIFLGLAQKIYKRKK-
Myzus FPPS           DTFHLYEEESYKLICTHIQQLS--RGLSQDMFFKFLEKIYKRTL-
Myzus_bifunctional   DTFHFYEEESYKLICTHIQQLS--RGLSQDMFFKFLEKIYKRTL-
Anthonomus FPPS      NTYAIYEEESYNIIKTHIQQIS--KGLRHDLFFSIMEKLYKREC-
                       :  **         *       .   ::    *:*:
```

TABLE 1

Conifer and other selected terpene synthases

| Products | Terpene synthase name | | | | Genbank accession no. | | Reference | | Region on chromosome |
|---|---|---|---|---|---|---|---|---|---|
| | Species | Former gene | Enzyme | cDNA/genomic | cDNA | gDNA | cDNA | gDNA | |
| Abietadiene | A. grandis | ag22 | AggABI | Agggabi | U50768 | AF326616 | STOFER VOGEL et al (1996) | Trapp and Croteau* | — |
| (−)-α-isaboleae | A. grandis | ag1 | AgrαBIS | AgrαBIS | AF006195 | AF326515 | BOHLMANN et al (1998a) | Trapp and Croteau* | — |
| γ-Camphene | A. grandis | ag6 | Agg-CAM | Agg-cam | U87910 | — | BOHLMANN et al (1999) | — | — |
| γ-humdene | A. grandis | ag5 | Agr γ1um | Agr γ1um | U92267 | — | STEELE et al. (1998) | — | — |
| (−)-Limonene | A. grandis | ag10 | Agg-LIM1 | Agg-LIM1 | AF006193 | AF326618 | BOHLMANN et al (1997) | Trapp and Croteau* | — |
| Myrcene | A. grandis | ag2 | AggMYR | AggMYR | U87908 | — | BOHLMANN et al (1997) | — | — |
| (−)-α/β-Pinene | A. grandis | ag3 | Agg-PIN1 | Agg-pin1 | U87909 | AF326517 | BOHLMANN et al (1997) | Trapp and Croteau* | — |
| (−)-α-Pinene/(−)-limonene | A. grandis | ag11 | Agg-PIN2 | Agg-pin2 | AF189207 | — | BOHLMANN et al (1999) | — | — |
| (−)-β-Phellandrene | A. grandis | ag8 | Agg-βPHE | Agg-βphe | AF189205 | AF326513 | BOHLMANN et al (1999) | Trapp and Croteau* | — |
| δ-Selinene | A. grandis | ag4 | Ag?SEL1 Ag?SEL2 | Ag?sel1 Ag?sel2 | U92266 | AF326514 AF326619 | STEELE et al (1998) | Trapp and Croteau* | — |
| Taxadiene | T. brevifolia | Tb1 | TbggTAX | Tbggtax | U48796 | — | WIRBUNG and CARTHEAD (1996) | Trapp and Croteau* | — |
| Terpinolene | A. grandis | ag9 | AggTEO | Aggteo | AF139206 | L04680 | BOHLMANN et al (1999) | — | — |
| 5-epi-Aristolachene | nicotiana | TEAS3 | NtcARIS | Ntcaris | L04680 | L04680 | FACCHINI and CHAPPELL (1992) | FACCHINI and CHAPPELL (1992) | — |
| | A. thaliana | TEAS4 | NtcARI4 | Nttcari4 | L04680 | L04680 | — | — | — |
| 5-epi-Aristolachene | A. thaliana | — | AtcAR1 | Atcari | — | AL022224 | — | Bevan et al? | Chromosome 4 BAC F1C12 (ESSA) nt 44054-38820 |
| δ-Cadinene | G? | CAD1-A | GAFδCAD1A | Gafδcad1a | X96429 | Y18484 | CHEN et al. (1996) | Liang et al? | — |
| δ-Cadinene | G? | CAD1-A | GHfδCAD1 | Ghf δcad1 | U88318 | — | DAVIS et al (1998) | Chen et al? | — |
| δ-Cadinene | G? | gCAD1-B | GafδCAD1B | Gafδcad1b | — | X95323 | — | Bevan et al? | Chromosome 4 BAC F1C12 (ESSA) nt 44054-58820 |
| -Cadinene? | A. thaliana | — | AtCAD | Atcad | — | AL022224 | — | | |
| Carbene | Ricinus cumm? | cas | RcgCAS | Rcggcas | L32134 | NA | MAU and WEST (1994) | Wes? | Chromosome 4 (Top) BAC |
| (−)-Copalyl diphosphate? | A. thaliana | GA. | Atgg-COPP1 | Atgg-coppl | U11034 | NA | SUN and KAMIYA (1994) | Sun et al. (1992) | Taj8 nt 34971-41856 |
| (−)-Kaurene? | A. thaliana | GA2 | Argg-KAU | Argg-kau | AF034774 | AC00404? AC007202 | YAMAGUCHI et al. (1996) | Bashide et al? Vysotssain et al? | Chromosome 1 BAC T3K14 nt 43552-47420 |
| (−)-Limonene | Perilla? | PFLC1 | Pfg-LIM1 | Pfg-lim1 | D49368 | AB005744 | YUSA et al. (1996) | Tsubouch? | — |
| (−)-Limonene | Mentha spicata | LMS | Msg-LIM | Msg-lim | L13459 | — | COLAY et al. 91998) | — | — |
| (−)-Limonene? | M. Lungifolia | LMS | Mfg-LIM | Mfg-lim | AF175323 | — | Crock and Crotea? | — | — |
| Limonene? | A. thaliana | — | AtlIMA1 | Atllima1 | — | Z97341 | — | Jones and Davis? | Chromosome 4 CF6 (ESSA 1) nt 164983-170505 |
| | A. thaliana | — | AtlIMA2 | Atllima2 | — | — | — | Bevan et al? | — |
| Limonene? | A. thaliana | — | AtlImb | Atllimb | — | Z97341 | — | Bevan et al? | Chromosome 4 CF5 (ESSA 1) nt 172598-175344 |
| (S)-Linalool | Clarkia romainna | LIS | CcglINOH | Ccglinoh | — | AF067662 | CSEKE et al (1996) | Cacke et al 91998) | — |

Figure 11A

TABLE 1

Conifer and other selected terpene synthases

| | | Terpene synthase name | | | Genbank accession no. | | Reference | | |
|---|---|---|---|---|---|---|---|---|---|
| Products | Species | Former gene | Enzyme② | cDNA/genomic② | cDNA | gDNA | cDNA | gDNA | Region on chromosome |
| Linalool② | A. thaliana | — | AtgINOH | Atglinoh | — | AC02294 | | Fedespie② | Chromosome 1 BAC FHP17 nt 73996-78905 |
| Vetispiradiene | Hyoscyacous② | Chimera | HmfVET | Hmfvet | U20187 | NA | BACK and CHAPPELL (1995) | Chappell② | — |
| Vetispiradiene② | A. thaliana | — | AtVET | Atvet | — | AL022224 | — | Bevan et al ② | Chromosome 4 BAC F12C12 (ESSA) nt 54692-56893 | tc, genomic sequences by Trapp and Crotean (accession nos. pending);
NA, sequences anavailable in the public databases but not disclosed in journal reference;
pc, sequences obtained by personal communications;
ds, sequences in public database by direct submission but not published;
p, sequences in database with putative function;
c, confirmed gene by experimental determination stated in database;
i, two possible isozymes reported for the same region referred to as A1 and A2;
—, no former gene name or accession number.
Species names are: *Abies grandis, Arabidopsis thaliana, Clarkia concinna, Gossypium arboreum, Hyoscyamus muticus, Mentha longifolia, Mentha spicata, Nicotiana tabacum, Ricinus communis, Perilla frutescens, Taxus brevifolia, Zea m*.

②Former names, respectively, for (-)-copalyl diphosphate synthase and ent-kaurene synthase were ent-kaurene synthase A (KSA) and ent-kaurene synthase B (KSB), and mutant phenotypes were ga1 and ga2; these designations have been used loosely.
②Nomenclature architecture is specified as follows. The Latin binomial two-letter abbreviations are in spaces 1 and 2. The substrates (1-to 4-letter abbrev.) are in spaces 3-6, consisting of 1- or 2-letter abbrev, for substrate utilized in boldface (e.g., g, geranyl diphosphate; f, farnesyl diphosphate; gg, geranylgeranyl diphosphate; c, copalyl diphosphate; ch, chrysanthemyl diphosphate; in lowercase) followed by stereochemistry and/or isomer definition (e.g., α, β, δ, γ, etc. followed by epi (e), E, Z, -, +, etc.).
The 3-letter product abbrev, indicates the major product is an olefin; otherwise the quenching nucleophile is indicated, (e.g., ABI, abietadiene synthase; BORPP, bornyl diphosphate synthase; CEDOH, cedrol synthase);
Uppercase specifies protein and lowercase specifies cDNA or gDNA.
All letters except species names are in italics for cDNA and gene.
Distinction between cDNA and gDNA must be stated or a g is added before the abbreviation, e.g., Tbggtax cDNA and gTbggtax or Tbggtax gene (nomenclature) system devised by S. Trapp, E. Davis, J. Crock, and R. Croteau).
②indicates text missing or illegible when filed

Figure 11B

VARIANT ISOPRENOID PRODUCING ENZYMES AND USES THEREOF

CROSS REFERENCE TO RELATED APPLICATION

This application is a national phase under 35 U.S. §371 of International Application Number PCT/US2010/029071, filed Mar. 29, 2010 which claims the benefit of U.S. Provisional Application No, 61/164,369, filed Mar. 27, 2009, the entire contents of both applications are incorporated by reference for all purposes.

INCORPORATION BY REFERENCE

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

BACKGROUND

Isoprenoids are a family of compounds derived from an isoprene building block. Isoprenoids include primary metabolites such as sterols, carotenoids, growth regulators, and the polyprenol substituents of dolichols, quinones, and proteins. These compounds are essential for membrane integrity, photoprotection, orchestration of developmental programs, and anchoring essential biochemical functions to specific membrane systems, respectively. Isoprenoids also include secondary metabolites such as monoterpenes, sesquiterpenes, and diterpenes.

Isoprenoids are made via the isoprenoid biosynthetic pathway. The common denominator for this diverse array of compounds is a universal five-carbon building block, isoprene. The polymerization of two diphosphorylated isoprene building blocks (e.g., isopentenyl pyrophosphate (IPP) and dimethylallyl diphosphate (DMAPP)) generates geranyl diphosphate (GPP), a linear $C_{10}$ intermediate that can be converted to cyclic or linear end-products representing the monoterpenes, or used in another round of polymerization. The addition of a third isoprene unit to GPP generates which can also be converted to cyclic or linear products representing the sesquiterpene class. Continuing the polymerization and chemical differentiation cycle leads to the production of other classes of terpenoids named according to the number of isoprene building blocks leading to their biosynthesis, for example, the addition of a third IPP to FPP generates geranylgeranyl diphosphate (GGPP).

These polymerization reactions are catalyzed by prenyl transferases that direct the attack of a carbocation (an electron deficient carbon atom resulting from the loss of the diphosphate moiety of one substrate) to an electron-rich carbon atom of the double bond on the IPP molecule. The enzymes responsible for the cyclization of GPP, FPP, and GGPP are referred to as monoterpene, sesquiterpene, and diterpene synthases or collectively, terpene synthases, and represent reactions committing carbon from the general isoprenoid pathway to end products in the monoterpene, sesquiterpene, and diterpene classes, respectively.

An important biochemical distinction between the prenyl transferase and isoprenoid synthase reactions are that the prenyl transferases catalyze carbon-carbon bond formation between two substrate molecules, whereas the synthases catalyze an intramolecular carbon-carbon bond formation.

Increasing the activity of a prenyl transferase and/or an isoprenoid synthase in a cell can increase the terpene and/or terpenoid content of the cell. In addition, if a cell contains a terpene and/or terpenoid that mediates a desirable phenotype (for instance, a biocidal compound that confers a crop protection phenotype), increasing the activity of the appropriate prenyl transferase and/or isoprenoid synthase may increase accumulation of the compound in the cell.

Described herein are modified prenyl transferase and isoprenoid synthase enzymes useful in the production of terpenes and terpenoids. Also described herein are methods for the production of terpenes and terpenoids.

SUMMARY

The native amino acid sequence of *Gallus gallus* farnesyl diphosphate synthase (FPP) synthase (SEQ ID NO: 1) was codon-optimized for the nuclear genome of *Chlamydomonas* sp. (SEQ ID NO: 21). Individual mutants were identified, Thr269Tyr, Thr269Asp, and Thr269Gln (according to the numbering of SEQ ID NO:1) that all had increased prenyl transferase activity as compared to the wild type protein. Described herein is an isolated polynucleotide encoding *Gallus gallus* farnesyl diphosphate synthase (FPP) synthase capable of being used to transform a photosynthetic bacterium, yeast, alga, or vascular plant, wherein the polynucleotide comprises (a) nucleic acid sequence SEQ ID NO: 21, wherein nucleotides 802, 803, and 804 of SEQ ID NO: 21 encode for Tyrosine, Aspartic Acid, or Glutamine, or (b) a nucleic acid sequence with at least 95%, at least 98%, or at least 99% sequence identity to the nucleic acid sequence of SEQ ID NO: 21 wherein nucleotides 802, 803, and 804 of SEQ ID NO: 21 are present in the nucleic acid sequence and encode for Tyrosine, Aspartic Acid, or Glutamine. A bacterial, yeast, alga, or vascular plant cell transformed with the isolated polynucleotide is also described.

One of the several embodiments disclosed herein is an isolated polynucleotide comprising the nucleotide sequence of SEQ ID NO: 21. wherein nucleotides 802, 803 and 804 of SEQ ID NO. 21 encode a Tyrosine, an Aspartic Acid or a Glutamine. In one particular embodiment, the nucleotides 802, 803 and 804 of SEQ ID NO 21 encode Tyrosine, in another particular embodiment, the nucleotides 802, 803 and 804 of SEQ ID NO. 21 encode Aspartic Acid. In yet another particular embodiment, the nucleotides 802, 803 and 804 of SEQ ID NO. 21 encode Glutamine.

One embodiment of the disclosure is a polypeptide comprising a variant prenyl transferase having at least one desired property not present in the parent prenyl transferase. In one embodiment, the polypeptide has at least 90% homology with an amino acid sequence of FIG. 11 or FIG. 6. In another embodiment, the prenyl transferase is FPP synthase, FPP/GPP synthase, or IPP synthase. In another embodiment, the polypeptide contains a mutation in a region corresponding to residues 97-137, 175-198 or 250-290 of *Gallus gallus* FPP synthase. In another embodiment, the desired property is prenyl synthase enzyme activity that is at least 1.5 times the enzyme activity of the parent polypeptide; increased enzyme flux that is at least 10% greater than the wild-type polypeptide, as measured by GC/MS, thin layer chromatography, or by: (i) tagging the variant prenyl synthase with a tag that allows for removal of the variant polypeptide from a reaction mixture; (ii) reacting variant polypeptide in a prenyl transferase reaction; (iii) isolating pyrophosphate from the reaction mixture; and (iv) quantitating amount of pyrophosphate, where an increase in pyrophosphate compared to the amount of pyrophosphate generated by a parent polypeptide over a period of time indicates an increased enzyme flux; an altered product profile, wherein the altered product profile produces a greater amount of a polyisoprenoid compound than a parent polypeptide; decreased Km value for a substrate; increased affinity for a ligand; performs a novel activity, wherein the novel activity is production of a polyisoprenoid not normally produced by the wild-type polypeptide; retains more than about 80% of the initial prenyl transferase activity after 20 minutes of incubation at 50° C. and pH 7; or increased polypeptide solubility.

Another embodiment of the disclosure is a polypeptide comprising a variant isoprenoid synthase having at least one desired property not present in the parent isoprenoid synthase, wherein the desired property is: isoprenoid synthase enzyme activity that is at least 1.5 times the enzyme activity of the parent polypeptide; increased enzyme flux that is at least 10% greater than the wild-type polypeptide, as measured by GC/MS, thin layer chromatography, or by: (i) tagging the variant isoprenoid synthase with a tag that allows for removal of the variant isoprenoid synthase from a reaction mixture; (ii) reacting variant isoprenoid synthase in a isoprenoid synthase reaction; (iii) isolating pyrophosphate from the reaction mixture; and (iv) quantitating amount of pyrophosphate, where an increase in pyrophosphate compared to the amount of pyrophosphate generated by a parent isoprenoid synthase over a period of time indicates an increased enzyme flux; an altered product profile, wherein the altered product profile produces a greater amount of a polyisoprenoid compound than a parent polypeptide; decreased Km value for a substrate by at least 5%; increased affinity for a ligand by at least 5%; performs a novel activity, wherein the novel activity is production of a polyisoprenoid not normally produced by the wild-type polypeptide; retains more than about 80% of the initial isoprenoid synthase activity after 20 minutes of incubation at 50° C. and pH 7; or increased polypeptide solubility.

Yet another embodiment of the disclosure is a method of producing a long chain isoprenyl pyrophosphate compound comprising contacting a variant prenyl transferase with multiple isoprenoid precursor compounds under conditions such that a long chain isoprenyl pyrophosphate compound is produced.

Another embodiment of the disclosure is a method of cyclizing an isoprenoid compound comprising contacting a variant isoprenoid synthase with an isoprenoid under conditions such that the isoprenoid is cyclized.

Yet another embodiment of the disclosure is an assay for measuring enzyme flux comprising: (i) tagging the variant polypeptide with a tag that allows for removal of the variant polypeptide from a reaction mixture; (ii) reacting variant polypeptide in a isoprenoid producing reaction; (iii) isolating pyrophosphate from the reaction mixture; and (iv) quantitating amount of pyrophosphate, where an increase in pyrophosphate compared to the amount of pyrophosphate generated by a parent polypeptide over a period of time indicates an increased enzyme flux.

Another embodiment of the disclosure is a method of producing an isoprenoid producing enzyme having at least one desired property, comprising the steps of: (a) subjecting a starting or parental polynucleotide set to a mutagenesis process so as to produce a progeny polynucleotide set, wherein the mutagenesis process of step (a) comprises a saturation mutagenesis process for generating from a codon-containing parental polypeptide template a progeny polypeptide set in which a full range of single amino acid substitutions is represented at each amino acid position, comprising the steps of: subjecting a working codon-containing template polynucleotide to polymerase-based amplification using a degenerate oligonucleotide for each codon to be mutagenized, wherein each of the degenerate oligonucleotides is comprised of a first homologous sequence and a degenerate triplet sequence, so as to generate a set of progeny polynucleotides; and subjecting the set of progeny polynucleotides to recombinant expression so as to produce polypeptides encoded by the progeny polynucleotides; and (b) subjecting the progeny polynucleotide set to an end selection-based screening and enrichment process, so as to select for a desirable subset of the progeny polynucleotide set which produces a polypeptide having at least one desirable property.

Another embodiment of the disclosure is a method of producing an isoprenoid producing enzyme having at least one desired property, comprising the steps of: a) obtaining an initial population of organisms, b) generating a set of mutagenized organisms, from the initial population, wherein non-stochastic genetic mutations are represented in the set of mutagenized organisms, and c) identifying the desirable trait exhibited by one of the set of mutagenized organisms, thereby producing a variant isoprenoid producing enzyme.

Yet another embodiment of the disclosure is a method of producing an isoprenoid producing enzyme having at least one desired property, comprising the steps of: (a) blocking or interrupting a polynucleotide synthesis or amplification process of an isoprenoid producing enzyme with at least one member selected from the group consisting of UV light, one or more DNA adducts, DNA intercalating agents, and/or polymerase inhibitors or poisons, wherein the member blocks or interrupts polynucleotide synthesis or amplification, thereby providing a plurality of polynucleotides at various stages of synthesis; (b) denaturing the plurality of polynucleotides obtained from step (a) to produce a mixture of single-stranded polynucleotides; (c) incubating the mixture of single stranded polynucleotides with a polymerase under conditions which result in annealing of the single stranded polynucleotides at regions of identity between the single-stranded polynucleotides and which results in the synthesis of at least one mutagenized double stranded polynucleotide; (d) repeating steps (b) and (c); (e) generating at least one mutagenized double stranded polynucleotide that encodes a polypeptide; and (f) screening the at least one mutagenized polynucleotide that encodes an isoprenoid producing enzyme to determine the polypeptide that possesses an activity of interest, thereby producing a variant isoprenoid producing enzyme.

Another embodiment of the disclosure is a method of producing an isoprenoid producing enzyme having at least one desired property, comprising the steps of: (a) providing a population of homologous polynucleotides that code for isoprenoid producing enzymes, wherein at least two of the related polynucleotides differ from each other by the presence of at least one deletion or insertion; (b) shuffling the homologous polynucleotides to produce a plurality of recombinant polynucleotides, and selecting or screening the population of recombinant polynucleotides to obtain at least one recombinant polynucleotide that has evolved toward the desired functional property; and, (c) shuffling the recombinant polynucleotide(s) produced in the previous step, and selecting or screening for at least one recombinant polynucleotide that has evolved toward the desired functional property, thereby producing a variant isoprenoid producing enzyme.

Yet another embodiment of the disclosure is a method of producing an isoprenoid producing enzyme having at least one desired property, wherein the method is a method for forming a mutagenized double-stranded polynucleotide from a template double-stranded polynucleotide, wherein the template double-stranded polynucleotide has been cleaved into double-stranded-random fragments of a desired size, comprising the steps of a) providing a double stranded polynucleotide that codes for an isoprenoid producing enzyme; b) cleaving the double stranded polynucleotide into a population of double-stranded random fragments; c) adding to the resultant population of double-stranded random fragments one or more single or double-stranded oligonucleotide, wherein the oligonucleotides comprise an area of identity and an area of heterology to the double-stranded template polynucleotide; d) denaturing the resultant mixture of double-stranded random fragments and oligonucleotides into single-stranded fragments; e) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other thereby forming a mutagenized double-stranded polynucleotide; and f) repeating steps c) and d) for at least two further cycles, wherein the resultant mixture in step (d) of a further cycle includes the mutagenized double-stranded polynucleotide from step e) of the previous cycle, and the further cycle forms a further mutagenized double-stranded polynucleotide, thereby producing a variant isoprenoid producing enzyme.

Another embodiment of the disclosure is a method of producing an isoprenoid producing enzyme having at least one desired property, comprising the steps of: conducting a polynucleotide amplification process on overlapping segments of a population of isoprenoid producing enzyme polynucleotides under conditions whereby one segment serves as a template for extension of another segment, to generate a population of recombinant polynucleotides; and selecting or screening a recombinant polynucleotide for a desired property, wherein the amplification process is performed in the presence of an agent that promotes annealing of the overlapping segments, thereby producing a variant isoprenoid producing enzyme.

Yet another embodiment of the disclosure is a method of producing an isoprenoid producing enzyme having at least one desired property, comprising the steps of: (a) blocking or interrupting a polynucleotide synthesis or amplification process of an isoprenoid producing enzyme with at least one member selected from the group consisting of UV light, one or more DNA adducts, DNA intercalating agents, and/or polymerase inhibitors or poisons, wherein the member blocks or interrupts polynucleotide synthesis or amplification, thereby providing a plurality of polynucleotides at various stages of synthesis; (b) denaturing the plurality of polynucleotides obtained from step (a) to produce a mixture of single-stranded polynucleotides; (c) incubating the mixture of single stranded polynucleotides with a polymerase under conditions which result in annealing of the single stranded polynucleotides at regions of identity between the single-stranded polynucleotides and which results in the synthesis of at least one mutagenized double stranded polynucleotide; (d) repeating steps (b) and (c); (e) generating at least one mutagenized double stranded polynucleotide that encodes a polypeptide; and (f) screening the at least one mutagenized polynucleotide that encodes an isoprenoid producing enzyme to determine the polypeptide that possesses an activity of interest, thereby producing a variant isoprenoid producing enzyme.

Another embodiment of the disclosure is a method of producing an isoprenoid producing enzyme having at least one desired property, comprising the steps of: (a) providing a population of homologous polynucleotides that code for isoprenoid producing enzymes, wherein at least two of the related polynucleotides differ from each other by the presence of at least one deletion or insertion; (b) shuffling the homologous polynucleotides to produce a plurality of recombinant polynucleotides, and selecting or screening the population of recombinant polynucleotides to obtain at least one recombinant polynucleotide that has evolved toward the desired functional property; and, (c) shuffling the recombinant polynucleotide(s) produced in the previous step, and selecting or screening for at least one recombinant polynucleotide that has evolved toward the desired functional property, thereby producing a variant isoprenoid producing enzyme.

Yet another embodiment of the disclosure is a method of producing an isoprenoid producing enzyme having at least one desired property, wherein the method is a method for forming a mutagenized double-stranded polynucleotide from a template double-stranded polynucleotide, wherein the template double-stranded polynucleotide has been cleaved into double-stranded-random fragments of a desired size, comprising the steps of: a) providing a double stranded polynucleotide that codes for an isoprenoid producing enzyme; b) cleaving the double stranded polynucleotide into a population of double-stranded random fragments; c) adding to the resultant population of double-stranded random fragments one or more single or double-stranded oligonucleotide, wherein the oligonucleotides comprise an area of identity and an area of heterology to the double-stranded template polynucleotide; d) denaturing the resultant mixture of double-stranded random fragments and oligonucleotides into single-stranded fragments; e) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other thereby forming a mutagenized double-stranded polynucleotide; and f) repeating steps c) and d) for at least two further cycles, wherein the resultant mixture in step (d) of a further cycle includes the mutagenized double-stranded polynucleotide from step e) of the previous cycle, and the further cycle forms a further mutagenized double-stranded polynucleotide, thereby producing a variant isoprenoid producing enzyme.

Another embodiment of the disclosure is a method of producing an isoprenoid producing enzyme having at least one desired property, comprising the steps of: conducting a polynucleotide amplification process on overlapping segments of a population of isoprenoid producing enzyme polynucleotides under conditions whereby one segment serves as a template for extension of another segment, to generate a population of recombinant polynucleotides; and selecting or screening a recombinant polynucleotide for a desired property, wherein the amplification process is performed in the presence of an agent that promotes annealing of the overlapping segments, thereby producing a variant isoprenoid producing enzyme.

Yet another embodiment of the disclosure is a method of producing an isoprenoid producing enzyme having at least one desired property, comprising the steps of: a) selecting one or more defined region(s) of the amino acid sequence of the isoprenoid producing enzyme encoded by the gene to be mutagenized; b) for each of the defined region(s), determining one or more amino acid residue(s) to be inserted into amino acid positions in the defined region; c) synthesizing without saturation a mixture of oligonucleotides, comprising a nucleotide sequence for each defined region, wherein each oligonucleotide contains, at each sequence position in the defined region, either a nucleotide required for synthesis of the protein to be mutagenized or a nucleotide required for a codon of one of the predetermined amino acid(s), the mixture containing all possible variant oligonucleotides according to this criterion; and d) generating an expression library of cloned genes containing the oligonucleotides, thereby producing a variant isoprenoid producing enzyme.

Another embodiment of the disclosure is a method of producing an isoprenoid producing enzyme having at least one desired property, wherein a predetermined amino acid appears at one or more functional amino acid positions in a defined region of the polypeptide, comprising the steps of: selecting one or more functional amino acid positions in a defined region of the amino acid sequence of the isoprenoid producing enzyme; determining an amino acid residue to be substituted at each functional amino acid position within the defined region; synthesizing individual polynucleotides encoding the defined region, the polynucleotides collectively representing possible variant polynucleotides according to the following criteria: i) each polynucleotide containing at each functional amino acid codon position in the defined region, either a codon required for the amino acid residue of the polypeptide or a codon for the predetermined amino acid residue, and ii) each polynucleotide containing no more than one codon for the predetermined amino acid residue, thereby generating a library of polynucleotides in which the predetermined amino acid residue appears at each functional amino acid position within the defined region, thereby producing a variant isoprenoid producing enzyme.

Yet another embodiment of the disclosure is a method of altering a polynucleotide encoding an isoprenoid producing enzyme having a desired property, comprising: providing a population of variants of a polynucleotide encoding at least a portion of an isoprenoid producing enzyme, at least one of which is in cell-free form; rearranging the variants of the polynucleotide to form recombinant polynucleotides; transforming a host cell with the selected recombinant polynucleotides; and selecting transformants expressing the enzyme which has a desired property.

In other embodiments of the disclosure, the methods described are used wherein the isoprenoid producing enzyme is an isoprenoid synthase enzyme, wherein the isoprenoid producing enzyme is a prenyl transferase enzyme; wherein the prenyl transferase enzyme is FPP synthase, GPP synthase, a GGPP synthase, or a chimeric or fusion synthase (for example, a GPP/FPP synthase); wherein the mutagenesis process targets at least one pre-selected portion of the polynucleotide, and wherein the enzyme is FPP from *Gallus gallus* and the pre-selected portion comprises amino acid residues 97-137, residues 175-198, residues 250-290, or a combination thereof, wherein the desired property is increased enzyme activity, increased enzyme flux, altered product profile, reduced Km for substrate, increased ligand affinity, performs a novel activity, increased enzyme stability or increased solubility; or wherein the novel activity is the production of an isoprenoid not normally produced by the enzyme.

Another embodiment of the disclosure is a method of producing an isoprenoid producing enzyme having at least one desired property, comprising the steps of: subjecting a polynucleotide encoding an isoprenoid producing enzyme to a mutagenesis process so as to produce a progeny polynucleotide set; selecting a subset of the progeny polynucleotide set, wherein the subset comprises polynucleotides encoding isoprenoid producing enzymes having a desired property; and transforming a host cell with at least one polynucleotide of the subset, thereby producing the isoprenoid producing enzyme.

Yet another embodiment of the disclosure is a combinatorial library comprising polynucleotides encoding an isoprenoid producing enzyme having a desired property, wherein the polynucleotides are produced by: a) subjecting a polynucleotide encoding an isoprenoid producing enzyme to a mutagenesis process so as to produce a progeny polynucleotide set; selecting a subset of the progeny polynucleotide set, wherein the subset comprises polynucleotides encoding isoprenoid producing enzymes having a desired property; and selecting individual members of the subset comprising the desired property; or b) providing a population of variants of a polynucleotide encoding at least a portion of an isoprenoid producing enzyme, at least one of which is in cell-free form; rearranging the variants of the polynucleotide to form recombinant polynucleotides; and selecting variants comprising the desired property. In some embodiments, the combinatorial library is such wherein the isoprenoid producing enzyme is FPP synthase, GPP synthase, GGPP synthase, or a chimeric or fusion synthase (for example, a GPP/FPP synthase); wherein the desired property is increased enzyme activity, increased enzyme flux, altered product profile, reduced Km for substrate, increased ligand affinity, performs a novel activity, increased enzyme stability or increased solubility; wherein the novel activity is the production of an isoprenoid not normally produced by the enzyme; wherein the mutagenesis process targets at least one pre-selected portion of the polynucleotide, wherein the enzyme is FPP from *Gallus gallus* and the pre-selected portion comprises amino acid residues 97-137, residues 175-198, residues 250-290, or a combination thereof; or wherein the mutagenesis process is look-through mutagenesis or walk-through mutagenesis.

BRIEF DESCRIPTION OF THE DRAWINGS

These and other features, aspects, and advantages of the present disclosure will become better understood with regard to the following description, appended claims and accompanying figures where:

FIGS. 5A, B, and C show the genomic organization of exemplary plant terpenoid synthase genes.

FIG. 6 shows a sequence alignment of 11 isoprenoid synthesis enzymes. From top to bottom: SEQ ID NO: 7. SEQ ID NO: 8. SEQ ID NO: 11, SEQ ID NO: 10. SEQ ID NO: 6. SEQ ID NO: 9, SEQ ID NO: 29, SEQ ID NO: 2, SEQ ID NO: 4, SEQ ID NO: 5, and SEQ ID NO: 3.

FIG. 11 shows conifer and other selected terpene synthases.

DETAILED DESCRIPTION

Figure 1:
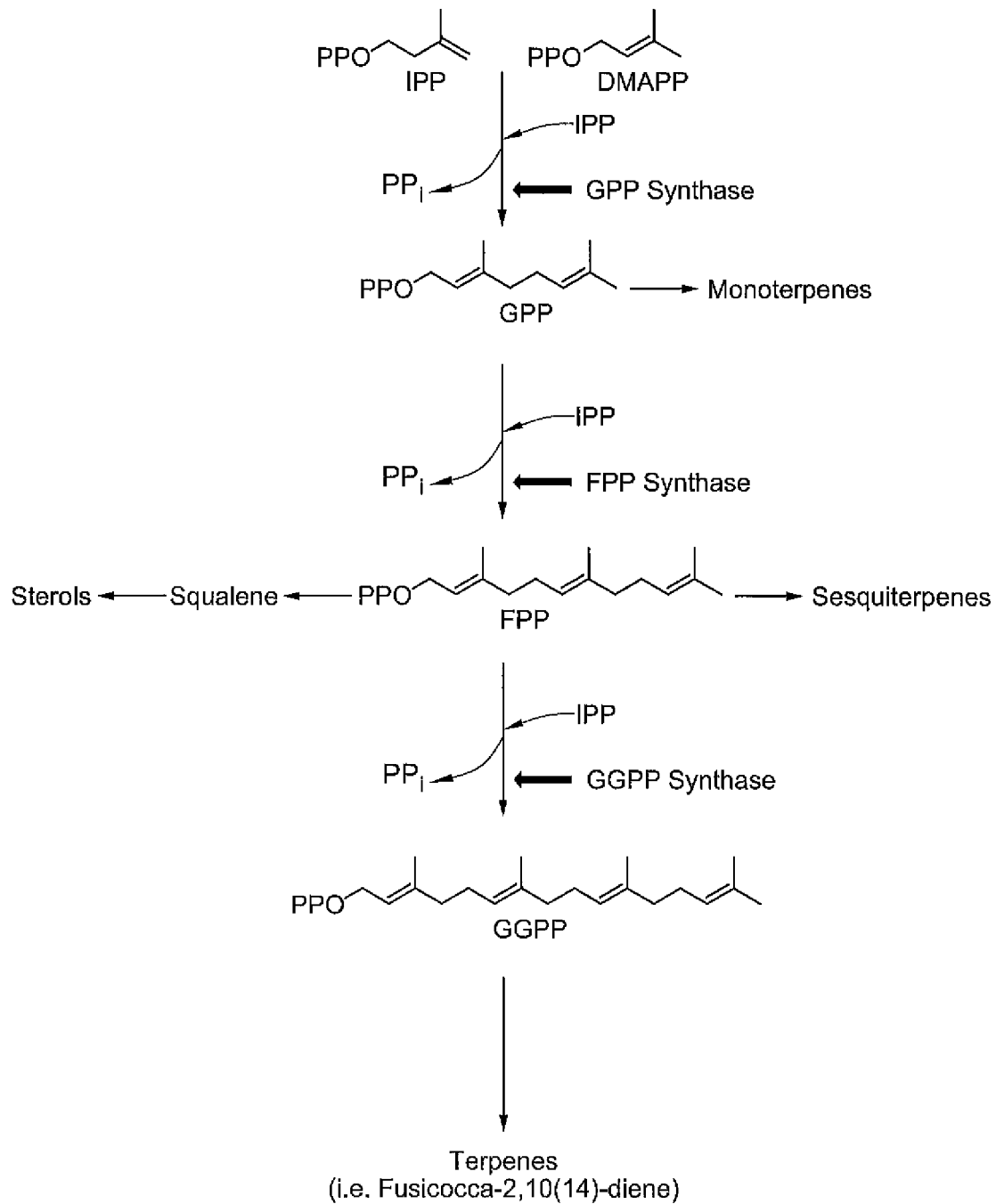
FIG. 1 shows the isoprenoid pathway, and exemplary products of the pathway, for example, fusiccoca-2,10(14)-diene.

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present disclosure.

As used in this specification and the appended claims, the singular forms "a", "an" and "the" include plural reference unless the context clearly dictates otherwise.

This disclosure provides methods of designing and generating polypeptide variants that have altered properties compared to a parent polypeptide. In addition, the present disclosure provides methods of generating polypeptide variants of isoprenoid synthase and/or prenyl transferase enzymes having at least one desired property not present in the parent polypeptide. The present disclosure further provides polypeptides representing the above variants and polynucleotides encoding the above variants, as well as vectors and host cells comprising the polynucleotides encoding the variants. The present disclosure also provides methods of using the variant polypeptides to generate isoprenoid compounds, for example, terpenes.

An important biochemical distinction between the prenyl transferase and isoprenoid synthase enzymes are that the prenyl transferases catalyze carbon-carbon bond formation between two substrate molecules, whereas the synthases catalyze an intramolecular carbon-carbon bond formation.

Endogenous

An endogenous nucleic acid, nucleotide, polypeptide, or protein as described herein is defined in relationship to the host organism. An endogenous nucleic acid, nucleotide, polypeptide, or protein is one that naturally occurs in the host organism.

Exogenous

An exogenous nucleic acid, nucleotide, polypeptide, or protein as described herein is defined in relationship to the host organism. An exogenous nucleic acid, nucleotide, polypeptide, or protein is one that does not naturally occur in the host organism or is a different location in the host organism.

Variant Polypeptide

The terms "variant polypeptide," "variant protein," or "variant enzyme" are used interchangeably throughout the disclosure. Variant polypeptides are polypeptides that comprise an amino acid sequence that has been modified from the amino acid sequence of a parent polypeptide. For example, an amino acid that is present in the parent polypeptide is substituted with a different amino acid. For example, variant polypeptides of the present disclosure are prenyl transferases or isoprenoid synthases. The terms "polypeptide variant", "protein variant," or "enzyme variant" are meant to have the same meaning as "variant polypeptide," "variant protein," or "variant enzyme." A "parent" polypeptide is an unmodified version of the corresponding "variant polypeptide." The "parent" polypeptide, for example, is the peptide as it is found in nature in a host organism.

The present disclosure provides variant polypeptides that exhibit one or more altered properties compared to a parent polypeptide. In one embodiment, the variant polypeptide is a prenyl transferase enzyme. In another embodiment, the variant polypeptide is an isoprenoid synthase enzyme. In yet another embodiment, a variant polypeptide is an enzyme involved in the isoprenoid biosynthetic pathway. Parent prenyl transferase and isoprenoid synthase enzymes are known in the art.

Methods and compositions described herein may take advantage of naturally occurring product production pathways in an organism, for example, a photosynthetic organism. An example of one such production pathway is the isoprenoid biosynthetic pathway. Methods and compositions described herein may take advantage of naturally occurring biological molecules as substrates for the variant enzyme or enzymes of interest. IPP, DMAPP, FPP, and GPP, for example, may serve as substrates for variant enzymes of the present disclosure, and may be natively produced in bacteria, yeast, and algae (e.g., through the mevalonate pathway or the MEP pathway (see FIG. 2 and FIG. 3)).

Insertion of a gene encoding a variant enzyme of the present disclosure into a host organism can lead to the increased production of a terpene/terpenoid and/or derivative. Production of a terpene/terpenoid derivative may be increased by introducing a variant enzyme that modulates the isoprenoid biosynthetic pathway.

A variant polypeptide or enzyme can comprise, for example, any one of the amino acid sequences as set forth, for example, in Table 2 and SEQ ID NOs: 1 to 11, 23, and 29 (for example, FPP synthase from *G. gallus*), or can comprise any one of the amino acid sequences as set forth in Table 2 and SEQ ID NOs: 1 to 11, 23, and 29, with at least one amino acid substitution. In some embodiments, a variant polypeptide can comprise an amino acid sequence comprising from one amino acid substitution to about 50 amino acid substitutions compared to, for example, any one of the amino acid sequences set forth in Table 2 and SEQ ID NOs: 1 to 11, 23, and 29. In some embodiments, a variant enzyme comprises at least one, at least two, at least three, at least four, at least five, at least six, at least seven, at least eight, at least nine, or at least amino acid substitutions, from about 10 amino acid substitutions to about 12 amino acid substitutions, from about 12 amino acid substitutions to about 15 amino acid substitutions, from about 15 amino acid substitutions to about 20 amino acid substitutions, from about 20 amino acid substitutions to about 25 amino acid substitutions, or from about 25 amino acid substitutions to about 50 amino acid substitutions, as compared to any one of the amino acid sequences as set forth in Table 2 and SEQ ID NOs: 1 to 11, 23, and 29 (for example, limonene synthase).

In some embodiments, an amino acid sequence encoding a variant isoprenoid synthase has at least about 75%, at least about 80%, at least about 85%, at least about 90%, at least about 95%, at least about 98%, or at least about 99% amino acid sequence identity to the amino acid sequence of any one of the isoprenoid synthases as set forth in Table 2.

In other embodiments, an amino acid sequence encoding a variant prenyl transferase (for example, a FPP synthase) has at least about 75%, at least about 80%, at least about 85%, at least about 90%, at least about 95%, at least about 98%, or at least about 99%0 amino acid sequence identity to an amino acid sequence of any one of the prenyl transferases set forth in Table 2, or SEQ ID NO: 29 (FPP synthase).

In other embodiments, an amino acid sequence encoding a variant prenyl transferase (for example, a FPP/GPP synthase) has at least about 75%, at least about 80%, at least about 85%, at least about 90%, at least about 95%, at least about 98%, or at least about 99% amino acid sequence identity to the amino acid sequence set forth in SEQ ID NO: 8.

A variant polypeptide of the present disclosure can be produced synthetically, or can be produced recombinantly, i.e., a variant polypeptide of the present disclosure can be inserted into an expression vector, and the coding region transcribed and translated, either in a living cell or in an in vitro transcription/translation system. One may employ solid phase peptide synthesis techniques, where such techniques are known to those of skill in the art (for example, as described in The Chemical Synthesis of Peptides (Clarendon Press, Oxford) (1994)). Generally, in such methods a peptide is produced through the sequential additional of activated monomeric units to a solid phase bound growing peptide chain.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and are commercially available, as are polynucleotides containing such nucleotide analogs (for example, as described in Lin et al., *Nucl. Acids Res.* 22:5220-5234, 1994; Jellinek et al., *Biochemisty* 34:11363-11372, 1995; and Pagratis et al., *Nature Biotechnol.* 15:68-73, 1997). A phosphodiester bond can link the nucleotides of a polynucleotide of the present disclosure; however other bonds, including a thiodiester bond, a phosphorothioate bond, a peptide-like bond and any other bond known in the art may be utilized to produce variant polynucleotides (for example, as described in Tam et al., *Nucl. Acids Res.* 22:977-986, 1994; and Ecker and Crooke, *BioTechnology* 13:351360, 1995).

The variant protein or enzyme may be isolated and/or purified in accordance with conventional methods known to one of skill in the art. A lysate may be prepared of the expression host, and the lysate purified using high performance liquid chromatography, size exclusion chromatography, gel electrophoresis, affinity chromatography, or other purification techniques known to one of skill in the art.

An enzyme involved in isoprenoid production is, for example, any enzyme listed in FIGS. 1, 2, 3, 5A, 5B, 5C, 6, 7, 8, 9, FIG. 11, Table 2, and any enzyme described throughout the disclosure. An enzyme can be a variant enzyme or a parent enzyme. An isoprenoid can be, for example, any of the compounds described in FIG. 11, FIG. 1, FIG. 3, and FIG. 4, and any isoprene, isoprenoid, terpene, or terpenoid described throughout the disclosure, including products that can be made using the compositions and methods disclosed herein.

Percent Sequence Identity

One example of an algorithm that is suitable for determining percent sequence identity or sequence similarity between nucleic acid or polypeptide sequences is the BLAST algorithm, which is described, e.g., in Altschul et al. *J. Mol. Biol.* 215:403-410 (1990). Software for performing BLAST analysis is publicly available through the National Center for Biotechnology Information. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (as described, for example, in Henikoff & Henikoff (1989) *Proc. Natl. Acad. Sci. USA,* 89:10915). In addition to calculating percent sequence identity, the BLAST algorithm also can perform a statistical analysis of the similarity between two sequences (for example, as described in Karlin & Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

Homologous sequences are, for example, those that have at least 50%, at least 60%, at least 70%, at least 80%, at least 90%, at least 95%, at least 98%, or at least at least 99% sequence identity to a reference amino acid sequence, for example, the amino acid sequence found naturally in the host cell.

Altered Properties

As used herein, the term "altered property" and "altered properties" refers to one or more characteristics present in a variant polypeptide that is not present or modified in the parent polypeptide. An altered property can be a desired property or an undesired property. A desired property can be, for example, a change in a physical property of the polypeptide. A desired property allows the variant polypeptide to have a characteristic that is desired or perform a function that is desired. Desired properties include, but are not limited to, increased enzymatic activity (for example, an increased $k_{cat}$); increased enzyme flux; altered product profile; decreased Km value for a substrate; increased ligand binding affinity (increased substrate affinity); performance of a novel activity (e.g., production of a polyisoprenoid not normally produced by the parent polypeptide); prolonged retention of enzyme activity; increased solubility (e.g., increased solubility in the cytosol of a prokaryotic host cell); and increased stability (e.g., increased in vivo and/or in vitro half life). In some embodiments, e.g., where the enzyme is produced recombinantly in a host cell (e.g., an algal host cell), an altered property such as increased solubility and/or improved folding, can result in increased enzymatic activity, compared to the enzymatic activity of a parent polypeptide produced recombinantly in the host cell.

An altered product profile or property, can be, for example, a variation in the enzymatic reaction product(s) from the variant polypeptide. For example, for enzymes that create multiple products, an altered product profile may result in a different ratio of one product compared to another product. Thus, a variant polypeptide may generate an increased amount of a product from the same amount of starting material.

Libraries of mutants generated by any of the disclosed techniques or other suitable techniques can be screened as described herein to identify mutants of desired structure or activity. The screening can be done by any appropriate means. For example, catalytic activity can be ascertained by suitable assays for substrate conversion and binding activity can be evaluated by standard immunoassay and/or affinity chromatography.

For example, if a DNA fragment which encodes for a protein with increased binding affinity to a ligand is desired, the proteins expressed by each of the DNA fragments in the population or library may be tested for their ability to bind to the ligand by methods known in the art (e.g., panning or affinity chromatography). If a DNA fragment which encodes for a protein with increased enzymatic activity is desired, the proteins expressed by each of the DNA fragments in the population or library may be tested for their enzymatic activity in the host organism. One skilled in the art, given knowledge of the desired protein, could readily test the population to identify DNA fragments which confer the desired properties onto the protein.

Decreased Km

A decreased Km value for a substrate refers to the concentration of substrate required in order to achieve 50% of the Vmax value of the enzyme. A decreased Km value results in a higher velocity of reaction at lower substrate concentrations, but does not necessarily affect the Vmax, or maximal speed of the enzyme activity. Methods of determining Km values for a enzyme are well known in the art (for example, as described in A. Fersht, *Structure and Mechanism in Protein Science,* 1998). For example, a variant enzyme may have a decreased Km value of at least 5% as compared to the parent enzyme. As another example, the variant enzyme may have a decreased Km value of at least 10%, at least 15%, at least 20%, at least 25%, at least 50%, at least 60%, at least 70%, at least 80%, at least 90%, or greater as compared to the parent enzyme.

Increased Binding Affinity

Increased ligand binding affinity refers to the strength of binding between a protein and a substrate or ligand. An increased ligand binding affinity results in stronger binding between the protein and the substrate. Methods for determining binding affinity are well known in the art, and include, for example, a competitive binding assay. For example, a variant protein may have an increased binding affinity of at least 5% as compared to the parent protein. In another embodiment, a variant protein may have an increased binding affinity of at least 10%, at least 15%, at least 20%, at least 25%, at least 50%, at least 60%, at least 70%, at least 80%, at least 90%, or greater, as compared to the parent protein. The binding affinity may be measured as the molar concentration at which 50% maximum binding occurs (for example, $K_d$). For example, a variant protein may have an $K_d$ of about 10 nM, about 50 nM, about 100 nM, about 500 nM, about 1 uM, about 2 uM, about 3 uM, about 4 uM, about 5 uM, or greater, as compared to the parent protein.

Novel Activity

A variant polypeptide may also perform a novel activity, meaning that the variant polypeptide performs a function that the parent polypeptide does not perform. For example, the expression of a variant polypeptide may generate an increase in a product as compared to a parent polypeptide.

For example, the expression of a variant prenyl transferase may generate a polyisoprenoid that is not normally generated by the expression of the parent polypeptide. In this way, the expression of a variant polypeptide may, for example, generate polypeptides that are capable of producing long chain isoprenoid compounds, differentially cyclized isoprenoid compounds, or other unique isoprenoid structures. For example, a long chain isoprenoid compound may be an isoprenoid compound that is not normally generated by the expression of the parent polypeptide, such as geranyl diphosphate (GPP), farnesyl diphosphate (FPP), geranylgeranyl diphosphate (GGPP), hexaprenyl diphosphate (HexPP), heptaprenyl diphosphate (HepPP), octaprenyl diphosphate (OPP), solanesyl diphosphate (SPP), decaprenyl diphosphate (DPP), nonaprenyl diphosphate (NPP), and undecaprenyl diphosphate (UPP). Alternatively, a long chain isoprenoid compound may contain a longer chain isoprenoid than those listed above, through the conjugation of additional isoprenoid units. A long chain isoprenoid may contain at least 5, at least 10, at least 15, at least 20, at least 25, at least 30, at least 35, at least 40, at least 45, at least 50, or greater carbon molecules in the backbone. A person of skill in the art could determine the carbon backbone length.

Retention of Protein Activity

A variant protein may also prolonged retention of protein activity, meaning that the variant protein is capable of functioning for a longer period of time than the parent protein under the same conditions. Often in chemical reaction conditions (e.g. during industrial applications), a protein is degraded over time due to a variety of factors, such as built up heat in the reaction or variant pH levels (e.g., the reaction conditions become highly acidic or basic). Methods of the present disclosure may produce a variant protein that can retain activity for a prolonged period of time. For example, under the same reaction conditions, a variant prenyl transferase may retain at least 80% activity at pH 7 for at least 5 minutes longer than the parent prenyl transferase. As another example, under the same reaction conditions, a variant prenyl transferase may retain at least 80% activity at pH 7 for at least 10 minutes longer, at least 15 minutes longer, at least 20 minutes longer, at least 25 minutes longer, at least 30 minutes longer, at least 45 minutes longer, at least 60 minutes longer, at least 90 minutes longer, at least 120 minutes longer, or greater than the parent polypeptide.

Altered Intracellular Properties

Altered properties also include altered intracellular properties, e.g., an increased intracellular solubility in a host cell (e.g., increased solubility in the cytosol or cytoplasm of a host cell); a reduced likelihood that a variant polypeptide produced by a host cell will be sequestered in an inclusion body; and improved folding (e.g., increased degree of native folding or an increased proportion of protein that exhibits native folding). For example, where a variant polypeptide is produced recombinantly in a host cell (e.g., an algal host cell), the variant polypeptide may exhibit one or more of: a) an increased solubility in the cytosol or cytoplasm of the host cell, compared to the solubility of the parent polypeptide when produced recombinantly in the host cell; an increased proportion of the variant polypeptide that is soluble in the cytosol compared to the proportion of the parent polypeptide that is soluble in the cytosol when produced recombinantly in the host cell; an increased proportion of the variant polypeptide that is soluble in chloroplasts compared to the proportion of the parent polypeptide that is soluble in chloroplasts when produced recombinantly in the host cell; a reduced proportion of the variant polypeptide that is insoluble, e.g., sequestered in an inclusion body compared to the proportion of the parent polypeptide that is insoluble when produced recombinantly in the host cell; a reduced proportion of the variant polypeptide that is present in an aggregate (e.g., an insoluble aggregate) compared to the proportion of the parent polypeptide that is present in an aggregate when produced recombinantly in the host cell; and an increased native folding, e.g., the proportion of variant polypeptide that exhibits native folding is increased, compared to the proportion of the parent polypeptide that exhibits native folding when produced recombinantly in the host cell.

Prenyl Disphosphates

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

Pyrophshate

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; and the terms farnesyl diphosphate" and farnesyl pyrophosphate" are interchangeable.

Prenyl Transferases

The prenyl transferases (also called prenyl diphosphate synthases) catalyzes the consecutive 1'-4' condensation of isopentenyl diphosphate with allylic primer substrates, resulting in the formation of prenyl diphosphates of various chain lengths. As used herein, the term "prenyl transferase" is used interchangeably with the terms "isoprenyl diphosphate synthase" and "polyprenyl synthase" (e.g., "GPP synthase," "FPP synthase," "OPP synthase," and "GGPP synthase").

Prenyl transferases can be a trans or a cis-prenyl transferase. In both prokaryotes and eukaryotes, trans-prenyl transferases catalyze the formation of isoprenoid compounds, such as geranyl diphosphate (GPP; C10), farnesyl diphosphate (FPP; C15) and geranylgeranyl diphosphate (GGPP; C20), which serve as initiating molecules to produce many other longer chain length isoprenoid compounds necessary for cellular growth and survival. Prenyl transferases synthesize a number of various isoprenoid compounds, for example, sterols, carotenoids, terpenes, quinones, glycosyl carrier lipids, prenyl proteins and natural rubber. The structural genes for FPP synthase (FPS) and GGPP synthase (GGPS) as well as several other prenyl diphosphate synthases have been cloned and characterized from various organisms. The family of "short-chain prenyl transferases" comprises, for example, GPP synthase, farnesyl diphosphate (FPP; $C_{15}$) synthase, and geranylgeranyl diphosphate (GGPP, $C_{20}$) synthase. Genes encoding FPP synthase and GGPP synthase, for example, have been isolated from a range of organisms in which they play a central role in both primary and secondary isoprenoid metabolism.

A prenyl transferase enzyme catalyzes the consecutive 1'-4' condensation of isopentenyl diphosphate with allylic primer substrates, resulting in the formation of prenyl diphosphates of various chain lengths. Polyprenyl diphosphate substrates that can serve as a substrate for a variant isoprenoid synthase include, but are not limited to, geranyl diphosphate (GPP), farnesyl diphosphate (FPP), geranylgeranyl diphosphate (GGPP), hexaprenyl diphosphate (HexPP), heptaprenyl diphosphate (HepPP), octaprenyl diphosphate (OPP), solanesyl diphosphate (SPP), decaprenyl diphosphate (DPP), nonaprenyl diphosphate (NPP), and undecaprenyl diphosphate (UPP). In some embodiments, the substrate of a variant prenyl transferase is GPP. In other embodiments, the substrate of a variant prenyl transferase is FPP. In other embodiments, the substrate of a variant prenyl transferase is GGPP.

There are three main classes of prenyltransferases: (a) isoprenyl pyrophosphate synthases (IPPSs), which catalyze chain elongation of allylic pyrophosphate substrates via consecutive condensation reactions with isopentenyl pyrophosphate (IPP) to generate linear polymers with defined chain lengths; (b) protein prenyltransferases, which catalyze the transfer of an isoprenyl pyrophosphate (e.g. farnesyl pyrophosphate) to a protein or a peptide; and (c) prenyltransferases, which catalyze the cyclization of isoprenyl pyrophosphates. The structure, mechanism, and function of these three classes of prenyltransferases are described in Liang, P., et al., Eur. J. Biochem. 269, 3339-3354 (2002).

Class I: Isoprenyl Pytophosphate Synthases (IPPSs)

Many trans-IPPSs have been purified and their genes cloned (for example, as described in Ogura, K., et al. (1997) Polyprenyl diphosphate synthases. In Subcellular Biochemistry (Bittman, R., ed.), Vol. 28, pp. 57-88. Plenum, New York; and Wang, K. & Ohnuma, S. (1999) Trends. Biochem. Sci. 24, 445-451). The deduced amino-acid sequences of these enzymes show amino-acid sequence homology and two common DDxxD motifs (Ashby, M. N., et al. (1992) J. Biol. Chem. 267, 4128-4136; Koyama, T., et al. (1993) J. Biochem. (Tokyo) 113, 355-363; and Chen, A., et al. (1994) Protein Sci. 3, 600-607). These Asp-rich motifs were recognized from the 3D structure (Tarshis, L. C., et al. (1994) Biochemistry 33, 10871-10877) and site-directed mutagenesis studies (Marrero, P. F., et al. (1992) J. Biol. Chem. 267, 21873-21878; Joly, A. and Edwards, P. A. (1993). J. Biol. Chem. 268, 2626983-26989; Song, L. and Poulter, C. D. (1994) Proc. Natl. Acad. Sci. U.S.A. 91, 3044-3048; Koyama, T., et al. (1995) Biochem. Biophys. Res. Commun. 212, 681-686; Koyama, T., et al. (1996) Biochemistry, 35, 9533-9538; and Koyama, T., et al. (1994) Biochemistry 33, 12644-12648) to be involved in substrate binding and catalysis via chelation with Mg2+, a cofactor required for enzyme activity.

Class II: Protein Prenyl-Transferases

Ras FTase is a Zn2+-dependent prenyltransferase containing an α and β heterodimer, which catalyzes the farnesylation on a C-terminal CaaX motif of the Ras protein. The Zn2+-activated thiolate of Cys acts as a nucleophile to attack the ionized farnesyl group. In the 3D structure of a mammalian Ras FTase, both subunits are largely composed of α helices (Park, H. W., et al. (1997) Science 275, 1800-1804). The α-2 to α-15 helices in the α subunit fold into a novel helical hairpin structure, resulting in a crescent-shape domain that envelopes part of the β subunit. On the other hand, the 12 helices of the β subunit form a α-α barrel. Six additional helices connect the inner core of helices and form the outside of the helical barrel. A deep cleft surrounded by hydrophobic amino acids in the center of the barrel is proposed as the FPP-binding pocket. A single Zn2+ ion is located at the junction between the α-hydrophilic surface groove near the subunit interface and the deep cleft in the β-subunit. This Zn2+ ion is pentaco-ordinated by the Asp297 and Cys299 located in the N-terminal helix 11, His362 in helix 13 of the β-subunit, and a water molecule as well as a bidentate ligand Asp2973. Replacement of Cys299β with Ala results in lower Zn2+ affinity and abolishes enzyme activity (Fu, H. W., et al. (1996) J. Biol. Chem. 271, 28541-28548). A nine amino-acid portion of the adjacent β-subunit in the crystal lattice was found to bind in the positively charged pocket of the β-subunit close to the FPP site.

Class III: Terpenoid Cyclases

Terpenoid cyclases such as, for example, squalene cyclase, pentalenene synthase, 5-epi-aristolochene synthase, and trichodiene synthase are responsible for the synthesis of cholesterol, a hydrocarbon precursor of the pentalenolactone family of antibiotics, a precursor of the antifungal phytoalexin capsidiol, and the precursor of antibiotics and mycotoxins, respectively. The last three enzymes catalyze the cyclization of FPP involving: (a) ionization of FPP to an allylic cation which acts as electrophile to react with one of the π bonds of the substrate for cyclization; (b) relocalization of the carbocation via hydride transfer and Wagner-Meerwein rearrangements; and (c) deprotonation or capture of an exogenous nucleophile such as water to eliminate the carbocation. Squalene synthase catalyzes the cyclization of squalene, which is formed by coupling two FPP molecules. Like trans-type IPPSs, which make linear polymers from FPP, the four cyclases also contain conserved Asp-rich motifs, suggesting that these enzymes have similar strategies for activating FPP. In the structures of these three enzymes, the similar structural feature referred to as "terpenoid synthase fold" with 10-12 mostly antiparallel α helixces is found, as also observed in IPPS and FTase.

In some embodiments, a variant prenyl transferase provides for production of an isoprenoid product at a level that is at least about 5%, at least about 10%, at least about 15%, at least about 20%, at least about 25%, at least about 50%, at least about 75%, or at least about 90% greater than the level produced by a parent prenyl transferase under similar conditions. In some embodiments, a variant prenyl transferase provides for production of an isoprenoid at a level that is at least about two-fold, at least about 2.5-fold, at least about 5-fold, at least about 7.5-fold, at least about 10-fold, at least about 25-fold, at least about 50-fold, or at least about 100-fold greater than the level produced by a parent prenyl transferase under similar conditions.

For example, a variant prenyl transferase can comprise the amino acid sequence of SEQ ID NO: 29, or a variant prenyl transferase can comprise the amino acid sequence of SEQ ID NO: 29 with at least one amino acid substitution. In some embodiments, a variant prenyl transferase comprises an amino acid sequence that has from one amino acid substitution to about 50 amino acid substitutions compared to the amino acid sequence of SEQ ID NO: 29. In some embodiments, a variant prenyl transferase comprises one, two, three, four, five, six, seven, eight, nine, or 10 amino acid substitutions, from about 10 amino acid substitutions to about 12 amino acid substitutions, from about 12 amino acid substitutions to about 15 amino acid substitutions, from about 15 amino acid substitutions to about 20 amino acid substitutions, from about 20 amino acid substitutions to about 25 amino acid substitutions, or from about 25 amino acid substitutions to about 50 amino acid substitutions compared to any one of the SEQ ID NOs: 1-11, 23, or 29.

A variant prenyl transferase can be modified in different regions. For example, a variant prenyl transferase may be modified in regions that bind to a substrate. In one embodiment, a variant prenyl transferase can comprise at least one amino acid substitution in any one or more regions (region 1=amino acids 97-137; region 2=amino acids 175-198; and region 3=amino acids 250-290) of a chicken FPP synthase. A variant prenyl transferase gene, can for example, contain at least 1, at least 2, at least 3, at least 4, at least 5, at least 10, at least 15, at least 20, at least 25, or more amino acid substitutions at residue regions 97-137, 175-198, and/or 250-290. The variant prenyl transferase can additionally, for example, contain amino acid substitutions in other regions of the enzyme or the variant prenyl transferase can be free of amino acid substitutions in other regions of the enzyme. A person of ordinary skill in the art would be able to align a sequence with the sequence of SEQ ID NO: 29 to determine which regions of the sequence corresponded with the three regions of the prenyl transferase described above. Furthermore, one of skill in the art would be able to align any two amino acid or nucleotides sequences to determine, for example, regions of sequence identity or similarity, amino acid homology, and common motifs of nucleotides and/or amino acids. One of skill in the art could align a sequence with any one or more of SEQ ID NOs: 1 to 11, 23, or 29.

Isoprenes and Isoprenoids

Over 55,000 individual isoprenoid compounds have been characterized, and hundreds of new structures are reported each year. Most of the molecular diversity in the isoprenoid pathway is created from the disphosphate esters of simple linear polyunsaturated allylic alcohols such as dimethyl alcohol (a 5-carbon molecule), geranoil (a 10-carbon molecule), farnesol (a 15-carbon molecule), and geranylgeraniol (a 20-carbon molecule). The hydrocarbon chains are constructed one isoprene unit at a time by addition of the allylic moiety to the double bond in isopentenyl diphosphate, the fundamental five-carbon building block in the pathway, to form the next higher member of the series. Geranyl, farnesyl, and geranylgeranyl diphosphate lie at multiple branch points in the isoprenoid pathway and are substrates for many enzymes. These are primary cyclases, which are responsible for generating the diverse carbon skeletons for the synthesis of the thousands of mono-, sequi-, di-, and triterpenes; sterols; and carotenoids found in nature. The structures of several of these cyclases have been reported (Lesburg, C. A., et al., Science, Vol. 277, 1820 (1997); Wendt, K. U., et al., Science, Vol. 277, 1811 (1997); and Starks, C. M., et al., Science, Vol. 277, 1815 (1997)).

The extensive family of isoprenoid compounds is synthesized from two-precursors, isopentenyl diphosphate and dimethylallyl disphosphate. The chain elongation and cyclization reactions of isoprenoid metabolism are electrophillic alkylations in which a new carbon-carbon single bond is formed by attaching a highly reactive electron-deficient carbocation to an electron-rich carbon-carbon double bond. From a chemical viewpoint, the most difficult step is generation of the carbocations. Nature has selected three strategies for catalysis: cleavage of the carbon-oxygen bond in an allylic disphosphate ester; protonation of a carbon-carbon double bond, or protonation of an epoxide. Once formed, the carbocations can rearrange by hydrogen atom or alkyl group shifts and subsequently cyclize by alkylating nearby double bonds. Diverse families of isoprenoid structures, often formed from the same substrate in and enzyme-specific manner, are thought to arise from differences in (i) the way substrate is folded in the active site, (ii) how carbocationic intermediates are stabilized to encourage or discourage rearrangements, and (iii) how positive charge is quenched when the product is formed.

Several of the enzymes involved in isoprenoid chain elongation and cyclization have been studied and genetic information is available for some of the enzymes. Although there is little overall similarity between amino acid sequences for the chain elongation and cyclization enzymes, proteins from both classes that use allylic disphosphates as substrates contain highly conserved aspartate-rich DDXXD motifs (D is aspartate, X is any amino acid) thought to be Mg2+ binding sites.

The cyclase domains of the three isoprenoid cyclases as well as farnesyl diphosphate synthase have a similar structural motif, consisting of 10 to 12 mostly antiparallel, alpha helices that form a large active site cavity (as described in Tarshis, L. C., Biochemistry, 33, 10871 (1994)). Lesburg, C. A., et al. (Science, Vol. 277, 1820 (1997)) have labeled this motif the "isoprenoid synthase fold," In addition, aspartate-rich clusters are present in all four proteins. Three enzymes that use disphosphate-containing substrates (pentalenene synthase, epi-aristolochene synthase, and farnesyl disphosphate synthase) all contain DDXXD on the walls of their active site cavity (for example, as described in Sacchettini, J. C., and Poulter, C. D, Science, Vol. 277, no. 5333, pp. 1788-1789 (1997)). The aspartates are involved in binding multiple Mg2+ ions. The amino acid sequence of hopene synthase also contains a DDXXD motif. Pentalenene synthase and epi-aristolochene synthase also catalyze proton-promoted cyclizations (as described in for example, Sacchettini, J. C., and Poulter, C. D, Science, Vol. 277, no. 5333, pp. 1788-1789 (1997); and Starks, C. M., et al., Science, Vol. 277, 1815 (1997)).

Terpenes and Terpenoids

Liquid fuels (gasoline, diesel, jet fuel, kerosene, etc) are primarily composed of mixtures of paraffinic and aromatic hydrocarbons. Terpenes are a class of biologically produced molecules synthesized from five carbon precursor molecules in a variety of organisms. Terpenes are pure hydrocarbons, while terpenoids may contain one or more oxygen atoms. Because they are hydrocarbons with a low oxygen content and contain no nitrogen or other heteroatoms, terpenes can be used as fuel components with minimal processing (as described, for example, in Calvin, M, (2008) "Fuel oils from euphorbs and other plants" Botanical Journal of the Linnean Society 94:97-110, and U.S. Pat. No. 7,037,348).

Terpenes are a subset of isoprenes. Terpenes are synthesized in biological systems from two five-carbon precursor molecules, isopentyl-diphosphate and dimethylallyldiphosphate (see FIG. 2). The five-carbon precursors are produced through two pathways, the MEP and the mevalonic acid pathways (see FIG. 2 and FIG. 3). Through condensation reactions, the ten-, fifteen-, and twenty-precursor molecules geranyl diphosphate, farnesyl diphosphate, and geranylgeranyl diphosphate are produced by chain elongation enzymes. These terpenoids are then cyclyzed by terpene synthases into monoterpenes (C10 molecules), sesquiterpenes (C15 molecules), and diterpenes (C20 molecules). Farnesyl diphosphate can be condensed into C30 terpenes, and geranylgeranyl diphosphate can be condensed into C20, C40, or higher molecular weight terpenes. FIG. 1 and FIG. 3 provide an overview of terpenoid biosynthesis.

An overview of terpene biosynthesis in photosynthetic eukaryotes is shown in FIG. 3. The intracellular compartmentalization of the mevalonate and mevalonate-independent pathways for the production of isopentenyl diphosphate (IPP) and dimethylallyl diphosphate (DMAPP), and of the derived terpenoids, is illustrated. The cytosolic pool of IPP, which serves as a precursor of farnesyl diphosphate (FPP) and, ultimately, the sesquiterpenes and triterpenes, is derived from mevalonic acid (left). The plastidial pool of IPP is derived from the glycolytic intermediates pyruvate and glyceraldehyde-3-phosphate and provides the precursor of geranyl diphosphate (GPP) and geranylgeranyl disphosphate (GGPP) and, ultimately, the monoterpenes, diterpenes, and tetraterpenes (right). Reactions common to both pathways are enclosed by both boxes.

Figure 4:
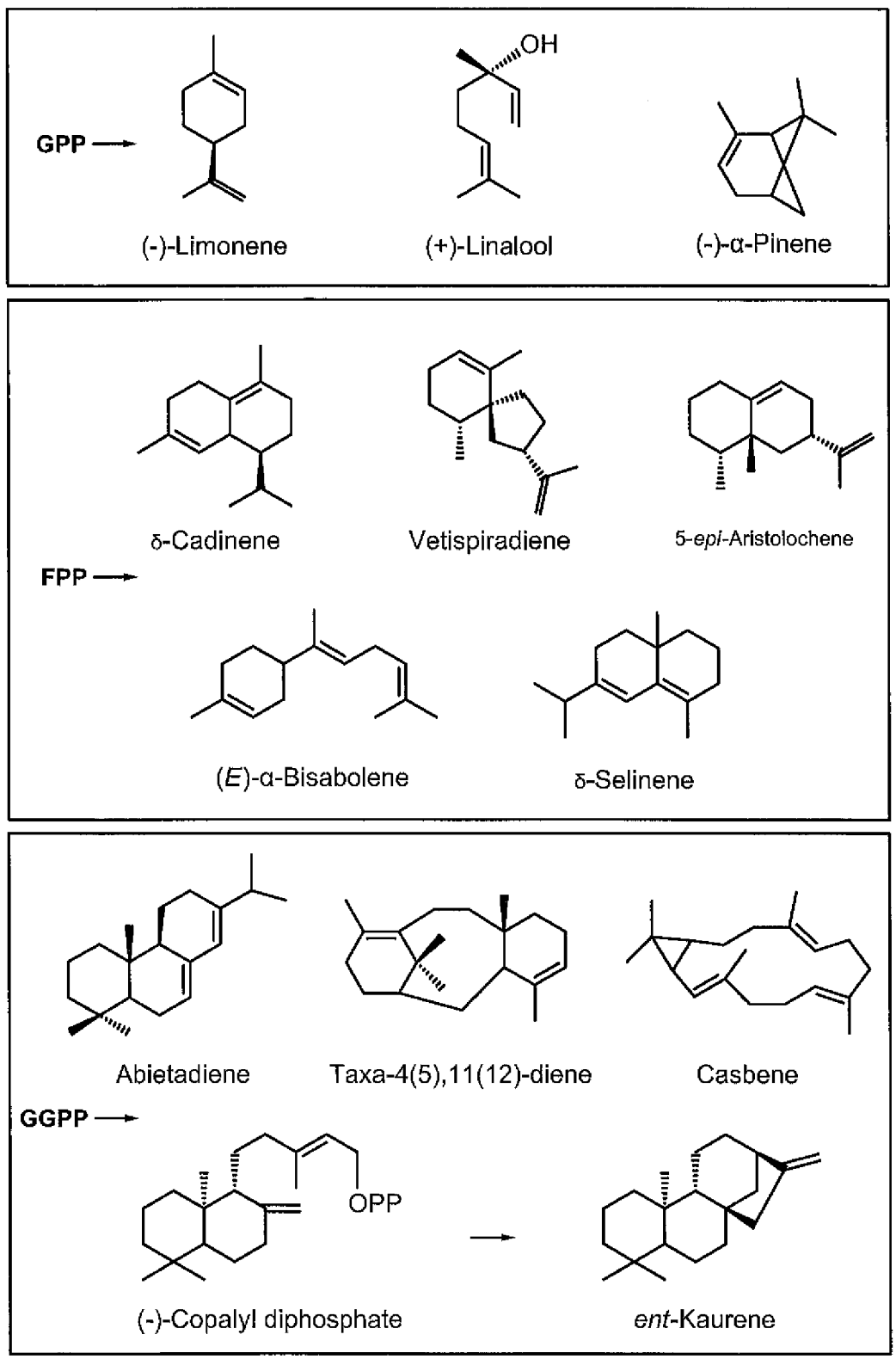
FIG. 4 shows exemplary terpenes biosynthesized by eukaryotes or prokaryotes.

Exemplary terpenes biosynthesized by eukaryotes or prokaryotes are shown in FIG. 4. Monoterpenes, sesquiterpenes, and diterpenes are derived from the prenyl diphosphate substrates, geranyl diphosphate, farnesyl diphosphate, and geranylgeranyl disphosphate, respectively, and are produced in both angiosperms and gymnosperms. (–)-copalyl diphosphate and ent-kaurene are sequential intermediates in the biosynthesis of gibberellins plant growth hormones. Examples of terpenes that can be produced by an organism, for example, an alga, a yeast, a bacteria, or a higher plant, are Casbene, Ent-kaurene, Taxadiene, or Abietadiene (as shown in FIG. 4).

Fusicoccins and Fusiococcadienes

Fusicoccins or fusiococcadienes are compounds which function in plant pathogenesis and are synthesized by the fungus *Phomopsis amygdali*. Fusiococcadiene is a cyclic diterpene formed by the condensation of isopentenyl diphosphate (IPP) and dimethylallyl diphosphate (DMAPP) to form the $C_{20}$ geranylgeranyl diphosphate (GGPP). This linear isoprenoid is then cyclized by a terpene cyclase (fusiococcadiene synthase) to form the tricyclic ring structure of fusiococca-2,10(14)-diene. In *P. amygdali*, the formation of fusiococca-2,10(14)-diene is carried out by a bifunctional enzyme fusicoccadiene synthase (PaFS), which has both a prenyltransferase domain for the formation of GGPP and a terpene cyclase domain for formation of the tricyclic ring fusiococca-2,10(14)-diene. The carbon skeleton is then modified by oxidation, reduction, methylation, and glycosylation to form fusicoccin A and fusicoccin J, which function to assist plant pathogenesis by permanently activating plant 14-3-3 proteins.

The present description provides methods and compositions for constructing genetically modified organisms expressing a variant polypeptide (for example, a variant prenyl transferase or a variant isoprenoid synthase) which produce terpenes/terpenoids, for example, including cyclical terpenes, such as fusicoccadiene, casbene, ent-kaurene, taxadiene, and abietadiene at a increased level as compared to an unmodified organism. Also provided are methods of producing terpenes/terpenoids (such as fusicoccadiene) in genetically modified organisms.

The present disclosure, among other embodiments, provides a genetically modified host cell capable of expressing a variant polypeptide, wherein expression of the variant polypeptide results in an increase in the terpene/terpenoid content of the host cell.

Terpene Synthases

As used herein, the term "terpene synthase" or "isoprenoid synthase" is meant a polypeptide that is capable of catalyzing a reaction involving the intramolecular carbon-carbon bond formation of an allylic diphosphate substrate (for example, a C10, C15, or C20 allylic diphosphate substrate) to an isoprenoid product (for example, a monoterpene, diterpene, sesquiterpene, or sterol product). Examples of such isoprenoid synthases include, without limitation, monoterpene synthases (for example, limonene synthase), diterpene synthases (for example, casbene synthase), and sesquiterpene synthases (for example, 5-epi-aristolochene synthase, vetispiradiene synthase, and cadinene synthase) that are responsible for cyclization of geranyl diphosphate (GPP), farnesyl diphosphate (FPP), and geranylgeranyl diphosphate (GGPP), respectively. A number of terpene synthases from plant and microbial sources have been isolated and characterized (for example, as described in Moestra and West, Arch. Biochem. Biophys. 238:325, 1985; Hohn and Van Middlesworth, Arch. Biochem. Biophys. 251:756, 1986; Hohn and Plattner, Arch. Biochem. Biophys. 272:137, 1989; Cane and Pargellis, Arch. Biochem, Biophys. 254:421, 1987; Munck and Croteau, Arch. Biochem. Biophys. 282:58, 1990; Alonso et al., J. Biol. Chem. 267:7582, 1992; Savage et al., J. Biol. Chem. 269:4012, 1994; Croteau et al., Arch. Biochem. Biophys. 309:184, 1994; Vogeli et al., Plant Physiol. 93:182, 1990; Guo et al., Arch. Biochem. Biophys. 308:103, 1994; and Gambliel and Croteau, J. Biol. Chem. 259:740, 1984). In general, terpene synthases are soluble enzymes having a molecular weight of about 40 to about 100 kD. Genes encoding a number of monoterpene, diterpene, and sesquiterpene synthases have been described for a number of plant and microbial organisms (for example, as described in Hohn and Beremand, Gene 79:131, 1989; Proctor and Hohn, J Biol Chem. 268:4543, 1993; Facchini and Chappell, Proc. Natl. Acad. Sci. 89:11088, 1992; Back and Chappell, J Biol. Chem. 270:7375, 1995; Colby et al., J. Biol. Chem. 268:23016, 1993; Man and West, Proc. Natl. Acad. Sci. 91:8497, 1994; Chen et al, Arch, Biochem. Biophys. 324:255, 1994; and Cane et al., Biochemistry 33:5846, 1994).

Terpene synthases are also known as terpene cyclases, and these two terms can be used interchangeably throughout the disclosure.

Generally speaking, terpene cyclases use one of three substrates—the ten carbon geranyl diphosphate, fifteen carbon farnesyl diphosphate, or twenty carbon geranylgeranyl diphosphate, as substrates. Cyclases acting on geranyl diphosphate produce ten carbon monoterpenes; those that act on farnesyl diphosphate produce sesquiterpenes, and those that act on geranylgeranyl diphosphate produce diterpenes. Some naturally occurring terpene synthase (for instance, fusicoccadiene synthase from *P. amygdali*) contain both a terpene cyclase domain, as well as a prenyl transferase or chain elongation domain. If present, this chain elongation domain will produce the GPP, FPP, or GGPP substrate for the cyclase from the five carbon isoprenoids isoprenyl diphosphate and dimethylallyl diphosphate.

In one exemplary organism (*Phomopsis amygdali*), fusicoccadiene synthase catalyzes two reactions, the first is a prenyl transferase reaction producing GGPP from three molecules of IPP and one molecule of DMAPP, and a second reaction where GGPP is cyclyzed to produce fusicocca-2,10 (14)diene and inorganic pyrophosphate. These two reactions reside in two separate domains of the protein; the N-terminal terpene cyclase and the C-terminal prenyl transferase domains.

Terpenoids are the largest, most diverse class of natural products and they play numerous functional roles in primary metabolism. Well over 30 cDNAs encoding plant terpenoid synthases involved in primary and secondary metabolism have been cloned and characterized. Terpenoids are present and abundant in all phyla, and they serve a multitude of functions in their internal environment (primary metabolism) and external environment (ecological interactions). The biosynthetic requirements for terpene production are the same for all organisms (a source of isopentenyl diphosphate, isopentyl diphosphate isomerase or other source of dimethylallyl diphosphate, prenyltransferases, and terpene synthases).

Of the more than 30,000 individual terpenoids now identified (for example, as described in Buckingham, J. (1998) *Dictionary of Natural Products on CD-ROM*, Version 6.1. Chapman & Hall, London), at least half are synthesized by plants. A relatively small, but quantitatively significant, number of terpenoids are involved in primary plant metabolism including, for example, the phytol side chain of chlorophyll, the carotenoid pigments, the phytosterols of cellular membranes, and the gibberellin plant hormones. However, the vast majority of terpenoids are classified as secondary metabolites, compounds not required for plant growth and development but presumed to have an ecological function in communication or defense (for example as described in Harborne, J. B. (1991) Recent advances in the ecological chemistry of plant terpenoids, pp. 396-426 in *Ecologial Chemistry and Biochemistry of Plant Terpenoids*, edited by J. B. Harborne and F. A Tomas-Barberan. Clarendon Press, Oxford). Mixtures of terpenoids, such as the aromatic essential oils, turpentines, and resins, form the basis of a range of commercially useful products (for example, as described in Zinkel, D. F. and Russell, J. (1989) *Naval Stores: Production, Chemistry, Utilization*. Pulp Chemicals Association, New York, p. 1060; and Dawson, F. A. (1994) The Amazing Terpenes. Naval Stores Rev. March/April: 6-12), and several terpenoids are of pharmacological significance, including the monoterpenoid (C10) dietary anticarcinogen limonene (Crowell, P. L, and Gould, M. N. (1994) CRC Crit. Rev. Oncogenesis 5:1-22), the sequiterpenoid (C15) antimalaria artemisinin (Van Geldre, E., et al. (1997) Plant Mol. Biol. 33: 199-209), and the diterpenoid anticancer drug Taxol (Holmes, F. A. et al. (1995) Current status of clinical trials with paclitaxel and docetaxel, pp. 31-57 in *Taxane Anticancer Agents: Basic Science and Current Status*, edited by G. I. George, T. T. Chen, I. Ojima and D. M. Vyas. American Chemical Society Symposium Series 583, Washington D.C.).

Figure 2:
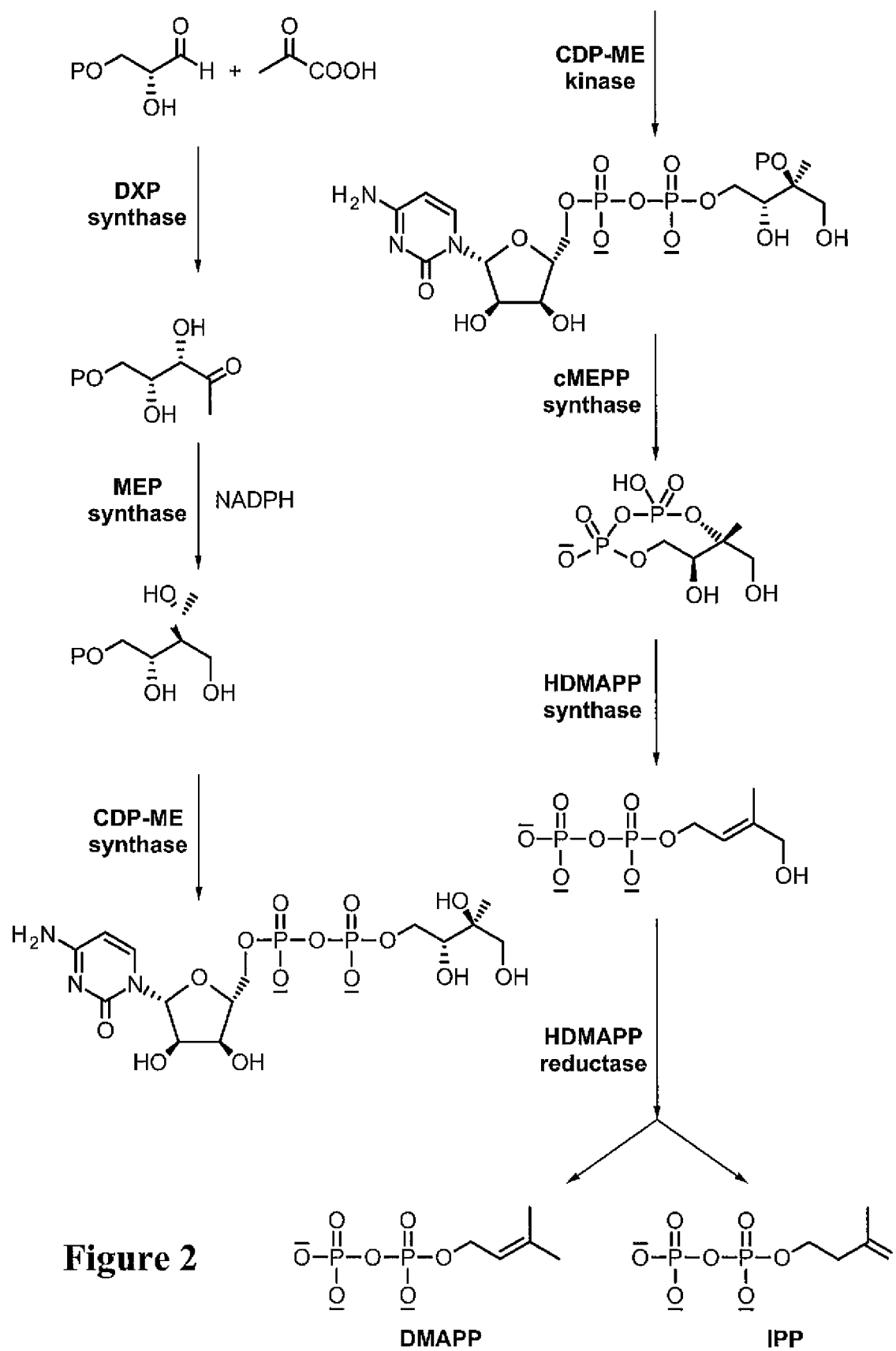
FIG. 2 shows the MEP pathway for the production of IPP and DMAPP.
Figure 3:
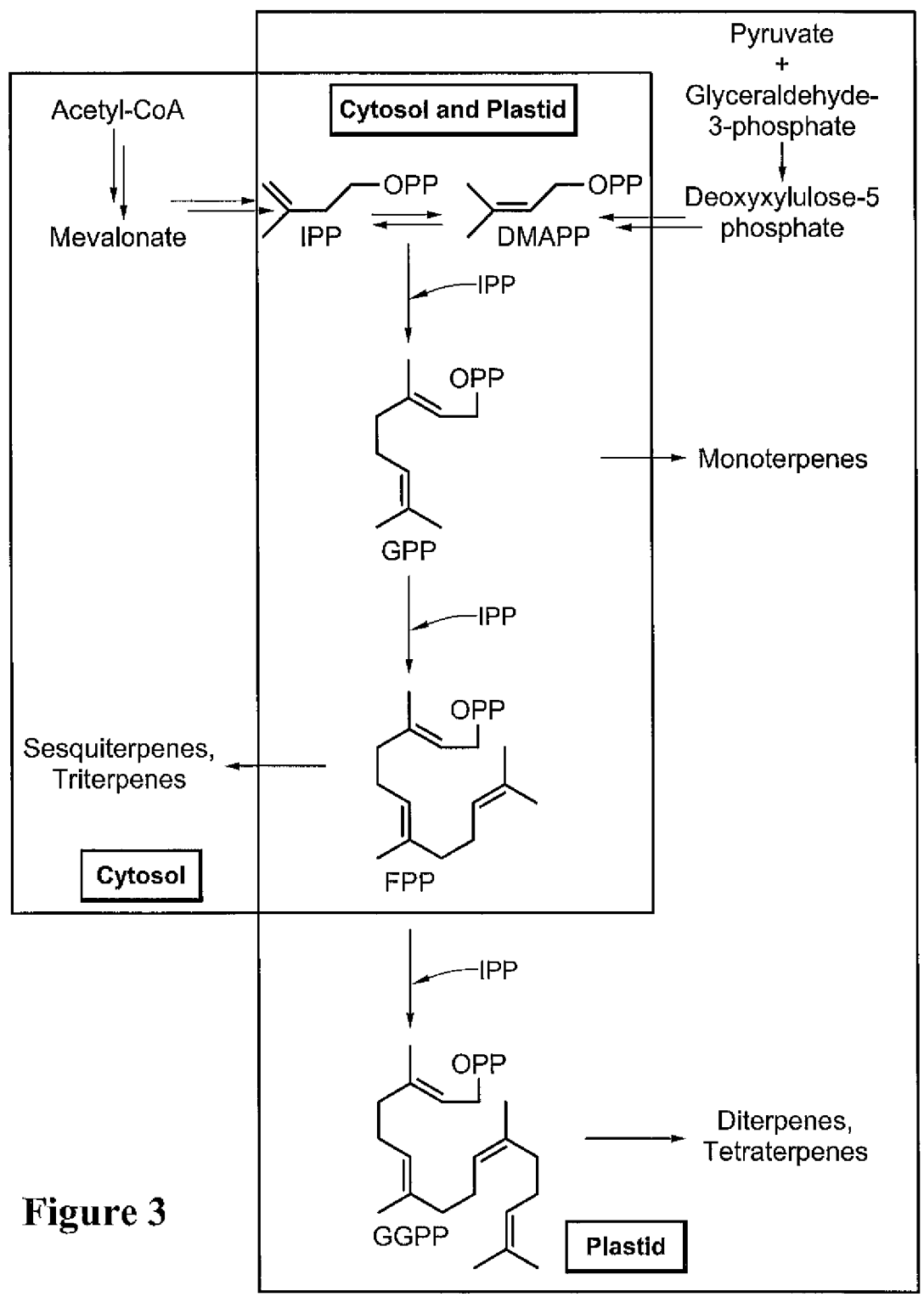
FIG. 3 shows an overview of terpene biosynthesis in photosynthetic eukaryotes.

All terpenoids are derived from isopentenyl disphosphate (FIG. 2). In plants, this central precursor is synthesized in the cytosol via the classical acetate/mevalonate pathway (for example, as described in Qureshi, N. and Porter, J. W. (1981) Conversion of acetyl-Coenzyme A to isopentenyl pyrophosphate, pp. 47-94 in *Biosynthesis of Isoprenoid Compounds*, Vol. 1, edited by J. W. Porter and S. L. Spurgeon, John Wiley & Sons, New York; and Newman, J. D. and Chappell, J. (1999) Crit. Rev. Biochem. Mol. Biol. 34: 95-106), by which the sesquiterpenes (C15) and triterpenes (C30) are formed, and in plastids via the alternative, pyruvate/glyceraldehydes-3-phosphate pathway (for example, as described in Eisenreich, W. M., et al. (1998) Chem. Biol. 5:R221-R233; and Lichtenthaler, H. K. (1999) Annu. Rev. Plant Physiol. Plant Mol. Biol. 50:47-66), by which the monoterpenes (C10), diterpenes (C20), and tetraterpenes (C40) are formed. Following the isomerization of isopentyl disphosphate to dimethylallyl disphosphate, by the action of isopentyl disphosphate isomerase, the latter is condensed with one, two, or three units of isopentenyl disphosphate, by the action of prenyltransferases, to give geranyl disphosphate (C10), farnesyl disphosphate (C15), and geranylgeranyl disphosphate (C20), respectively (for example, as described in Ramos-Valdivia, A. C., et al. (1997) Nat. Prod. Rep. 14:591-603; Ogura, K. and Koyama, T. (1998) Chem. Rev. 98: 1263-1276; Koyama, T. and Ogura, K. (1999) Isopentenyl disphosphate isomerase and prenyltransferases, pp. 69-96 in *Comprehensive Natural Products Chemistry Including Steroids and Cartenoids*, Vol. 2, edited by D. E. Cane, Pergamon, Oxford; and FIG. 2). These three acyclic prenyl disphosphates serve as the immediate precursors of the corresponding monoterpenoid (C10), sequiterpenoid (C15), and diterpenoid (C20) classes, to which they are converted by a very large group of enzymes called the terpene (terpenoid) synthases. These enzymes are often referred to as terpene cyclases, since the products of the reactions are most often cyclic.

A large number of terpenoid synthases of the monoterpene (for example, as described in Croteau, R. (1987) Chem. Rev. 87: 929-954; and Wise, M. I. and Croteau, R. (1999) Monoterpene biosynthesis, pp. 97-153 in *Comprehensive Natural Products Chemistry: Isoprenoids Including Steroids and Carotenoids*, Vol. 2, edited by D. E. Cane, Pergamon, Oxford), sesquiterpene (for example, as described in Cane, D. E. (1990) Isoprenoid biosynthesis: overview, pp. 1-13 in *Comprehensive Natural Products Chemistry: Isoprenoids Including Steroids and Cartenoids*, Vol. 2, edited by D. E. Cane, Pergamon, Oxford; and Cane, D. E. (1999) Sesquiterpene biosynthesis: cyclization mechanisms, pp. 150-200 in *Comprehensive Natural Products Chemistry: Isoprenoids Including Steroids and Cartenoids*, Vol. 2, edited by D. E. Cane, Pergamon, Oxford), and diterpene (for example, as described in West, C. A. (1981) Biosynthesis of diterpenes, pp. 375-411 in *Biosynthesis of Isoprenoid Compounds*, Vol. 1, edited by J. W. Porter and S. L. Spurgeon, John Wiley & Sons, New York; and MacMillan, J. and Beale, M. (1999) Diterpene biosynthesis, pp. 217-243 in *Comprehensive Natural Products Chemistry: Isoprenoids Including Steroids and Carotenoids*, Vol. 2, edited by D. E. Cane, Pergamon, Oxford) series have been isolated from both plant and microbial sources, and these catalysts have been described in detail. All terpenoid synthases are very similar in physical and chemical properties, for example, in requiring a divalent metal ion as the only cofactor for catalysis, and all operate by electrophilic reaction mechanisms. In this regard, the terpenoid synthases resemble the prenyltransferases; however, it is the tremendous range of possible variations in the carbocationic reactions (cyclizations, hydride shifts, rearrangements, and termination steps) catalyzed by the terpenoid synthases that sets them apart as a unique enzyme class. Indeed, it is these variations on a common mechanistic theme that permit the production of essentially all chemically feasible skeletal types, isomers, and derivatives that form the foundation for the great diversity of terpenoid structures.

Several groups have suggested that plant terpene synthases share a common evolutionary origin based upon their similar reaction mechanism and conserved structural and sequence characteristics, including amino acid sequence homology, conserved sequence motifs, intron number, and exon size (for example, as described in Mau, C. J. D. and West, C. A. (1994) Proc. Natl. Acad. Sci. USA 91: 8479-8501; Back, K. and Chappell, J. (1995) J. Biol. Chem. 270:7375-7381; Bohlman, J., et al. (1998) Proc. Natl. Acad. Sci. USA 95: 4126-4133; and Cseke, L., et al. (1998) Mol. Biol. Evol. 15: 1491-1498). A sequence comparison between three isolated plant terpenoid synthase genes (a monoterpene cyclase limonene synthase (Colby, S. M., et al. (1993) J. Biol. Chem. 268: 23016-23024), a sesquiterpene cyclase epi-aristolochene synthase (Facchini, P. J. and Chappell, J. (1992) Proc. Natl. Acad. Sci. USA 89:11088-11092), and a diterpene cyclase casbene synthase (Mau, C. J. D. and West, C. A. (1994) Proc. Natl. Acad. Sci. USA 91: 8479-8501) gave clear indication that these genes, from phylogenetically distant plant species, were related, a conclusion supported by genomic analysis of intron number and location (Mau, C. J. D. and West, C. A. (1994) Proc. Natl. Acad. Sci. USA 91: 8479-8501; Back, K. and Chapell, J. (1995) J. Biol. Chem. 270:7375-7381; Chappell, J. (1995) Plant Physiol. 107:1-6; and Chappell, J. (1995) Annu. Rev. Plant Physiol, Plant Mol, Biol, 46:521-547), Phylogenetic analysis of the deduced amino acid sequences of 33 terpenoid synthases from angiosperms and gymnosperms allowed recognition of six terpenoid synthase (Tps) gene subfamilies on the basis of clades (Bohlmann, J., et al. (1998) Proc. Natl. Acad. Sci. USA 95: 4126-4133). The majority of terpene synthases analyzed produce secondary metabolites and are classified into three subfamilies, Tpsa (sesquiterpene and diterpene synthases from angiosperms), Tpsb (monoterpene synthase from angiosperms of the Lamiaceae), and Tpsd (11 gymnosperm monoterpene, sesquiterpene, and diterpene synthases). The other three subfamrilies, Tpsc, Tpse, and Tpsf are represented by the single angiosperm terpene synthase types copalyl disphosphate synthase, kaurene synthase, and linalool synthase, respectively. The first two are diterpenes synthases involved in early steps of gibberellin biosynthesis (MacMillan, J. and Beale, M. (1999) Diterpene biosynthesis, pp. 217-243 in *Comnprehensive Natural Products Chemistry: Isoprenoids including Steroids and Carotenoids*, Vol. 2, edited by D. E. Cane, Pergamon, Oxford). These two Tps subfamilies are grouped into a single clade and are involved in primary metabolism, which suggests that the bifurcation of terpenoid synthases of primary and secondary metabolism occurred before the separation of angiosperms and gymnosperms (Bohlmann, J. G., et al. (1998) Proc. Natl. Acad. Sci. USA 95: 4126-4133). A detailed analysis of the monoterpene synthase, linalool synthase from Clarkia representing Tpsf, was conducted by Cseke, L., et al. (1998) Mol. Biol. Evol. 15: 1491-1498.

The isolation and analysis of six genomic clones encoding terpene synthases of conifers, ((−)-pinene (C10), (−)-limonene (C10), (E)-α-bisabolene (C15), 6-selinene (C15) and abietadiene synthase (C20) from *Abies grandis* and taxadiene synthase (C20) from *Taxus brevifolia*), all of which are involved in natural products biosynthesis, has been described by Trapp, S. C. and Croteau, R. B., Genetics (2001) 158:811-832. Genome organization (intron number, size, placement and phase, and exon size) of these gymnosperm terpene synthases was compared by Trapp, S. C. and Croteau, R. B. (Genetics (2001) 158:811-832) to eight previously characterized angiosperm terpene synthase genes and to six putative terpene synthase genomic sequences from *Arabidopsis thaliana*. Three distinct classes of terpene synthase genes were discerned, from which assumed patterns of sequential intron loss and the loss of an unusual internal sequence element suggest that the ancestral terpenoid synthase gene resembled a contemporary conifer diterpene synthase gene in containing at least 12 introns and 13 exons of conserved size.

In addition to gene sequences for several angiosperm terpene synthases being able to be found in public databases, see FIG. 11, Trapp, S. C. and Croteau, R. B. (Genetics (2001) 158:811-832) determined the genomic sequences of several terpene synthases from gymnosperms. Trapp, S. C. and Croteau, R. B. (Genetics (2001) 158:811-832) determined the genomic (gDNA) sequences corresponding to six (Agggabi, AgfEαbis, Agg-pin1, Agfδsel1, Agg-lim, Tbggtax) conifer terpene synthase cDNAs (FIG. 11). This selection of genes represents constitutive and inducible terpenoid synthases from each class (monoterpene, sesquiterpene, and diterpene). Sequence alignment of each cDNA with the corresponding gDNA, including putative terpene synthases from *Arabidopsis*, established exon and intron boundaries, exon and intron sizes, and intron placement; generic dicot plant 5'- and 3'-splice site consensus sequences (5' NAG▼GTAAGWWWW; and 3'YAG▼) were used to define specific boundaries (Hanley, B. A. and Schuler, M. A. (1988) Nucleic Acid Res. 16:7159-7176; and Turner, G. (1993) Gene organization in filamentous fungi, pp. 107-125 in The Eukaryotic Genome: Organization and Regulation, edited by P. M. A. Borda, S. Oliver, and P. F. G., SIMS, Cambridge University Press, New York). These analyses reveal a distinct pattern of intron phase for each intron throughout the entire Tps gene family.

A wide range of nomenclatures has been applied to the terpenoid synthases, none of which are systematic. Trapp, S. C. and Croteau, R. B. (Genetics (2001) 158:811-832) uses a unified and specific nomenclature system in which the Latin binomial (two letters), substrate (one- to four-letter abbreviation), and product (three letters) are specified. Thus, ag22, the original cDNA designation for abietadiene synthase from *A. grandis* (a Tpsd subfamily member), becomes AgggABI for the protein and Agggabi for the gene, with the remaining conifer synthases (and other selected genes) described accordingly (for example, as described in FIG. 11).

A key to FIG. 11 is provided below.

Tc, genomic sequences by Trapp, S. C. and Croteau, R. B. (Genetics (2001) 158:811-832); NA, sequences unavailable in the public databases but disclosed in journal reference; pc, sequences obtained by personal communications; ds, sequences in public database by direct submission but not published; p, sequences in database with putative function; c, confirmed gene by experimental determination stated in database; i, two possible isozymes reported for the same region referred to as A1 and A2; —, no former gene name or accession number. Species names are: *Abies grandis, Arabidopsis thaliana, Clarkia concinna, Gossypium arboreum, Hyoscyamus muticus, Mentha longifolia, Mentha spicata, Nicotiana tabacum, Ricinus communis, Perilla frutescens, Taxus brevifolia,* and *Zea mays*.

[a]Former names, respectively, for (2)-copalyl diphosphate synthase and ent-kaurene synthase were ent-kaurene synthase A (KSA) and ent-kaurene synthase B (KSB), and mutant phenotypes were ga1 and ga2; these designations have been used loosely.

[b]Nomenclature architecture is specified as follows. The Latin binomial two-letter abbreviations are in spaces 1 and 2. The substrates (1- to 4-letter abbreviations) are in spaces 3-6, consisting of 1- or 2-letter abbreviations for substrate utilized in boldface (e.g., g, geranyl diphosphate; f, farnesyl diphosphate; gg, geranylgeranyl diphosphate; c, copalyl diphosphate; ch, chrysanthemyl diphosphate; in lowercase) followed by stereochemistry and/or isomer definition (e.g., a, b, d, g, etc. followed by epi (e), E, Z, -, 1, etc.). The 3-letter product abbreviation indicates the major product is an olefin; otherwise the quenching nucleophile is indicated, (e.g., ABI, abietadiene synthase; BORPP, bornyldiphosphate synthase; CEDOH, cedrol synthase); uppercase specifies protein and lowercase specifies cDNA or gDNA. All letters except species names are in italics for cDNA and gene. Distinction between cDNA and gDNA must be stated or a g is added before the abbreviation, e.g., Tbggtax cDNA and gTbggtax, or Tbggtax gene (nomenclature system devised by S. Trapp, E. Davis, J. Crock, and R. Croteau, and as discussed in Trapp, S. C. and Croteau, R. B., Genetics (2001) 158:811-832).

A comparison of genomic structures (as shown in FIGS. 5A, B, and C) indicate that the plant terpene synthase genes consist of three classes based on intron/exon pattern; 12-14 introns (class I), 9 introns (class II), or 6 introns (class III). Using this classification, based on distinctive exon/intron patterns, seven conifer genes that Trapp, S. C. and Croteau, R. B. (Genetics (2001) 158:811-832) studied were assigned to class I or class II. Class I comprises conifer diterpene synthase genes Agggabi and Tbggtax and sesquiterpene synthase Agfabis and angiosperm synthase genes specifically involved in primary metabolism (Atgg-coppl and Ccglinoh). Terpene synthase class I genes contain 11-14 introns and 12-15 of exons of characteristic size, including the CDIS domain comprising exons 4, 5, and 6 and the first approximately 20 amino acids of exon 7, and introns 4, 5, and 6 (this unusual sequence element corresponds to a 215-amino-acid region (Pro 137-Leu 351) of the Agggabi sequence). Class II Tps genes comprise only conifer monoterpene and sesquiterpene synthases, and these contain 9 introns and 10 exons; introns 1 and 2 and the entire CDIS element have been lost, including introns 4, 5 and 6. Class III Tps genes comprise only angiosperm monoterpene, sesquiterpene, and diterpene synthases involved in secondary metabolism, and they contain 6 introns and 7 exons. Introns 1, 2, 7, 9, and 10, and the CDIS domain have been lost in the class III type. The introns of class III Tps genes (introns 3, 8, and 11-14) are conserved among all plant terpene synthase genes and were described as introns 1-6, respectively, in previous analyses (Mau, C. J. D. and West, C. A. (1994) Proc. Natl. Acad. Sci. USA 91: 8479-8501; Back, K. and Chapell, J. (1995) J. Biol. Chem. 270:7375-7381; and Chappell, J. (1995) Annu. Rev. Plant Physiol. Plant Mol. Biol. 46:521-547).

A number of diterpene products may be produced in vivo by inserting a variant gene encoding a diterpene synthase into the chloroplast or nuclear genome of an organism, for example, a microalgae, yeast, or plant. When the functional variant diterpene synthase is expressed by the organism, the variant enzyme will utilize either the endogenous geranylgeranyl diphosphate as a substrate, or if the variant enzyme contains a GGPP synthase domain, will utilize the endogenous IPP and DMAPP as substrates. The variant enzyme will convert the substrates to a diterpene in vivo. Examples of diterpene synthases that may be used in this manner include Abietadiene synthase, Taxadiene synthase, Casbene synthase, and ent-Kaurene synthase.

Figure 5C:
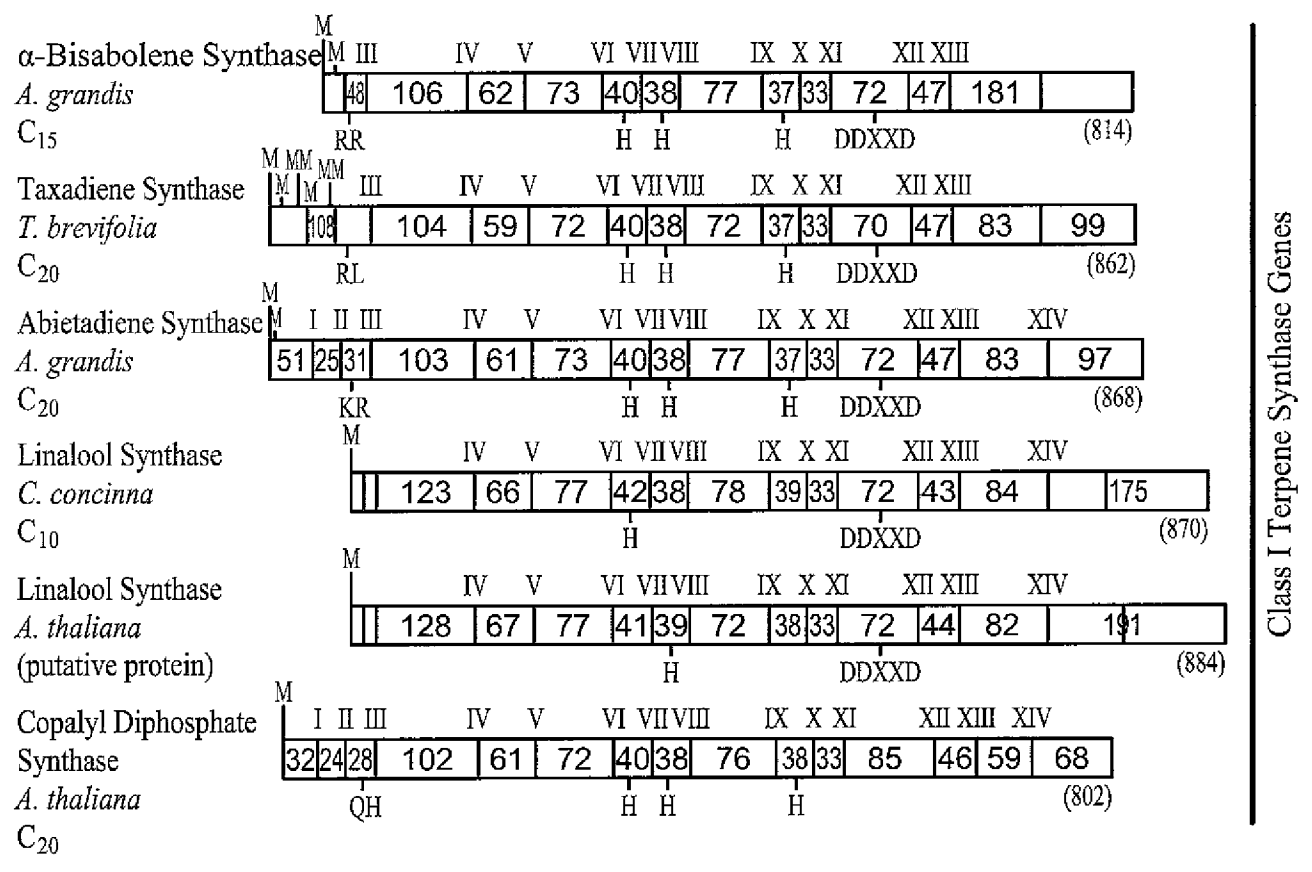

Trapp, S. C., and Croteau R. B, (Genetics 158:811-832 (2001) studied the genomic organization of plant terpene synthase (Tps) genes and the results of their studies are shown in FIGS. 5A, B, and C. Black vertical bars represent introns 1-14 (Roman numerals in figure) and are separated by shaded blocks with specified lengths, representing exons 1-15, The terpenoid synthase genes are divided into three classes (class I, class II, and class III), which appear to have evolved sequentially from class I to class III by intron loss and loss of the conifer diterpene internal sequence domain (CDIS). (FIG. 5C) Class I Tps genes comprise 12-14 introns and 13-15 exons and consist primarily of diterpene synthases found in gymnosperms (secondary metabolism) and angiosperms (primary metabolism). (FIG. 5B) Class II Tps genes comprise 9 introns and 10 exons and consist of only gymnosperm monoterpene and sesquiterpene synthases involved in secondary metabolism. (FIG. 5A) Class III Tps genes comprise 6 introns and 7 exons and consist of angiosperm monoterpene, sesquiterpene, and diterpene synthases involved in secondary metabolism, Exons that are identically shaded illustrate sequential loss of introns and the CDIS domain, over evolutionary time, from class I through class III. The methionine at the translational start site of the coding region (and alternatives), highly conserved histidines, and single or double arginines indicating the minimum mature protein (Williams, D. C., et al. (1998) Biochemistry 37:12213-12220) are represented by M, H, RR, or RX (X representing other amino acids that are sometimes substituted), respectively. The enzymatic classification as a monoterpene, sesquiterpene, or diterpene synthase is represented by C10, C15, C20, respectively, Conifer terpene synthases were isolated and sequenced to determine genomic structure; all other terpene synthase sequences were obtained from public databases or by personal communication (see FIG. 11). Putative terpene synthases are referred to as putative proteins and are illustrated based upon predicted homology. Two different predictions of the same putative protein (accession no, Z97341) are shown as limonene synthase A1 and A2; if A1 is correct, the genomic pattern suggests that Atlim (accession no. Z97341) is a sesquiterpene synthase; if A2 is correct, then Atlim (accession no. Z97341) is a monoterpene synthase. In the analysis of intron borders of the Msg-lim/Mlg-lim chimera and Hmfvet1 genes (see FIG. 11), only a single intron border (5' or 3') was sequenced to determine intron placement; size was not determined. The intron/exon borders predicted for a number of terpene synthases identified in the *Arabidopsis* database were determined to be incorrect; these data were reanalyzed and new predictions used. The number in parentheses represents the deduced size (in amino acid residues) of the corresponding protein or preprotein, as appropriate.

FIG. 11 provides the names of various terpene synthases and provides the GenBank accession numbers for both the cDNA and gDNA of many of the listed terpene synthases. A listing of the articles cited in FIG. 11 is provided below.

The following articles are cited in FIG. 11: Back, K. and Chapell, J. (1995) J. Biol. Chem. 270:7375-7381; Bohlmann, J., et al. (1997) J. Biol. Chem. 272:21784-21792; Bohlmann, J., et al. (1998a) Proc. Natl. Acad. Sci. USA 95:6756-6761; Bohlmann J., et al. 1999) Arch Biochem. Biophys. 368:232-243; Chen, X., et al. (1996) J. Nat. Prod. 59:944-951; Colby, S. M., et al. (1993) J. Biol. Chem. 268:23016-23024; Csekf, L., et al. (1998) Mol. Bio. Evol. 15:1491-1498; Davis, E. M., et al. (1998) Plant Physiol. 116:1192; Facchini, P. 5., and Chappell, J. (1992) Proc. Natl. Acad. Sci. USA 89:11088-11092; Mau, C. J. D. and West, C. A. 1994) Proc. Natl. Acad. Sci. USA 91:8479-8501; Steele, C. L., et al. (1998) J. Biol. Chem. 273:2078-2089; Stofer Vogel, B., et al. (1996) J. Biol. Chem. 271:23262-23268; Sun, T. and Kamiya, Y. (1994) Plant Cell 6:1509-1518; Sun, T. P., et al. (1992) Plant Cell 4:119-128; Wildung, M. R. and Croteau, R. (1996) J. Biol. Chem. 271:9201-9204; Yamaguchi, S., et al. 1998) Plant Physiol. 116:1271-1278; and Yuba, A., et al. (1996) Arch. Biochem. Biophys. 332:280-287.

The contents of FIG. 11 is found below.

TABLE 1

Conifer and other selected terpene synthases

| Products | Species | Terpene synthase name | | | GenBank accession no. | | Reference | | Region on chromosome |
|---|---|---|---|---|---|---|---|---|---|
| | | Former gene | Enzyme | cDNA/genomic | cDNA | gDNA | cDNA | gDNA | |
| Abietadiene | A. grandis | ag22 | AggGABI | Agggabi | U50768 | AF326616 | STOFER VOGEL et al (1996) | Trapp and Croteau[tc] | — |
| (E)-α-Bisaboleae | A. grandis | ag1 | AgfEαBIS | AgfEαbis | AF006195 | AF326515 | BOHLMANN et al (1998a) | Trapp and Croteau[tc] | — |
| (−)-Camphene | A. grandis | ag6 | Agg-CAM | Agg-cam | U87910 | — | BOHLMANN et al (1999) | — | — |
| γ-Humdene | A. grandis | ag5 | Agfγ HUM | Agfγhum | U92267 | — | STEELE et al. (1998) | — | — |
| (−)-Limonene | A. grandis | ag10 | Agg-LIM1 | Agg-lim | AF006193 | AF326618 | BOHLMANN et al (1997) | Trapp and Croteau[tc] | — |
| Myrcene | A. grandis | ag2 | AggMYR | Aggmyr | U87908 | — | BOHLMANN et al (1997) | — | — |
| (−)-α/β-Pinene | A. grandis | ag3 | Agg-PIN1 | Agg-pin1 | U87909 | AF326517 | BOHLMANN et al (1997) | Trapp and Croteau[tc] | — |
| (−)-α-Pinene/(−)-limonene | A. grandis | ag11 | Agg-PIN2 | Agg-pin2 | AF189207 | — | BOHLMANN et al (1999) | — | — |
| (−)-β-Phellandrene | A. grandis | ag8 | Agg-βPHE | Agg-βphe | AfI89205 | — | BOHLMANN et al (1999) | — | — |
| δ-Selinene | A. grandis | ag4 | AgδSEL1 | Agδsel1 | U92266 | AF326513 | STEELE et al. (1998) | Trapp and Croteau[tc] | — |
| | A. grandis | | AgδSEL2 | Agδsel2 | — | AF326514 | — | Trapp and Croteau[tc] | — |
| Taxadiene | T. brevifolia | Tb1 | TbgGTAX | Tbggtax | U48796 | AF326619 | WIRBUNG and CARITEAD (1996) | Trapp and Croteau[tc] | — |
| Terpinolene | A. grandis | ag9 | AggTEO | Aggteo | AF139206 | — | BOHLMASN et al (1999) | — | — |
| 5-epi-Aristolachene | Nicotiana tabacum | TEAS3 | NtfeARI3 | Ntfeari3 | L04680 | L04680 | FACCHINI and CHAPPELL (1992) | FACCHINI and CHAPPELL (1992) | — |
| | | TEAS4 | NtfeARI4 | Ntfeari4 | L04680 | L04680 | | | — |
| 5-epi-Aristolochene[p] | A. thaliana | | AteARI | Ateari | — | AL022224 | — | Bevan et al.[ds] | Chromosome 4 BAC FIC12 (ESSA) nt 44054-38820 |
| δ-Cadinene | G. arboreum | CAD1-A | GafδCAD1A | Gafδcad1a | X96429 | Y18484 | CHEN et al. (1996) | Liang et al.[ds] | — |
| δ-Cadinene | G. hirsulum | CAD1-A | GhfδCAD1 | Ghfδcad1 | U88318 | — | DAVIS et al. (1998) | — | — |
| δ-Cadinene | G. arboreum | gCAD1-B | GafδCAD1b | Gafδcad1b | — | X95323 | — | Chen et al.[ds] | — |
| Cadinene[p] | A. thaliana | | AtCAD | Atcad | — | AL022224 | — | Bevan et al.[ds] | Chromosome 4 BAC FIC12 (ESSA) nt 44054-58820 |
| Casbene | Riciaus cummunis | cas | RcggCAS | Rcggcas | L32134 | NA | MAU and WEST (1994) | West[pc] | — |
| (−)-Copalyl diphosphate[a] | A. thaliana | GA1 | Atgg-COPP1 | Atgg-copp1 | U11034 | NA | SUN and KAMIYA (1994) | Sun et al. (1992) | Chromosome 4 (Top) BAC T5J8 nt 34971-41856 |
| ent-Kaurene[a] | A. thaliana | GA2 | Argg-KAU | Argg-kau | AF034774 | AC004044[p] | YAMAGUCHI et al. (1996) | Bastide et al[ds, c] Vysotssain et al[ds, c] | Chromosome 1 BAC T8K14 nt 43552-47420 |
| (−)-Limonene | Pessila frulescens | PFLC1 | Pfg-LIM1 | Pfg-lim1 | D49368 | AC007202 | YUBA et al. (1996) | Tsubouchi[pc] | — |
| (−)-Limonene | Mentha spicala | LMS | Msg-LIM | Msg-lim | L13459 | AB005744 | COLBY et al. (1998) | — | — |
| (−)-Limonene | M. longifidia | LMS | Mlg-LIM | Mlg-lim | AF175323 | — | Crock and Croteau[ds, c] | Jones and Davis[pc] | — |
| Limonene[a, i] | A. thaliana | | AtLIMA1 | Atlima1 | — | — | — | Bevan et al.[pc] | Chromosome 4 CF6 (ESSA 1) nt 164983-170505 |
| | A. thaliana | | AtLIMA2 | Atlima2 | — | — | — | — | — |
| Limonene[p] | A. thaliana | | AtLIMB | Atlimb | — | Z97341 | — | Bevan et al | Chromosome 4 CF5 (ESSA 1) nt 172598-175344 |
| (S)-Linalool | Chakia concinna | LIS | CcgLINOH | Ccglinoh | U20187 | AF067662 | CSEKE et al. (1996) | Cacke et al (1998) | Chromosome 1 BAC FHP17 nt 73996-78905 |
| Linalool[p] | A. thaliana | | AtgLINOH | Atglinoh | — | AC02294 | — | Federspiel | — |
| Vetispiradiene | Hyoscyamus muticus | Chimera | HmfVET | Hmfvet | U20187 | NA | BACK and CHAPPELL (1995) | Chappell[pc] | — |
| Vetispiradiene[p] | A. thaliana | | AtVET | Atvet | — | AL022224 | — | Bevan et al.[ds] | Chromosome 4 BAC F12C12 (ESSA) nt 54692-56893 |

TABLE 1-continued

Conifer and other selected terpene synthases

| Products | Terpene synthase name | | | GenBank accession no. | | | Reference | |
|---|---|---|---|---|---|---|---|---|
| | Species | Former gene | Enzyme | cDNA/genomic | cDNA | gDNA | cDNA | gDNA | Region on chromosome | tc, genomic sequences by Trapp and Croteau (accession nos. pending);
NA, sequences unavailable in the public databases but disclosed in journal reference;
pc, sequences obtained by personal communications;
ds, sequences in public database by direct submission but not published;
p, sequences in database with putative function;
c, confirmed gene by experimental determination stated in database;
i, two possible isozymes reported for the same region referred to as A1 and A2;
—, no former gene name or accession number.
Species names are: *Abies grandis, Arabidopsis thaliana, Clarkia concinna, Gossypium arboreum, Hyascyamus muticus, Mentha longifolia, Mentha spicata, Nicotiana tabacum, Hicinus communis, Perilla frutescens, Taxus brevifoba, Zea mays.*
Former names, respectively, for (−)-copalyl diphosphate synthase and ent-kaurene synthase were ent-kaurene synthase A (KSA) and ent-kaurene synthase B (KSB), and mutant phenotypes were ga1 and ga2; these designations have been used loosely.
Nomenclature architecture is specified as follows. The Latin binomial two-letter abbreviations are in spaces 1 and 2. The substrates (1- to 4-letter abbrev.) are in spaces 3-6, consisting of 1- or 2-letter abbrev. for substrate utilized in boldface (e.g., g, geranyl diphosphate; f, farnesyl diphosphate; gg, geranylgeranyl diphosphate; c, copalyl diphosphate; ch, chrysanthemyl diphosphate; in lowercase) followed by stereochemistry and/or isomer definition (e.g., α, $\alpha_t$ β, δ, γ, etc. followed by epi (e), E, Z, −, +, etc.).
The 3-letter product abbrev, indicates the major product is an olefin; otherwise the quenching nucleophile is indicated, (e.g., ABI, abietadiene synthase; BORPP, bornyl diphosphate synthase; CEDOH, cedrol synthase);
uppercase specifies protein and lowercase specifies cDNA or gDNA.
All letters except species names are in italics for cDNA and gene.
Distinction between cDNA and gDNA must be stated or a g is added before the abbreviation, e.g., Tbggtax cDNA and gTbggtax or Tbggtax gene (nomenclature) system devised by S. Trapp, E. Davis, J. Crock, and R. Croteau).

In addition to the terpene synthases in FIG. 11, additional exemplary terpene synthases include Bisobolene synthase, (−)-Pinene synthase, δ-Selinene synthase, (+Limonene synthase, Abeitadiene synthase, and Taxadiene synthase.

Examples of synthases include, but are not limited to, botryococcene synthase, limonene synthase, 1,8 cineole synthase, α-pinene synthase, camphene synthase, (+)-sabinene synthase, myrcene synthase, abietadiene synthase, taxadiene synthase, farnesyl pyrophosphate synthase, amorphadiene synthase, (E)-α-bisabolene synthase, diapophytoene synthase, and diapophytoene desaturase. Additional examples of enzymes useful in the disclosed embodiments are described in Table 2.

TABLE 2

Examples of Enzymes Involved in the Isoprenoid Pathway

| Enzyme | Source | NCBI protein ID |
|---|---|---|
| Limonene | M. spicata | 2ONH_A |
| Cineole | S. officinalis | AAC26016 |
| Pinene | A. grandis | AAK83564 |
| Camphene | A. grandis | AAB70707 |
| Sabinene | S. officinalis | AAC26018 |
| Myrcene | A. grandis | AAB71084 |
| Abietadiene | A. grandis | Q38710 |
| Taxadiene | T. brevifolia | AAK83566 |
| FPP (IS-9) | G. gallus | P08836 |
| Amorphadiene | A. annua | AAF61439 |
| Bisabolene | A. grandis | O81086 |
| Diapophytoene | S. aureus | |
| Diapophytoene desaturase | S. aureus | |
| GPPS-LSU | M. spicata | AAF08793 |
| GPPS-SSU | M. spicata | AAF08792 |
| GPPS | A. thaliana | CAC16849 |
| GPPS | C. reinhardtii | EDP05515 |
| FPP | E. coli | NP_414955 |
| FPP | A. thaliana | NP_199588 |
| FPP | A. thaliana | NP_93452 |
| FPP | C. reinhardtii | EDP03194 |
| Limonene | L. angustifolia | ABB73044 |
| Monoterpene | S. lycopersicum | AAX69064 |
| Terpinolene | O. basilicum | AAV63792 |
| Myrcene | O. basilicum | AAV63791 |
| Zingiberene | O. basilicum | AAV63788 |
| Myrcene | Q. ilex | CAC41012 |
| Myrcene | P. abies | AAS47696 |
| Myrcene, ocimene | A. thaliana | NP_179998 |
| Myrcene, ocimene | A. thaliana | NP_567511 |
| Sesquiterpene | Z. mays; B73 | AAS88571 |
| Sesquiterpene | A. thaliana | NP_199276 |
| Sesquiterpene | A. thaliana | NP_193064 |
| Sesquiterpene | A. thaliana | NP_193066 |
| Curcumene | P. cablin | AAS86319 |
| Farnesene | M. domestica | AAX19772 |
| Farnesene | C. sativus | AAU05951 |
| Farnesene | C. junos | AAK54279 |
| Farnesene | P. abies | AAS47697 |
| Bisabolene | P. abies | AAS47689 |
| Sesquiterpene | A. thaliana | NP_197784 |
| Sesquiterpene | A. thaliana | NP_175313 |
| GPP Chimera | | |
| GPPS-LSU + SSU fusion | | |
| Geranylgeranyl reductase | A. thaliana | NP_177587 |
| Geranylgeranyl reductase | C. reinhardtii | EDP09986 |
| FPP A118W | G. gallus | |
| IPP isomerase | E. coli | NP_417365 |
| IPP isomerase | H. pluvialis | ABB80114 |
| NON protein ID | | |
| Chlorophyllidohydrolase | C. reinhardtii | EDP01364 |
| Chlorophyllidohydrolase | A. thaliana | NP_564094 |
| Chlorophyllidohydrolase | A. thaliana | NP_199199 |
| Phosphatase | S. cerevisiac | AAB64930 |
| GGPP domain of fusicoccadiene synthase | P. agmygdali | BAF45925 |
| Cyclase domain of fusicoccadiene synthase | P. agmygdali | BAF45925 |
| Casbene synthase | R. communis | EEF48772 |
| Chimeric Artemisia chrysanthemyl/ farnesyl diphosphase synthase | | |

The synthase may also be β-caryophyllene synthase, germacrene A synthase, 8-epicedrol synthase, valencene synthase, (+)-δ-cadinene synthase, germacrene C synthase, (E)-β-farnesene synthase, casbene synthase, vetispiradiene synthase, 5-epi-aristolochene synthase, aristolchene synthase, α-humulene, (E,E)-α-farnesene synthase, (−)-β-pinene synthase, limonene cyclase, linalool synthase, (+)-bornyl diphosphate synthase, levopimaradiene synthase, isopimaradiene synthase, (E)-γ-bisabolene synthase, copalyl pyrophosphate synthase, kaurene synthase, longifolene synthase, γ-humulene synthase, δ-selinene synthase, β-phellandrene synthase, terpinolene synthase, (+)-3-carene synthase, syn-copalyl diphosphate synthase, α-terpineol synthase, syn-pimara-7,15-diene synthase, ent-sandaaracopimaradiene synthase, sterner-13-ene synthase, E-β-ocimene, S-linalool synthase, geraniol synthase, γ-terpinene synthase, linalool synthase, E-β-ocimene synthase, epi-cedrol synthase, α-zingiberene synthase, guaiadiene synthase, cascarilladiene synthase, cis-muuroladiene synthase, aphidicolan-16b-ol synthase, elizabethatriene synthase, sandalol synthase, patchoulol synthase, zinzanol synthase, cedrol synthase, scareol synthase, copalol synthase, manool synthase, botryococcene synthase, or germacrene A synthase. Additionally, the multiple sequence alignment of several isoprenoid synthesis enzymes is shown in FIG. 6.

An isoprenoid synthase enzyme catalyzes a cyclizing enzymatic reaction using a polyprenyl diphosphate as substrate. Polyprenyl diphosphate substrates that can serve as a substrate for a variant isoprenoid synthase include, but are not limited to, geranyl diphosphate (GPP), farnesyl diphosphate (FPP), geranylgeranyl diphosphate (GGPP), hexaprenyl diphosphate (HexPP), heptaprenyl diphosphate (HepPP), octaprenyl diphosphate (OPP), solanesyl diphosphate (SPP), decaprenyl diphosphate (DPP), nonaprenyl diphosphate (NPP), and undecaprenyl diphosphate (UPP). In some embodiments, the substrate of a variant isoprenoid synthase is GPP. In other embodiments, the substrate of a variant isoprenoid synthase is FPP. In other embodiments, the substrate of a variant isoprenoid synthase is GGPP. Examples of isoprenoid synthase enzymes include the monoterpene, sesquiterpene, and diterpene synthases.

Exemplary diterpene synthases are fusicoccadiene synthase, kaurene synthase, casbene synthase, taxadiene synthase, abietadiene synthase, or a homolog of any one of the above, or a chimera of any one of the above. Addition diterepene synthases are fusicoccadiene synthase or a homolog of a fusicoccadiene synthase.

In some embodiments, a variant isoprenoid synthase provides for production of an isoprenoid product at a level that is at least about 5%, at least about 10%, at least about 15%, at least about 20%, at least about 25%, at least about 50%, at least about 75%, or at least about 90% greater than the level produced by a parent isoprenoid synthase under similar conditions. In some embodiments, a variant isoprenoid synthase provides for production of an isoprenoid at a level that is at least about two-fold, at least about 2.5-fold, at least about 5-fold, at least about 7.5-fold, at least about 10-fold, at least about 25-fold, at least about 50-fold, or at least about 100-fold greater than the level produced by a parent isoprenoid synthase under similar conditions.

A variant isoprenoid synthase can comprise any one of the amino acid sequences encoding a synthase as set forth, for example, in Table 2 (for example, FPP synthase from *G. gallus*), or can comprise any one of the amino acid sequences encoding a synthase as set forth in Table 2, with at least one amino acid substitution. In some embodiments, a variant isoprenoid synthase can comprise an amino acid sequence comprising from one amino acid substitution to about 50 amino acid substitutions compared to any one of the amino acid sequences encoding a synthase as set forth in Table 2. In some embodiments, a variant isoprenoid synthase comprises at least one, at least two, at least three, at least four, at least five, at least six, at least seven, at least eight, at least nine, or at least 10 amino acid substitutions, from about 10 amino acid substitutions to about 12 amino acid substitutions, from about 12 amino acid substitutions to about 15 amino acid substitutions, from about 15 amino acid substitutions to about 20 amino acid substitutions, from about 20 amino acid substitutions to about 25 amino acid substitutions, or from about 25 amino acid substitutions to about 50 amino acid substitutions, as compared to any one of the amino acid sequences encoding a synthase as set forth in Table 2 (for example, limonene synthase).

Codon Biased or Codon Optimized Variant Polynucleotides

One or more codons of a polynucleotide can be biased or optimized to reflect chloroplast codon usage or nuclear codon usage. Most amino acids are encoded by two or more different (degenerate) codons, and it is well recognized that various organisms utilize certain codons in preference to others.

Such preferential codon usage, which also is utilized in chloroplasts, is referred to herein as "chloroplast codon usage," Table 3 (below) shows the chloroplast codon usage for *C. reinhardtii* (see U.S. Patent Application Publication No.: 2004/0014174, published Jan. 22, 2004).

TABLE 3

Chloroplast Codon Usage in *Chlamydomonas reinhardtii*

| | | | |
|---|---|---|---|
| UUU 34.1*(348**) | UCU 19.4(198) | UAU 23.7(242) | UGU 8.5(87) |
| UUC 14.2(145) | UCC 4.9(50) | UAC 10.4(106) | UGC 2.6(27) |
| UUA 72.8(742) | UCA 20.4(208) | UAA 2.7(28) | UGA 0.1(1) |
| UUG 5.6(57) | UCG 5.2(53) | UAG 0.7(7) | UGG 13.7(140) |
| CUU 14.8(151) | CCU 14.9(152) | CAU 11.1(113) | CGU 25.5(260) |
| CUC 1.0(10) | CCC 5.4(55) | CAC 8.4(86) | CGC 5.1(52) |
| CUA 6.8(69) | CCA 19.3(197) | CAA 34.8(355) | CGA 3.8(39) |
| CUG 7.2(73) | CCG 3.0(31) | GAG 5.4(55) | CGG 0.5(5) |
| AUU 44.6(455) | ACU 23.3(237) | AAU 44.0(449) | AGU 16.9(172) |
| AUC 9.7(99) | ACC 7.8(80) | AAC 19.7(201) | AGC 6.7(68) |
| AUA 8.2(84) | ACA 29.3(299) | AAA 61.5(627) | AGA 5.0(51) |
| AUG 23.3(238) | ACG 4.2(43) | AAG 11.0(112) | AGG 1.5(15) |
| GUU 27.5(280) | GCU 30.6(312) | GAU 23.8(243) | GGU 40.0(408) |
| GUC 4.6(47) | GCC 11.1(113) | GAC 11.6(118) | GGC 8.7(89) |
| GUA 26.4(269) | GCA 19.9(203) | GAA 40.3(411) | CGA 9.6(98) |
| GUG 7.1(72) | GCG 4.3(44) | GAG 6.9(70) | GGG 4.3(44) |

*Frequency of codon usage per 1,000 codons.
**Number of times observed in 36 chloroplast coding sequences (10,193 codons).

The term "biased" or "optimized", when used in reference to a codon, means that the sequence of a codon in a polynucleotide has been changed such that the codon is one that is used preferentially in, for example, the chloroplasts of the organism (see Table 3), or the nuclear genome of the organism (see Table 4). "Biased" or codon "optimized" can be used interchangeably throughout the specification.

A polynucleotide that is biased for chloroplast or nuclear codon usage can be synthesized de novo, or can be genetically modified using routine recombinant DNA techniques, for example, by a site-directed mutagenesis method, to change one or more codons.

Table 3 exemplifies codons that are preferentially used in algal chloroplast genes. The term "chloroplast codon usage" is used herein to refer to such codons, and is used in a comparative sense with respect to degenerate codons that encode the same amino acid but are less likely to be found as a codon in a chloroplast gene. The term "biased", when used in reference to chloroplast codon usage, refers to the manipulation of a polynucleotide such that one or more nucleotides of one or more codons is changed, resulting in a codon that is preferentially used in chloroplasts. Chloroplast codon bias is exemplified herein by the alga chloroplast codon bias as set forth in Table 3. The chloroplast codon bias can, but need not, be selected based on a particular plant in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect chloroplast codon usage, or can be the de novo synthesis of polynucleotide sequence such that the change (bias) is introduced as a consequence of the synthesis procedure.

In addition to utilizing chloroplast codon bias as a means to provide efficient translation of a polypeptide, it will be recognized that an alternative means for obtaining efficient translation of a polypeptide in a chloroplast is to re-engineer the chloroplast genome (e.g., a *C. reinhardtii* chloroplast genome) for the expression of tRNAs not otherwise expressed in the chloroplast genome. Such an engineered algae expressing one or more exogenous tRNA molecules provides the advantage that it would obviate a requirement to modify every polynucleotide of interest that is to be introduced into and expressed from a chloroplast genome; instead, algae such as *C. reinhardtii* that comprise a genetically modified chloroplast genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 1996; Duret, Trends Genet. 16:287-289, 2000; Goldman et, al., J. Mol. Biol. 245:467-473, 1995; and Komar et. al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into chloroplasts to complement rare or unused tRNA genes in a chloroplast genome, such as a *C. reinhardtii* chloroplast genome.

Generally, the chloroplast codon bias selected for purposes of the present disclosure, including, for example, in preparing a synthetic polynucleotide as disclosed herein reflects chloroplast codon usage of a plant chloroplast, and includes a codon bias that, with respect to the third position of a codon, is skewed towards A/T, for example, where the third position has greater than about 66% AT bias, or greater than about 70% AT bias. In one embodiment, the chloroplast codon usage is biased to reflect alga chloroplast codon usage, for example, *C. reinhardtii*, which has about 74.6% AT bias in the third codon position.

Table 4 exemplifies codons that are preferentially used in algal nuclear genes. The term "nuclear codon usage" is used herein to refer to such codons, and is used in a comparative sense with respect to degenerate codons that encode the same amino acid but are less likely to be found as a codon in a nuclear gene. The term "biased", when used in reference to nuclear codon usage, refers to the manipulation of a polynucleotide such that one or more nucleotides of one or more codons is changed, resulting in a codon that is preferentially used in the nucleus. Nuclear codon bias is exemplified herein by the alga nuclear codon bias as set forth in Table 4. The nuclear codon bias can, but need not, be selected based on a particular host in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect nuclear codon usage, or can be the de novo synthesis of polynucleotide sequence such that the change (bias) is introduced as a consequence of the synthesis procedure.

In addition to utilizing nuclear codon bias as a means to provide efficient translation of a polypeptide, it will be recognized that an alternative means for obtaining efficient translation of a polypeptide in a nucleus is to re-engineer the nuclear genome (e.g., a C. reinhardtii nuclear genome) for the expression of tRNAs not otherwise expressed in the nuclear genome. Such an engineered algae expressing one or more exogenous tRNA molecules provides the advantage that it would obviate a requirement to modify every polynucleotide of interest that is to be introduced into and expressed from a nuclear genome; instead, algae such as C. reinhardtii that comprise a genetically modified nuclear genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 1996; Duret, Trends Genet. 16:287-289, 2000; Goldman et. al., J. Mol. Biol. 245:467-473, 1995; and Komar et. al., Biol. Chem. 379:1295-1300, 1998). In E. coli, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into the nucleus to complement rare or unused tRNA genes in a nuclear genome, such as a C. reinhardtii nuclear genome.

Generally, the nuclear codon bias selected for purposes of the present disclosure, including, for example, in preparing a synthetic polynucleotide as disclosed herein, can reflect nuclear codon usage of an algal nucleus and includes a codon bias that results in the coding sequence containing greater than 60% G/C content.

TABLE 4

Nuclear Codon Usage in *Chlamydomonas reinhardtii*
fields: [triplets] [frequency: per thousand] ([number])

| | | | |
|---|---|---|---|
| UUU 5.0(2110) | UCU 4.7(1992) | UAU 2.6(1085) | UGU 1.4(601) |
| UUC 27.1(11411) | UCC 16.1(6782) | UAC 22.8(9579) | UGC 13.1(5498) |
| UUA 0.6(247) | UCA 3.2(1348) | UAA 1.0(441) | UGA 0.5(227) |
| UUG 4.0(1673) | UCG 16.1(6763) | UAG 0.4(183) | UGG 13.2(5559) |
| CUU 4.4(1869) | CCU 8.1(3416) | CAU 2.2(919) | CGU 4.9(2071) |
| CUC 13.0(5480) | CCC 29.5(12409) | CAC 17.2(7252) | CGC 34.9(14676) |
| CUA 2.6(1086) | CCA 5.1(2124) | CAA 4.2(1780) | CGA 2.0(841) |
| CUG 65.2(27420) | CCG 20.7(8684) | CAG 36.3(15283) | CGG 11.2(4711) |
| AUU 8.0(3360) | ACU (2171) | AAU 2.8(1157) | AGU 2.6(1089) |
| AUC 26.6(11200) | ACC 27.7(11663) | AAC 28.5(11977) | AGC 22.8(9590) |
| AUA 1.1(443) | ACA 4.1(1713) | AAA 2.4(1028) | AGA 0.7(287) |
| AUG 25.7(10796) | ACG 15.9(6684) | AAG 43.3(18212) | AGG 2.7(1150) |
| GUU 5.1(2158) | GCU 16.7(7030) | GAU 6.7(2805) | GGU 9.5(3984) |
| GUC 15.4(6496) | GCC 54.6(22960) | GAC 41.7(17519) | GGC 62.0(26064) |
| GUA 2.0(857) | GCA 10.6(4467) | GAA 2.8(1172) | GGA 5.0(2084) |
| GUG 46.5(19558) | GCG 44.4(18688) | GAG 53.5(22486) | GGG 9.7(4087) |

Coding GC 66.30% 1st letter GC 64.80% 2nd letter GC 47.90% 3rd letter GC 86.21%

Generating Variant Polypeptides

The present disclosure provides methods for generating a variant polypeptide that has one or more altered properties compared to a parent polypeptide. Various methods may be used to generate a variant polypeptide, for example, a variant prenyl transferase or a variant isoprenoid synthase. In other embodiments, variant enzymes are generated, for example, by look-through mutagenesis, walk-through mutagenesis, gene shuffling, directed evolution and/or sexual PCR. These methods allow for the generation, for example, of variant polypeptides containing random sequence(s), variant polypeptides made using predetermined modifications of particular residues, variant polypeptides that utilize evolutionary traits from different genes and variant polypeptides that combine characteristics/functions of different parent genes.

Walk-Through Mutagenesis

The method of walk-through mutagenesis comprises introducing a predetermined amino acid into each and every position in a predefined region (or several different regions) of the amino acid sequence of a parent polypeptide. A protein library is generated which contains mutant proteins having the predetermined amino acid in one or more positions in the region and, collectively, in every position in the region. The method can be referred to as "walk-through" mutagenesis (WTM) because, in effect, a single, predetermined amino acid is substituted position-by-position throughout a defined region of a protein. This allows for a systematic evaluation of the role of a specific amino acid in the structure or function of a protein. WTM is further described in greater detail in U.S. Pat. Nos. 6,649,340, 5,830,650, and 5,798,208, which are hereby incorporated by reference in its entirety.

The library of mutant proteins can be generated by synthesizing a single mixture of oligonucleotides which encodes all of the designed variations of the amino acid sequence for the region containing the predetermined amino acid or amino acids. The total set of designed variations can be made in several mixtures (libraries) that taken together contain all of the designed variations. This mixture of oligonucleotides is synthesized by incorporating in each condensation step of the synthesis both the nucleotide of the sequence to be mutagenized (for example, the wild type or parent sequence) and the nucleotide required for the codon of the predetermined amino acid. Where a nucleotide of the sequence to be mutagenized is the same as a nucleotide for the predetermined amino acid, no additional nucleotide is added.

The mixture of oligonucleotides is inserted into a gene encoding the parent polypeptide to be mutagenized in place of the DNA encoding the region. The variant genes are cloned in a suitable expression vector to provide an expression library of variant polypeptides that can be screened for a subset of variant polypeptides that have altered properties. The library of variant polypeptides produced by this oligonucleotide-mediated procedure contains a larger ratio of informative mutants (those containing the predetermined amino acid in the defined region) relative to noninformative mutants than libraries produced by methods of saturation mutagenesis.

This method provides a systematic and practical approach for evaluating the importance of a particular amino acid or amino acids, and the importance of an amino acid position or positions within a defined region of a polypeptide, and comparing the results to the structure and/or function of the polypeptide. This method is also useful for producing variant polypeptides. The method begins with the assumption that a certain, predetermined amino acid is important to a particular structure and/or function. The assumption can be based upon, for example, what is known about the amino acid from the study of other proteins. For example, the amino acid can be one which has a role in catalysis, binding or another biological function.

With selection of the predetermined amino acid, a library of variant polypeptides to be studied is generated by incorporating the predetermined amino acid into each and every position of a chosen region of a protein. The amino acid is substituted in or "walked-through", for example, in all (or essentially all) positions of the region. For example, within an FPP synthase gene (IS-9), amino acid substitutions or walk-throughs can be in the regions of residues 97-137. 175-198 or 250-290, regions known to be involved in substrate binding and/or involved in catalysis.

The library of variant polypeptides contains individual proteins which have the predetermined amino acid in each and every position in the region. The polypeptide library will have a higher proportion of variants that contain the predetermined amino acid in the region (relative to variants that do not), as compared to libraries that would be generated by completely random mutation, such as saturation mutation. Thus, the desired types of variant are concentrated in the library. This is important because it allows more and larger regions of polypeptides to be mutagenized by the walk-through process, while still yielding libraries of a size which can be screened. Further, if the initial assumption is correct and the amino acid is important to the structure and/or function of the polypeptide, then the library will have a higher proportion of informative variants than a library generated by random mutation.

In another embodiment of walk-through mutagenesis, a predetermined amino acid is introduced into each of certain selected positions within a predefined region or regions. Certain selected positions may be known or thought to be more promising due to structural constraints. Such considerations, based on structural information or modeling of the molecule mutagenized and/or the desired structure, can be used to select a subset of positions within a region or regions for mutagenesis. Thus, the amino acids mutagenized within a region need not be contiguous. Walking an amino acid through certain selected positions in a region can minimize the number of variants produced.

The size of a library will vary depending upon the length and number of regions and amino acids within a region that are mutagenized. The library can be designed, for example, to contain less than $10^{10}$ mutants, or less than $10^9$ mutants. The library can be designed, for example, to contain less than $10^8$ mutants, or less than $10^7$ mutants, or less than $10^6$ mutants or less than $10^5$ mutants.

The amino acid chosen for the "walk through" mutagenesis is generally selected from those known or thought to be involved in the structure and/or function of a protein of interest. The twenty naturally occurring amino acids differ only with respect to their side chains. Each side chain is responsible for chemical properties that make each amino acid unique. Depending on the use, however, a polypeptide also can contain amino acid analogs, including non-naturally occurring synthetic amino acids or modified naturally occurring amino acids. Amino acid analogs are well known in the art (for example, as described in Principles of Protein Structure, 1988, by G. E. Schulz and R. M. Schirner, Springer-Verlag).

A select number of natural amino acids can be located in catalytic sites or proposed catalytic sites of a polypeptide. These amino acids, for example, belong to the group of polar and neutral amino acids such as Ser, Thr, Asn, Gln, Tyr, and Cys; the group of charged amino acids, Asp and Glu, Lys and Arg; and the amino acid His.

Examples of polar and neutral side chains are those of Cys, Ser, Thr, Asn, Gln and Tyr. Gly is also considered to be a borderline member of this group. Ser and Thr play an important role in forming hydrogen-bonds. One additional characteristic of Thr is that the methyl group adds stearic bulk and a slight hydrophobicity, in comparison to the pure hydrophilic side chain of Ser. The acid amide Gln and Asn can also form hydrogen bonds, the amido groups function as hydrogen donors and the carbonyl groups function as hydrogen acceptors. Gln has one more $CH_2$ group than Asn which renders the polar group more flexible and reduces its interaction with the main chain. The side chain of Tyr contains both a hydrophobic, aromatic functionality as well as the ability to act both as a hydrogen bond donor and acceptor.

Histidine (His) has a heterocyclic aromatic side chain with a pK value of 6.0. In the physiological pH range, its imidazole ring can be either uncharged or charged, after taking up a hydrogen ion from solution. Since these two states are readily available, His is quite suitable for catalyzing chemical reactions. It is found in most of the active centers of polypeptide enzymes.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a polypeptide enzyme.

In addition, Lys and Arg are found at the surface of polypeptide enzymes. They have long and flexible side chains. Wobbling in a surrounding solution, they increase the solubility of the protein globule. Lys and Arg are capable of taking part in forming internal salt bridges, or they can help in catalysis. Because of their exposure at the surface of a protein, Lys is a residue more frequently attacked by enzymes which either modify the side chain or cleave the peptide chain at the carbonyl end of Lys residues.

For the purpose of introducing catalytically important amino acids into a polypeptide variant, the disclosure relates to mutagenesis of a parent polypeptide in which a predetermined amino acid in the parent polypeptide is replaced with, for example, one of the following group of amino acids: Ser, Thr, Asn, Gln, Tyr, Cys, His, Glu, Asp, Lys, and Arg, However, for the purpose of altering binding or creating new binding affinities, any of the twenty naturally occurring amino acids can be selected. Alternatively, non-natural amino acids may be substituted as well. In addition, more than one predetermined amino acid in the parent polypeptide can be replaced.

In one embodiment, a variant polypeptide is produced having at least 1%, at least 2%, at least 3%, at least 4%, at least 55%, at least 10, at least 15%, at least 20/, at least 25% or greater increase in any one of the following group of amino acids: Ser, Thr, Asn, Gln, Tyr, Cys, His, Glu, Asp, Lys, and Arg, when compared to the parent polypeptide.

For the libraries described above, whether in the form of polynucleotides and/or corresponding polypeptides, it is understood that the libraries may be attached to a solid support, such as a microchip or a bead, and arrayed, using art recognized techniques.

Importantly, several different regions or domains of a protein can be mutagenized simultaneously. The same or a different amino acid can be "walked-through" each region. This enables the evaluation of amino acid substitutions in conformationally related regions such as, for example, the regions which, upon folding of the protein, are associated to make up a functional site such as the catalytic site of an enzyme. This method provides a way to create modified or completely new catalytic sites in a protein.

Look-Through Mutagenesis (LTM)

LTM comprises introducing a predetermined amino acid into a selected set of positions within a defined region (or several different regions) of the amino acid sequence of a parent polypeptide. The method is meant to provide a comprehensive optimization map, by making replacements using representative amino acids for each of the side-chain chemistry groups of the natural amino acids. In one embodiment, wild-type residues are systematically substituted by one of nine selected amino acids. Mutated polypeptides can be combined to generate combinatorial mutations. In this way, a data set is generated where multiple wild-type amino acids within a polypeptide are mutated. The data set is much smaller than if each amino acid were substituted by each of the 20 natural amino acids (and possible additional other amino acids) and as such can be more easily screened for variant polypeptides containing desirable mutations. This method maintains the basic premise that certain amino acids play a crucial role in the structure and function of a polypeptide. Thus, LTM allows one to "look-through" the structural and/or functional consequences of separately substituting a predetermined amino acid at each functional amino acid position within a defined region of the polypeptide, thereby segregating a specific protein chemistry to the defined region without any interference or "noise" from the generation of unwanted polypeptide analogs (for example, analogs containing amino acid substitutions other than those that follow the LTM scheme). LTM is further described in greater detail in US Patent Publication No. U.S. 2008/0214406, which is hereby incorporated by reference in its entirety.

With LTM, a defined region or regions within a parent or wild type polypeptide are selected for mutagenesis. Typically, the regions are believed to be important to the polypeptide's structure or function. This can be deduced, for example, from what structural and/or functional aspects are known or can be deduced from comparing the defined region(s) to what is known from the study of other polypeptides, and may be aided by modeling information. For example, the defined region can be one that has a role in a functional site, e.g., in binding, catalysis, or another functions. For example, regions determined to be important for FPP synthase function can include, for example, residues 97-137, 175-198 and 250-290 from FPP synthase of G. Gallus.

The amino acids selected for substitution represent the different side-chain chemistries known for the 20 natural amino acids, which include small, nucleophilic, hydrophobic, aromatic, acidic, amide and basic side-chain chemistries. An example of a small side-chain chemistry amino acid is alanine. An example of a nucleophilic side-chain chemistry amino acid is serine or histidine. An example of a hydrophobic side-chain chemistry amino acid is leucine or proline. An example of an aromatic side-chain chemistry amino acid is tyrosine. An example of an acidic side-chain chemistry amino acid is aspartic acid. An example of an amide side-chain chemistry amino acid is aspartate. An example of a basic side-chain chemistry amino acid is lysine. The methods of LTM are further described, for example, in Rajpal, et al. (2005) PNAS 102:8466-71, which is hereby incorporated by reference in its entirety.

As with WTM, certain amino acids are thought to be located in catalytic sites or proposed catalytic sites of a polypeptide. These amino acids, for example, belong to the group of polar and neutral amino acids such as Ser, Thr, Asn, Gln, Tyr, and Cys; the group of charged amino acids, Asp and Glu, Lys and Arg; and the amino acid His. While the side group chemistry of an amino acid can guide the selection of a predetermined amino acid residue, the lack of a desired side group chemistry can be a criterion for excluding an amino acid residue for use as the predetermined amino acid. For example, sterically small and chemically neutral amino acids, such as alanine, can be excluded from Look-Through mutagenesis for lacking a desired chemistry.

In one embodiment, a library of polypeptide analogs is generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid. This differs from the oligonucleotides produced in saturation mutagenesis, random mutagenesis, or walk-through mutagenesis in that, for each oligonucleotide, only specific mutations capturing each side-chain group are made.

The oligonucleotides can be produced individually and then mixed or pooled as desired. When the codon of the wild type sequence and the codon for the predetermined amino acid are the same, no substitution is made. Accordingly, the number of amino acid positions within the defined region will determine the maximum number of oligonucleotides made. Two or more regions can simultaneously be altered. In one embodiment, the amino acid residues (positions) within the defined region that are mutagenized are functional amino acid residues (positions). In another embodiment, the functional amino acid residues (positions) are exclusively mutagenized.

The size of the library will vary depending upon the length and number of regions and amino acids within a region that are mutagenized. For example, the library can be designed to contain less than $10^{15}$, less than $10^{14}$, less than $10^{13}$, less than $10^{12}$, less than $10^{11}$, less than $10^{10}$, less than $10^9$, less than $10^8$, less than $10^7$, or less than $10^6$ variant polypeptides, or less. The description above has centered on the mutagenesis of polypeptides and libraries of variant polypeptides by altering the polynucleotide that encodes the corresponding variant polypeptide. It is understood, however, that the scope of the disclosure also encompasses methods of mutagenizing polypeptides by direct synthesis of the desired polypeptide analogs using protein chemistry. In carrying out this approach, the resultant variant polypeptides still incorporate the features described herein except that the use of a polynucleotide intermediate is eliminated.

For the libraries described above, whether in the form of polynucleotides and/or corresponding polypeptides, it is understood that the libraries may be also attached to a solid support, such as a microchip, and arrayed, using art recognized techniques.

The look-through mutagenesis methods associated with the current disclosure may also be conducted with the benefit of structural and/or modeling information concerning the variant polypeptides to be generated, such that the potential for generating a variant polypeptide having an altered or desired property is increased. The structural and/or modeling information can also be used to guide the selection of a predetermined amino acid to introduce into the defined regions. Still further, actual results obtained with a variant polypeptide of the disclosure can guide the selection (or exclusion) of subsequent polypeptides to be made and screened in an iterative manner. Accordingly, structural and/or modeling information can be used to generate initial subsets of variant polypeptides for use in the disclosure, thereby further increasing the efficiency of generating altered or desired polypeptides. In one embodiment, in silico modeling is used to eliminate the production of any variant polypeptide predicted to have poor or undesired structure and/or function. In this way, the number of variant polypeptides to be produced can be sharply reduced thereby increasing signal-to-noise in subsequent screening assays. In another embodiment, functional amino acid residues (positions) or hot spots are identified as suitable for mutagenesis whereas nonfunctional amino acid residues (positions) or cold spots, are excluded. In another embodiment, the in silico modeling is continually updated with additional modeling information, from any relevant source, e.g., from gene and protein sequence and three-dimensional databases and/or results from previously tested variant polypeptides, so that the in silico database becomes more precise in its predictive ability.

The look-through method allows for the evaluation by mutagenesis of several different regions or domains of a polypeptide simultaneously. This can be done using the same or a different predetermined amino acid within each region, enabling the evaluation of amino acid substitutions in conformationally related regions, such as the regions that upon folding of the polypeptide, are associated to make up a functional site (e.g., the binding site of an antibody or the catalytic site of an enzyme). This, in turn, provides an efficient way to create new or improved functional sites.

Accordingly, the present disclosure allows for the design of many different types of variant polypeptides, such as variant prenyl transferases or variant isoprenoid synthases. The method can be used to improve upon an existing structure and/or function of a polypeptide. Alternatively, the introduction of additional "catalytically important" amino acids into a catalytic domain of a polypeptide enzyme can be performed resulting in a modified and/or enhanced catalytic activity toward a substrate. Alternatively, entirely new structures, specificities or activities may be introduced into a polypeptide. De novo synthesis of enzymatic activity can be achieved as well. The new structures can be built on the natural or consensus "scaffold" of an existing polypeptide by mutating only relevant regions (e.g., functional amino acid residues (positions)) by the methods of the disclosure.

Gene Shuffling

Gene shuffling is a method for recursive in vitro or in vivo homologous recombination of pools of nucleic acid fragments or polynucleotides. This method can also be used to create variants of prenyl transferase and isoprenoid synthase. Mixtures of related nucleic acid sequences or polynucleotides are randomly fragmented, and reassembled to yield a library or mixed population of recombinant nucleic acid molecules or polynucleotides. Gene shuffling, error-prone PCR, or use of other mutation-enhancement methods such as chemical mutagenesis and mutator strains, allows one to mutate a pool of sequences blindly (without sequence information other than primers). Since cross-over occurs at regions of homology, recombination can occur, for example, between members of the same family that have regions of sequence similarity. Multiple families of sequences can be shuffled in the same reaction.

The term "shuffling" encompasses a broad range of recursive recombination processes which can include, but are not limited to, PCR amplification or similar amplification methods. Shuffling can involve, for example, homologous recombination, site-specific recombination, and/or chimera formation (for example, as described in Levichkin et al. (1995) Mol Bio (Mosk) 29(5):983-991), so long as used recursively (i.e., for more than one cycle of sequence recombination) with selection and/or screening. Non-deterministic recombination (such as general homologous recombination) can be used in combination with or instead of deterministic recombination (such as site-specific recombination where the sites of recombination are known and/or defined).

The template polynucleotide which may be used in the methods of this disclosure may be DNA or RNA. It may be of various lengths depending on the size of the gene or DNA fragment to be recombined or reassembled. For example, the template polynucleotide can be from about 50 bp to about 50 kb. Entire vectors containing the polynucleotide encoding the protein of interest can be used in the methods of this disclosure.

The template polynucleotide may be obtained by amplification using PCR (for example, as described in U.S. Pat. Nos. 4,683,202 and 4,683,195) or other amplification or cloning methods known to one of skill in the art. Failure to adequately remove the primers can lead to a low frequency of crossover clones.

The template polynucleotide can be, for example, double-stranded. A double-stranded nucleic acid molecule is used to ensure that regions of the resulting single-stranded nucleic acid fragments are complementary to each other and thus can hybridize to form a double-stranded molecule.

Single-stranded or double-stranded polynucleotide fragments having regions of sequence identity to the template polynucleotide and regions of heterology to the template polynucleotide can be added to the template polynucleotide. In another embodiment, two different but related polynucleotide templates can be mixed.

The double-stranded polynucleotide template and any added double- or single-stranded fragments are randomly digested into fragments of, for example, from about 5 bp to about 5 kb or more. For example, the size of the random fragments can be from about 10 bp to about 1000 bp, or the size of the DNA fragments can be from about 20 bp to about 500 bp.

Alternatively, it is also contemplated that double-stranded polynucleotides having multiple nicks may be used in the methods of this disclosure. A nick is a break in one strand of the double-stranded polynucleotide. The distance between such nicks can be, for example, about bp to about 5 kb, or between about 10 bp to about 1000 bp.

The polynucleotide fragment may be digested by a number of different methods know to one of skill in the art. The polynucleotide fragment may be digested with a nuclease, such as DNAseI or RNAse. The polynucleotide may be randomly sheared by the method of sonication or by passage through a tube having a small orifice.

It is also contemplated that the polynucleotide may also be partially digested with one or more restriction enzymes, such that certain points of cross-over may be retained statistically.

The number of different specific nucleic acid fragments in the mixture can be, for example, at least about 100, or at least about 500, or at least about 1000.

Single-stranded or double-stranded nucleic acid fragments, either synthetic or natural, may be added to the random double-stranded nucleic acid fragments in order to increase the heterogeneity of the mixture of nucleic acid fragments. It is also contemplated that populations of double-stranded randomly broken or nicked nucleic acid fragments may be mixed or combined at this step. Damaged DNA can be exploited to enhance recombination via the nicked portions which can participate in, for example, strand invasion, formation of recombination junctions, or serve as free 3' ends for hybrid formation.

Where insertion of mutations into the template polynucleotide is desired, single-stranded or double-stranded nucleic acid fragments having a region of identity to the template polynucleotide and a region of heterology to the template polynucleotide may be added, for example, in a 20 fold excess by weight as compared to the total nucleic acid, or the single-stranded nucleic acid fragments may be added, for example, in a 10 fold excess by weight as compared to the total nucleic acid.

Where a mixture of different but related template polynucleotides is desired, populations of nucleic acid fragments from each of the templates may be combined at, for example, a ratio of less than about 1:100, or the ratio is less than about 1:40. For example, a backcross of wild-type polynucleotides with a population of mutated polynucleotides may be desired to eliminate neutral mutations (e.g., mutations yielding an insubstantial alteration in the phenotypic property being selected for). In such an example, the ratio of randomly digested wild-type polynucleotide fragments which may be added to the randomly digested mutated polynucleotide fragments is, for example, about 1:1 to about 100:1, or about 1:1 to about 40:1.

The mixed population of random length nucleic acid fragments are denatured to form single-stranded nucleic acid fragments and then reannealed. Only those single-stranded nucleic acid fragments having regions of homology with other single-stranded nucleic acid fragments will reanneal.

The random length nucleic acid fragments may be denatured by heating. One skilled in the art could determine the conditions necessary to completely denature the double stranded nucleic acid. The temperature can be, for example, from about 80° C. to about 100° C., or the temperature can be from about 90° C. to about 96° C. Other methods which may be used to denature the nucleic acid fragments include pressure and pH and are know to one skilled in the art.

The nucleic acid fragments may be reannealed by cooling. The temperature can be, for example, from about 20° C. to about 75° C., or the temperature can be from about 40° C. to about 65° C. If a high frequency of crossovers are needed, based on an average of only 4 consecutive bases of homology, recombination can be forced by using a low annealing temperature. The degree of renaturation which occurs will depend on the degree of homology between the population of single-stranded nucleic acid fragments.

The cycle of denaturation, renaturation and incubation in the presence of polymerase can be referred to as shuffling or reassembly of the nucleic acid. This cycle is repeated for a desired number of times. The cycle can be repeated, for example, from 2 to 50 times or from 10 to 40 times.

After the cycles, described above, the polynucleotide is a larger double-stranded polynucleotide of, for example, about 50 bp to about 100 kb, or the larger polynucleotide is about 500 bp to about 50 kb.

This larger polynucleotide fragment may contain a number of copies of a nucleic acid fragment having the same size as the template polynucleotide organized in tandem. This concatemeric fragment is then digested into single copies of the template polynucleotide. The result will be a population of nucleic acid fragments of approximately the same size as the template polynucleotide. The population will be a mixed population where single or double-stranded nucleic acid fragments having an area of identity and/or an area of heterology have been added to the template polynucleotide prior to shuffling. Alternatively, the concatemer can be introduced (e.g., via electroporation or lipofection) directly without monomerization. For large sequences, it may be desirable to subdivide the large sequence into several subportions which are separately shuffled with other substantially similar portions, and the pool of resultant shuffled subportions then ligated, typically in original order, to generate a pool of shuffled large sequences which can then be used for transformation of a host cell.

In some embodiments, a number of cycles of nucleic acid shuffling may be conducted with nucleic acid fragments from a subpopulation of a first population, which subpopulation contains DNA encoding the desired recombinant protein. In this manner, proteins with even higher binding affinities and/or enzymatic activity can be achieved.

In other embodiments, a number of cycles of nucleic acid shuffling may be conducted with a mixture of wild-type nucleic acid fragments and a subpopulation of nucleic acid from the first or subsequent rounds of nucleic acid shuffling in order to remove any silent mutations from the subpopulation.

Random Mutagenesis

Any source of nucleic acid, in purified form can be utilized as the starting nucleic acid. Thus, the process may employ DNA or RNA including messenger RNA, which DNA or RNA may be single or double stranded, in addition, a DNA-RNA hybrid which contains one strand of each may be utilized. The nucleic acid sequence may be of various lengths depending on the size of the nucleic acid sequence to be mutated. The specific nucleic acid sequence can be, for example, from 50 to 50000 base pairs. Entire vectors containing the nucleic acid encoding the protein of interest may be used in the methods of this disclosure.

The first small population of specific nucleic acid sequences having mutations may be created by a number of different methods. Mutations may be created, for example, by error-prone PCR. Error-prone PCR uses low-fidelity polymerization conditions to introduce a low level of point mutations randomly over a long sequence. Alternatively, mutations can be introduced into the template polynucleotide, for example, by oligonmucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be, for example, altered by chemical mutagenesis. Chemical mutagens include, for example, sodium bisulfite, nitrous acid, hydroxylamine, hydrazine or formic acid. Chemical mutagens may also include, for example, nitrosoguanidine, 5-bromouracil, 2-aminopurine, or acridine, which can be converted into nucleotides by the host cell, incorporated into DNA, and then cannot be accurately replicated during cell division. Generally, these agents are added to the PCR reaction in place of the nucleotide precursors thereby mutating the sequence. Intercalating agents such as proflavine, acriflavine, quinacrine, and similar agents can also be used. Random mutagenesis of the polynucleotide sequence can also be achieved by irradiation with X-rays or ultraviolet light. Plasmid DNA or DNA fragments mutagenized by the methods described herein can be introduced into an organism, such as E. coli, and propagated as a pool or library of mutant plasmids. Alternatively, the first small population of specific nucleic acids may be found in nature, for example, they may consist of different alleles of the same gene, the same gene from different related species (i.e., cognate genes), or related DNA sequences found within one species.

In Vitro Shuffling

The equivalents of some standard genetic matings may also be performed by shuffling in vitro. For example, a "molecular backcross" can be performed by repeated mixing of a mutated nucleic acid with a wild-type nucleic acid while selecting for the mutation of interest. As in traditional breeding, this approach can be used to combine phenotypes from different sources into a background of choice. It is useful, for example, for the removal of neutral mutations that affect unselected characteristics. Thus, this method can be useful to determine which mutations in a protein are involved in, for example, the enhanced biological activity.

In Vivo Shuffling

In one embodiment of in vivo shuffling, the mixed population of specific nucleic acid sequences is introduced into bacterial or eukaryotic cells under conditions such that at least two different nucleic acid molecules are introduced into the majority of the host cell population. The fragments can be introduced into the host cells by a variety of different methods. The host cells can be transformed with the fragments using methods known in the art, for example treatment with calcium chloride. If the fragments are inserted into a phage genome, the host cell can be transfected with the recombinant phage genome having the specific nucleic acid sequences. Alternatively, the nucleic acid sequences can be introduced into the host cell using electroporation, natural competence, transduction, transfection, lipofection, biolistics, conjugation, or other suitable methods of introducing a polynucleotide sequence into a cell known to one of skill in the art.

Directed Evolution

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one embodiment, the disclosure provides methods for producing a variant polypeptide encoded by a polynucleotide comprising at least a first polynucleotide and a second polynucleotide. The present disclosure can be used, for example, to produce a variant polypeptide encoded by a hybrid polynucleotide by introducing at least a first polynucleotide and a second polynucleotide which share at least one region of partial sequence homology into a suitable host cell. The regions of partial sequence homology result in sequence reorganization producing a hybrid polynucleotide. The term "hybrid polynucleotide", as used herein, is any nucleotide sequence which results from the method of the present disclosure and contains sequences from at least two original polynucleotide sequences. Such hybrid polynucleotides can result, for example, from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The disclosure provides a means for generating hybrid polynucleotides which encode for biologically active hybrid polypeptides. The method of the disclosure produces hybrid polypeptides by utilizing cellular processes which integrate the sequences of the original polynucleotides such that the resulting hybrid polynucleotide encodes a polypeptide demonstrating activities derived from the original biologically active polypeptides. For example, the two original polynucleotides may each encode for an enzyme from a different microorganism. An enzyme encoded by a first polynucleotide from one organism may, for example, function effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

In one embodiment, the present disclosure includes a method for producing a biologically active hybrid polypeptide and screening such a polypeptide for enhanced activity by: 1) introducing at least a first polynucleotide and a second polynucleotide, wherein the at least first polynucleotide and second polynucleotide sharing at least one region of partial sequence homology, into a suitable host cell; 2) growing the host cell under conditions which promote sequence reorganization resulting in a hybrid polynucleotide; 3) expressing a hybrid polypeptide encoded by the hybrid polynucleotide; 4) screening the hybrid polypeptide under conditions which promote identification of enhanced biological activity; and 5) isolating the polynucleotide encoding the hybrid polypeptide.

Sources of the original polynucleotides may be isolated from individual organisms ("isolates"), collections of organisms that have been grown in defined media ("enrichment cultures"), or environmental samples.

"Environmental libraries" are generated from environmental samples and represent the collective genomes of naturally occurring organisms. A genome can be archived in cloning vectors that can be propagated in suitable prokaryotic or eukaryotic hosts. Because the cloned DNA is initially extracted directly from an environmental sample, the libraries are not limited to the small fraction of prokaryotes that can be grown in pure culture. Additionally, a normalization of the environmental DNA present in these samples could allow for more equal representation of the DNA from all of the species present in the original sample. This can dramatically increase the efficiency of finding interesting genes from minor constituents of the sample which may be under-represented by several orders of magnitude compared to a dominant species.

For example, gene libraries generated from one or more uncultivated microorganisms are screened for an activity of interest. Gene clusters encoding members of a pathway of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganism(s) from which the polynucleotide may be prepared include, for example, prokaryotic microorganisms, such as Eubacteria and Archaebacteria, and lower eukaryotic microorganisms, such as fungi, algae and protozoa. In other embodiments, the microorganism(s) may be extremophiles, such as hyperthermophiles, psychrophiles, psychrotrophs, halophiles, barophiles and acidophiles. Polynucleotides may be isolated from environmental samples in which case the nucleic acid may be recovered without culturing of an organism or recovered from one or more cultured organisms. Polynucleotides encoding enzymes isolated from extremophilic microorganisms can be used in the disclosed embodiments. Such enzymes may function, for example, at temperatures above about 100° C. in terrestrial hot springs and deep sea thermal vents, at temperatures below about 0° C. in arctic waters, in the saturated salt environment of the Dead Sea, at pH values around 0 in coal deposits and geothermal sulfur-rich springs, or at pH values greater than about 11 in sewage sludge. For example, several esterases and lipases cloned and expressed from extremophilic organisms show high activity throughout a wide range of temperatures and pHs.

The DNA isolated or derived from a microorganism can be inserted into a vector (construct) or a plasmid prior to probing for selected DNA. Such vectors or plasmids can contain expression regulatory sequences, for example, promoters and enhancers. A phage can also be used to introduce DNA into a host organism or cell.

Reductive Reassortment

Reductive reassortment is one example of directed evolution. In another embodiment of the present disclosure, variant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of variant molecular species. Various treatments may be applied to enhance the rate of reassortment. These could include treatment with ultra-violet light, or DNA damaging chemicals, and/or the use of host cell lines displaying enhanced levels of "genetic instability". Thus, the reassortment process may involve homologous recombination or the natural property of quasi-repeated sequences to direct their own evolution.

DNA Shuffling by Sexual PCR

DNA shuffling by sexual PCR is one example of directed evolution. Variant polypeptides of the disclosure having altered properties can also be produced using "Sexual PCR." In one embodiment of the present disclosure, amplified or cloned polynucleotides possessing a desired characteristic (for example, encoding a polypeptide with a region of higher specificity to a substrate) are selected (for example, via screening of a library of polynucleotides) and pooled. The pooled polynucleotides (or at least one polynucleotide) may be subjected to random primer extension reactions and/or PCR amplification using random primers, to multiply portions of the polynucleotide or polynucleotides. At various stages along the completion of the PCR amplification process, the process may be blocked or interrupted. Hence, a collection of incomplete copies of the polynucleotide or polynucleotides can be generated by random primer extension reactions, amplification using random primers, and/or by pausing or stopping the replication process.

These collections of shorter or smaller polynucleotides (pools) may be isolated or collectively amplified further by PCR, which may be interrupted again. Such "stacking" of the amplification and pausing or stopping steps has the advantage of producing a truly randomized sample of polynucleotides having widely varying lengths. For example, some of the smaller polynucleotides may hybridize with the longer polynucleotides and act as additional random primers to initiate self-priming amplification of polynucleotides within the pool.

Such a process provides an efficient means for producing widely-varying random polynucleotides and subsequent widely-varying mutant proteins corresponding to the same random selection as in the random polynucleotide pool. The reassembly of the shorter or smaller polynucleotides after such shuffling to produce the random polynucleotides may be provided by utilizing procedures standard in the art.

In one embodiment of the disclosure, an adduct or adducts can be used to halt or slow the PCR. These adduct(s) can be modified with a chemical group for which there exists (or can be obtained) a monoclonal antibody specific for the chemical group. This is an example of an efficient separation of polynucleotide chains comprising the DNA adducts (or for the removal of the adducts which have been released from the DNA polynucleotides which comprise them) from other polynucleotide chains. In some situations, it may be desirable to remove such DNA adducts before further processing of the amplified polynucleotides. In other situations it may be desirable to leave such DNA adducts in the solution with the intention of producing a further randomized pool of polynucleotides. Whether the DNA adduct is to be removed or left within the polynucleotide pool depends upon the composition of the adduct itself and the immediate goal of that amplification process step.

In another embodiment, the polynucleotides produced by interrupting the PCR amplification (and optionally subsequent amplification of the polynucleotides to produce further randomization, under conditions suitable for PCR amplifications) are recombined to form a shuffled pool of recombined polynucleotides, whereby a substantial fraction (e.g., greater than about 10 percent) of the recombined polynucleotides of the shuffled pool were not present in the PCR amplification reaction. Thus, the shuffled pool provides a library of displayed polypeptides or displayed antibodies suitable, for example, for affinity interaction screening.

Optionally, the method comprises the additional step of screening the library members of the shuffled pool to identify individual shuffled library members having an altered property (e.g., increased binding specificity to a substrate).

In one embodiment, the PCR amplification reaction products are produced and homologously recombined by PCR in vitro, the resultant polynucleotides are transferred into a host cell or organism via a transferring means and homologously recombined to form shuffled library members in vivo.

In another embodiment, the selected library members are cloned or amplified on episomally replicable vectors, a multiplicity of the vectors are transferred into a cell and homologously recombined to form shuffled library members in vivo.

In an embodiment, combinations of in vitro and in vivo shuffling are provided to enhance combinatorial diversity.

The present disclosure provides a method for generating libraries of variant polypeptides having at least one altered property. The method comprises (1) obtaining a plurality of selected library members comprising an altered polypeptide and an associated polynucleotide encoding the altered polypeptide, and (2) pooling and producing shorter or smaller polynucleotides with the associated polynucleotides or copies to form polynucleotides under conditions suitable for PCR amplification by slowing or halting the PCR amplification and thereby homologously recombining the shorter or smaller polynucleotides to form a shuffled pool of recombined polynucleotides of the shuffled pool. Optionally, the shuffled pool is subjected to screening for desired properties (e.g., increased binding specificity to a substrate). Further, the plurality of selectedly shuffled library members can be shuffled and screened iteratively, from 1 to about 1000 cycles or as desired until library members having a desired binding affinity are obtained.

Combinational Approaches

Methods described above and any other methods known in the art may be used in a combinatorial beneficial mutation approach, in which coding sequences are generated which represent combinations of the beneficial mutations identified by various mutation methods, including those described above. For example, one combinatorial approach resembles the walk-through method except that the selected substrate binding regions are the different beneficial amino-acid substitutions identified by LTM. A combinatorial library of mutations may also be generated by known gene shuffling methods, for example, as described in U.S. patent publication number 2003/005439A1, U.S. Pat. No. 6,368,861, and Stemmer, W P (1994) Proc Natl Acad Sci 91 (22): 10747-51, all of which are incorporated herein by reference. Other combinatorial approaches are known to one of skill in the art.

Host Cells or Host Organisms

The present disclosure provides polynucleotides encoding a variant polypeptide (e.g., a variant prenyl transferase or a variant isoprenoid synthase enzyme), as well as recombinant vectors and recombinant host cells comprising the polynucleotides.

A host cell cart contain a variant polynucleotide encoding a variant polypeptide of the present disclosure. In some embodiments, a host cell is part of a multicellular organism. In other embodiments, a host cell is cultured as a unicellular organism.

Host organisms can include any suitable host, for example, a microorganism. Microorganisms which are useful for the methods described herein include, for example, photosynthetic bacteria (e.g., cyanobacteria), non-photosynthetic bacteria (e.g., *E. coli*), yeast (e.g., *Saccharomyces cerevisiae*), and algae (e.g., microalgae such as (*Chlamydomonas reinhardtii*).

Examples of host organisms that can be transformed using the compositions and methods herein include vascular and non-vascular organisms. The organism can be prokaroytic or eukaroytic. The organism can be unicellular or multicellular. A host organism is an organism comprising a host cell. In other embodiments, the host organism is photosynthetic. A photosynthetic organism is one that naturally photosynthesizes (e.g., an alga) or that is genetically engineered or otherwise modified to be photosynthetic. In some instances, a photosynthetic organism may be transformed with a construct or vector of the disclosure which renders all or part of the photosynthetic apparatus inoperable.

By way of example, a non-vascular photosynthetic microalga species (for example, *C. reinhardtii, Nannochloropsis oceania, N. salina. D. salina, H. pluvalis, S. dimorphus, D. viridis*, and *D. tertiolecta*) can be genetically engineered to produce a terpene or terpenoid. Production of a terpene or terpenoid in these microalgae can be achieved by engineering the microalgae to express a variant enzyme in the algal chloroplast or nucleus.

The host cell can be prokaryotic. Examples of some prokaryotic organisms of the present disclosure include, but are not limited to, cyanobacteria (e.g., *Synechococcus, Synechocystis, Athrospira*). Suitable prokaryotic cells include, but are not limited to, any of a variety of laboratory strains of *Escherichia coli, Lactobacillus* sp., *Salmonella* sp., and *Shigella* sp. (for example, as described in Carrier et al. (1992) J. Immunol. 148:1176-1181; U.S. Pat. No. 6,447,784; and Sizemore et al. (1995) Science 270:299-302). Examples of *Salmonella* strains which can be employed in the present disclosure include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Pseudomonas pudita, Pseudomonas aeruginosa, Pseudomonas mevalonii, Rhodobacter sphaeroides, Rhodobacter capsulatus, Rhodospirillum rubrum*, and *Rhodococcus* sp.

In some embodiments, the host organism is eukaryotic (e.g. green algae, red algae, brown algae). Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia menmbranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa*, and *Chlamydomonas reinhardtii*. In other embodiments, the host cell is a microalga (e.g., *Chlamydomonas reinhardtii, Dunaliella salina, Haematococcus pluvialis, Nannochloropsis oceania, N. salina, Scenedesmus dimorphus, Chlorella* sp., *D. viridis*, or *D. tertiolecta*).

In some instances a host organism is vascular and photosynthetic. Examples of vascular plants include, but are not limited to, angiosperms, gymnosperms, rhyniophytes, or other tracheophytes.

In some instances a host organism is non-vascular and photosynthetic. As used herein, the term "non-vascular photosynthetic organism," refers to any macroscopic or microscopic organism, including, but not limited to, algae, cyanobacteria and photosynthetic bacteria, which does not have a vascular system such as that found in vascular plants. Examples of non-vascular photosynthetic organisms include bryophtyes, such as marchantiophytes or anthocerotophytes. In some instances the organism is a cyanobacteria. In some instances, the organism is algae (e.g., macroalgae or microalgae). The algae can be unicellular or multicellular algae. For example, the microalgae *Chlaydomonas reinhardtii* may be transformed with a vector, or a linearized portion thereof encoding one or more proteins of interest (e.g., a variant prenyl transferase).

Methods for algal transformation are described in U.S. Provisional Patent Application No, 60/142,091. The methods of the present disclosure can be carried out using algae, for example, the microalga, *C. reinhardtii*. The use of microalgae to express a polypeptide or protein complex according to a method of the disclosure provides the advantage that large populations of the microalgae can be grown, including commercially (Cyanotech Corp.; Kailua-Kona Hi.), thus allowing for production and, if desired, isolation of large amounts of a desired product.

The vectors of the present disclosure may be capable of stable or transient transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. Other vectors of the present disclosure are capable of stable or transient transformation of, for example, *C. reinhardtii, N. oceania, N. salina, D. salina, H. pluvalis, S. dimorphus, D. viridis*, or *D. tertiolecta*.

Examples of appropriate hosts, include but are not limited to: bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; and plant cells. The selection of an appropriate host is deemed to be within the scope of those skilled in the art.

Polynucleotides selected and isolated as described herein are introduced into a suitable host cell. A suitable host cell is any cell which is capable of promoting recombination and/or reductive reassortment. The selected polynucleotides can be, for example, in a vector which includes appropriate control sequences. The host cell can be, for example, a higher eukaryotic cell, such as a mammalian cell, or a lower eukaryotic cell, such as a yeast cell, or the host cell can be a prokaryotic cell, such as a bacterial cell. Introduction of a construct (vector) into the host cell can be effected by, for example, calcium phosphate transfection, DEAE-Dextran mediated transfection, or electroporation.

Recombinant polypeptides, including protein complexes, can be expressed in plants, allowing for the production of crops of such plants arnd, therefore, the ability to conveniently produce large amounts of a desired product. Accordingly, the methods of the disclosure can be practiced using any plant, including, for example, microalga and macroalgae, (such as marine algae and seaweeds), as well as plants that grow in soil.

The term "plant" is used broadly herein to refer to a eukaryotic organism containing plastids, such as chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, and roots. A part of a plant useful for propagation includes, for example, seeds, fruits, cuttings, seedlings, tubers, and rootstocks.

A method of the disclosure can generate a plant containing genomic DNA (for example, a nuclear and/or plastid genomic DNA) that is genetically modified to contain a stably integrated polynucleotide (for example, as described in Hager and Bock, *Appl. Microbiol. Biotechnol.* 54:302-310, 2000). Accordingly, the present disclosure further provides a transgenic plant, e.g. *C. reinhardtii*, which comprises one or more chloroplasts containing a polynucleotide encoding one or more exogenous or endogenous polypeptides, including polypeptides that can allow for secretion of fuel products and/or fuel product precursors (e.g., isoprenoids, fatty acids, lipids, triglycerides). A photosynthetic organism of the present disclosure comprises at least one host cell that is modified to generate, for example, a fuel product or a fuel product precursor.

Some of the host organisms useful in the disclosed embodiments are, for example, are extremophiles, such as hyperthermophiles, psychrophiles, psychrotrophs, halophiles, barophiles and acidophiles. Some of the host organisms which may be used to practice the present disclosure are halophilic (e.g., *Dunaliella salina, D. viridis*, or *D. tertiolecta*). For example, *D. salina* can grow in ocean water and salt lakes (for example, salinity from 30-300 parts per thousand) and high salinity media (e.g., artificial seawater medium, seawater nutrient agar, brackish water medium, and seawater medium). In some embodiments of the disclosure, a host cell comprising a vector of the present disclosure can be grown in a liquid environment which is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 31., 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, or other salts) may also be present in the liquid environments.

Where a halophilic organism is utilized for the present disclosure, it may be transformed with any of the vectors described herein. For example, *D. salina* may be transformed with a vector which is capable of insertion into the chloroplast or nuclear genome and which contains nucleic acids which encode an isoprenoid producing enzyme (e.g., FPP synthase, zingiberene synthase, squalene synthase). Transformed halophilic organisms may then be grown in high-saline environments (e.g., salt lakes, salt ponds, and high-saline media) to produce the products (e.g., isoprenoids) of interest. Isolation of the products may involve removing a transformed organism from a high-saline environment prior to extracting the product from the organism. In instances where the product is secreted into the surrounding environment, it may be necessary to desalinate the liquid environment prior to any further processing of the product.

A host organism may be grown under conditions which permit photosynthesis, however, this is not a requirement (e.g., a host organism may be grown in the absence of light). In some instances, the host organism may be genetically modified in such a way that photosynthetic capability is diminished and/or destroyed (see examples below). In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

A host organism may also be grown on land, e.g., landfills. In some cases, host organism(s) are grown near ethanol production plants or other facilities or regions (e.g., cities and highways) generating $CO_2$. As such, the methods herein contemplate business methods for selling carbon credits to ethanol plants or other facilities or regions generating $CO_2$ while making fuels or fuel products by growing one or more of the modified organisms described herein near the ethanol production plant.

Further, the organisms may be grown in outdoor open water, such as ponds, the ocean, sea, rivers, waterbeds, marsh water, shallow pools, lakes, and reservoirs. When grown in water, the organisms can be contained in a halo like object comprising of lego-like particles. The halo object encircles the algae and allows it to retain nutrients from the water beneath while keeping it in open sunlight.

In some instances, organisms can be grown in containers wherein each container comprises 1 or 2 or a plurality of organisms. The containers can be configured to float on water. For example, a container can be filled by a combination of air and water to make the container and the host organism(s) in it buoyant. A host organism that is adapted to grow in fresh water can thus be grown in salt water (i.e., the ocean) and vice versa. This mechanism allows for automatic death of the organism if there is any damage to the container.

In some instances a plurality of containers can be contained within a halo-like structure as described above. For example, up to 100, 1,000, 10,000, 100,000, or 1,000,000 containers can be arranged in a meter-square of a halo-like structure. In some embodiments, the product (e.g. fuel molecule) is collected by harvesting the liquid medium. As some fuel molecules (e.g., monoterpenes) are immiscible in water, they would float to the surface of the liquid medium and could be extracted easily. In other instances, the fuel molecules can be extracted from the liquid medium. In still other instances, the fuel molecules are volatile. In such instances, impermeable barriers can cover or otherwise surround the growth environment and can be extracted from the air within the barrier. For some fuel molecules, the product may be extracted from both the environment (e.g., liquid environment and/or air) and from the intact host cells. Typically, the organism would be harvested at an appropriate point and the product may then be extracted from the organism. In some instances, the product may be produced without killing the organisms. Producing and/or expressing the product may not render the organism unviable.

The present disclosure further provides compositions comprising a genetically modified host cell. A composition comprises a genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol and dimethylsulfoxide; and nutritional media appropriate to the cell.

For the production of an isoprenoid or isoprenoid precursor compound, a host cell can be, for example, one that produces, or has been genetically modified to produce, one or more enzymes in a prenyl transferase pathway and/or a mevalonate pathway and/or an isoprenoid biosynthetic pathway. In some embodiments, the host cell is one that produces a substrate of a variant prenyl transferase, isoprenoid synthase or mevalonate pathway enzyme.

In some embodiments, a genetically modified host cell is a host cell that comprises an endogenous mevalonate pathway and/or isoprenoid biosynthetic pathway and/or prenyl transferase pathway. In other embodiments, a genetically modified host cell is a host cell that does not normally produce mevalonate or IPP via a mevalonate pathway, or FPP, GPP or GGPP via a prenyl transferase pathway, but has been genetically modified with one or more polynucleotides comprising nucleotide sequences encoding one or more mevalonate pathway, isoprenoid synthase pathway or prenyl transferase pathway enzymes (for example, as described in U.S. Patent Publication No. 2004/005678; U.S. Patent Publication No. 2003/0148479; and Martin et al. (2003) Nat. Biotech. 21(7):796-802).

Polynucleotides selected and isolated as described herein are introduced into a suitable host cell. A suitable host cell is any cell which is capable of promoting recombination and/or reductive reassortment. The selected polynucleotide(s) can be, for example, inserted into a vector which includes appropriate control sequences. The host cell can be, for example, a higher eukaryotic cell, such as a mammalian cell, or a lower eukaryotic cell, such as a yeast cell, or the host cell can be a prokaryotic cell, such as a bacterial cell.

Introduction of Variant Nucleic Acids into a Host Organism or Cell

To generate a genetically modified host cell, a polynucleotide, or a polynucleotide cloned into a vector, is introduced stably or transiently into a host cell, using established techniques, including, but not limited to, electroporation, calcium phosphate precipitation, DEAE-dextran mediated transfection, and liposome-mediated transfection. For transformation, a polynucleotide of the present disclosure will generally further include a selectable marker, e.g., any of several well-known selectable markers such as neomycin resistance, ampicillin resistance, tetracycline resistance, chloramphenicol resistance, and kanamycin resistance.

A polynucleotide or recombinant nucleic acid molecule described herein, can be introduced into a plant cell (e.g., alga cell) using any method known in the art. A polynucleotide can be introduced into a cell by a variety of methods, which are well known in the art and selected, in part, based on the particular host cell. For example, the polynucleotide can be introduced into a plant cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, *Ann. Rev. Plant. Physiol. Plant Mol. Biol.* 42:205-225, 1991).

Microprojectile mediated transformation also can be used to introduce a polynucleotide into a plant cell (for example, as described in Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known in the art (for example, as described in Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., *Nature Biotech.* 14:494-498, 1996; and Shimamoto, *Curr. Opin. Biotech.* 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

In some embodiments, an alga is transformed with a variant nucleic acid which encodes a protein of interest, for example, a variant prenyl transferase, a variant isoprenoid synthase, or a variant enzyme capable of converting a precursor into a fuel product or a precursor of a fuel product (e.g., an isoprenoid or fatty acid). In one embodiment, a transformation may introduce a variant nucleic acid into a plastid of the host alga (e.g., chloroplast). In another embodiments a transformation may introduce a variant nucleic acid into the nuclear genome of the host alga. In still another embodiment, a transformation may introduce nucleic acids into both the nuclear genome and into a plastid. Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which EDTA (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Transporter and/or product screening may be performed by any method known in the art, for example ATP turnover assay, substrate transport assay, HPLC or gas chromatography.

The expression of the variant enzyme can be accomplished by inserting a polynucleotide sequence (gene) encoding the variant enzyme into the chloroplast or nuclear genome of a microalgae. The modified strain of microalgae can be made homoplasmic to ensure that the variant polynucleotide will be stably maintained in the chloroplast genome of all descendents. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

Vectors

Construct, vector and plasmnid are used interchangeably throughout the disclosure. In some embodiments, a polynucleotide of the present disclosure is cloned or inserted into an expression vector using cloning techniques know to one of skill in the art. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, and herpes simplex virus), PI-based artificial chromosomes, yeast plasmids, yeast artificial chromosomes, and any other vectors specific for specific hosts of interest (such as *E. coli* and yeast). Thus, for example, a polynucleotide encoding a variant prenyl transferase or isoprenoid synthase can be inserted into any one of a variety of expression vectors for expressing the variant prenyl transferase or isoprenoid synthase. Such vectors can include, for example, chromosomal, nonchromosomal and synthetic DNA sequences.

Figure 10:
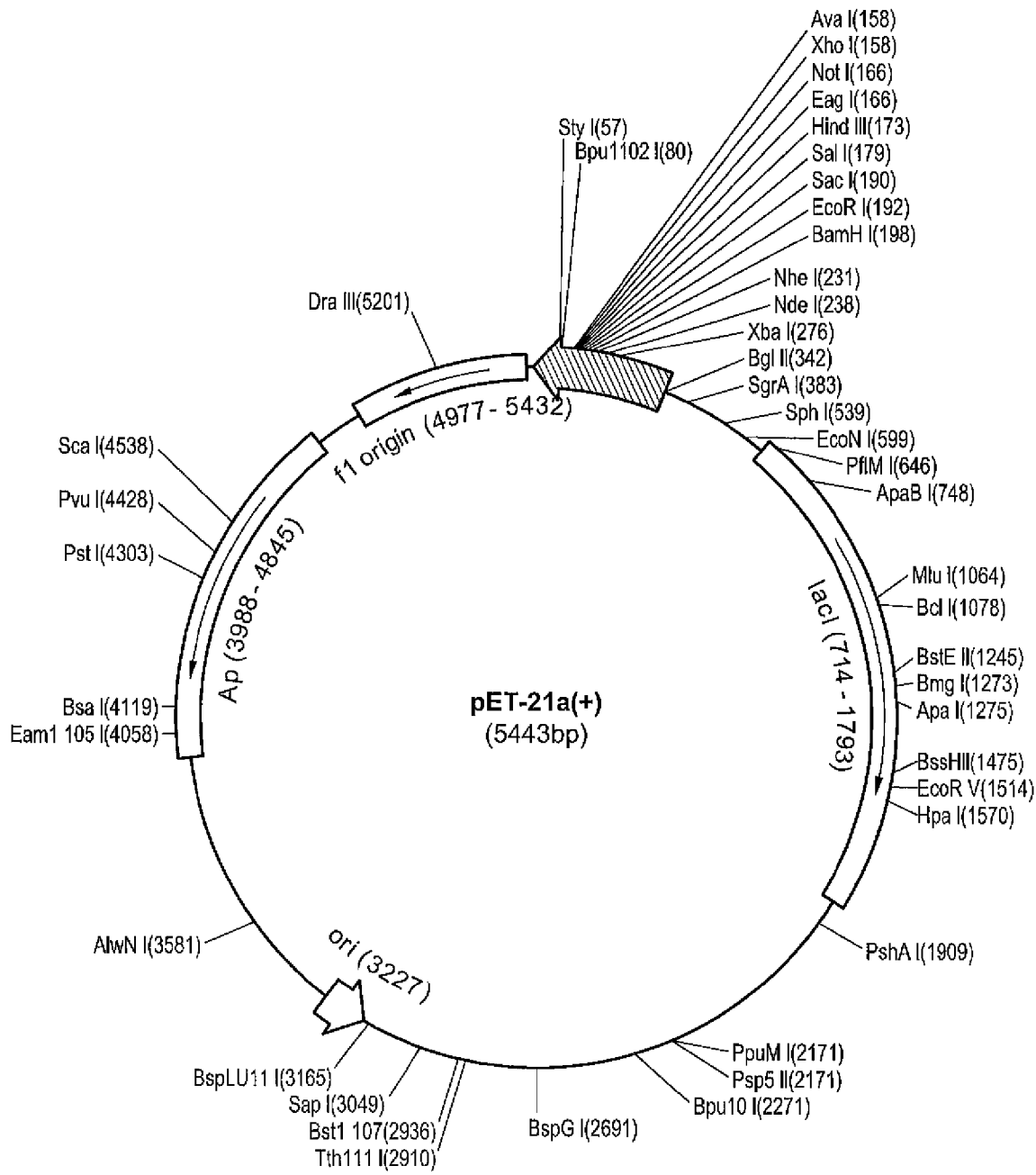
FIG. 10 shows an exemplary vector pET-21a(+) useful in the disclosed embodiments.

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET-21a(+) and pET21a-d(+) vectors (FIG. 10; Novagen), and pSVLSV40 (Pharmacia). However, any other plasmid or other vector may be used so long as it is compatible with the host cell.

The expression vector, or a linearized portion thereof, can encode one or more exogenous or endogenous nucleotide sequences. Examples of exogenous nucleotide sequences that can be transformed into a host, for example, an algal host, include genes from bacteria, fungi, plants, photosynthetic bacteria or other algae. Examples of other types of nucleotide sequences that can be transformed into a host, for example, an algal host include, but are not limited to, transporter genes, isoprenoid producing genes, including genes which encode for proteins which produce isoprenoids with two phosphates (e.g., GPP synthase and/or FPP synthase), genes which encode for proteins which produce fatty acids, lipids or triglycerides, endogenous promoters and 5' UTRs from the psbA, atpA, or rbcL genes. In some instances, an exogenous sequence is flanked by two homologous sequences.

Homologous sequences are, for example, those that have at least 50%, at least 60%, at least 70%, at least 80%, at least 90%, at least 95%, at least 98%, or at least at least 99% sequence identity to a reference amino acid sequence, for example, the amino acid sequence found naturally in the host cell. The first and second homologous sequences enable recombination of the exogenous or endogenous sequence into the genome of the host organism. The first and second homologous sequences can be at least 100, at least 200, at least 300, at least 400, at least 500, or at least 1500 nucleotides in length.

The polynucleotide sequence may comprise nucleotide sequences that are codon biased for expression in the organism being transformed. The skilled artisan is well aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. In some organisms, codon bias differs between the nuclear genome and organelle genomes, thus, codon optimization or biasing may be performed for the target genome (e.g., nuclear codon biased or chloroplast codon biased). In some embodiments, codon biasing occurs before mutagenesis to generate a polypeptide variant. In other embodiments, codon biasing occurs after mutagenesis to generate a polypeptide variant. In yet other embodiments, codon biasing occurs before mutagenesis as well as after mutagenesis. Codon bias is described in detail above.

In some embodiments, a vector comprises a polynucleotide operably linked to one or more control elements, such as a promoter and/or a transcription terminator. A vector in some embodiments provides for amplification of the copy number of a polynucleotide. A vector can be, for example, an expression vector that provides for expression of a variant prenyl transferase, a variant isoprenoid synthase, or a variant mevalonate synthesis enzyme in a host cell, e.g., a prokaryotic host cell or a eukaryotic host cell. A vector can also be, for example, an expression vector that provides for expression of a parent prenyl transferase, a parent isoprenoid synthase, or a parent mevalonate synthesis enzyme in a host cell, e.g., a prokaryotic host cell or a eukaryotic host cell.

A polynucleotide or polynucleotides can be contained in a vector or vectors. For example, where a second (or more) variant nucleic acid molecule is desired, the second nucleic acid molecule can be contained in a vector, which can, but need not be, the same vector as that containing the first variant nucleic acid molecule. The vector can be any vector useful for introducing a polynucleotide into a genome and can include a nucleotide sequence of genomic DNA (e.g., nuclear or plastid) that is sufficient to undergo homologous recombination with genomic DNA, for example, a nucleotide sequence comprising about 400 to about 1500 or more substantially contiguous nucleotides of genomic DNA.

In some instances, such vectors include promoters. Promoters useful for the present disclosure may come from any source (e.g., viral, bacterial, fungal, protist, and animal). The promoters contemplated herein can be specific to photosynthetic organisms, non-vascular photosynthetic organisms, and vascular photosynthetic organisms (e.g., algae, flowering plants). In some instances, the nucleic acids above are inserted into a vector that comprises a promoter of a photosynthetic organism, e.g., algae. The promoter can be a constitutive promoter or an inducible promoter. A promoter typically includes necessary nucleic acid sequences near the start site of transcription, (e.g., a TATA element).

A "constitutive" promoter is a promoter that is active under most environmental and developmental conditions. An "inducible" promoter is a promoter that is active under controllable environmental or developmental conditions. Examples of inducible promoters/regulatory elements include, for example, a nitrate-inducible promoter (for example, as described in Bock et al, *Plant Mol. Biol.* 17:9 (1991)), or a light-inducible promoter, (for example, as described in Feinbaum et al, Mol. Gen. Genet. 226:449 (1991); and Lam and Chua, Science 248:471 (1990)), or a heat responsive promoter (for example, as described in Muller et al., Gene 111: 165-73 (1992)).

In many embodiments, a polynucleotide of the present disclosure includes a nucleotide sequence encoding a variant enzyme of the present disclosure, where the nucleotide sequence encoding the variant polypeptide is operably linked to an inducible promoter. Inducible promoters are well known in the art. Suitable inducible promoters include, but are not limited to, the pL of bacteriophage λ; Placo; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (for example, as described in Guzman et al. (1995) J. Bacteriol. 177:4121-4130); a xylose-inducible promoter, e.g., Pxyl (for example, as described in Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; and a heat-inducible promoter, e.g., heat inducible lambda $P_L$ promoter and a promoter controlled by a heat-sensitive repressor (e.g., C1857-repressed lambda-based expression vectors; for example, as described in Hoffmann et al. (1999) FEMS Microbiol Lett. 177(2):327-34).

In many embodiments, a polynucleotide of the present disclosure includes a nucleotide sequence encoding a variant enzyme of the present disclosure, where the nucleotide sequence encoding the variant polypeptide is operably linked to a constitutive promoter. Suitable constitutive promoters for use in prokaryotic cells are known in the art and include, but are not limited to, a sigma70 promoter, and a consensus sigma70 promoter.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter; an araBAD promoter; in vivo regulated promoters, such as an ssaG promoter or a related promoter (for example, as described in U.S. Patent Publication No. 20040131637), a pagC promoter (for example, as described in Pulkkinen and Miller, J. Bacteriol., 1991: 173 (1): 86-93; and Alpuche-Aranda et al., PNAS, 1992; 89(21): 10079-83), a nirB promoter (for example, as described in Harborne et al. (1992) Mol. Micro. 6:2805-2813; Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (for example, GenBank Accession Nos. AX798980, AX798961, and AX798183); a stationary phase promoter, e.g., a dps promoter, an spy promoter; a promoter derived from the pathogenicity island SPI-2 (for example, as described in WO96/17951); an actA promoter (for example, as described in Shetron-Rama et al. (2002) Infect. Immun. 70:1087-1096); an rpsM promoter (for example, as described in Valdivia and Falkow (1996). Mol. Microbiol. 22:367-378); a tet promoter (for example, as described in Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); and an SP6 promoter (for example, as described in Melton et al. (1984) Nucl. Acids Res. 12:7035-7056).

In yeast, a number of vectors containing constitutive or inducible promoters may be used. For a review of such vectors see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (for example, as described in Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A vector utilized in the practice of the disclosure also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, and sequences that encode a selectable marker. As such, the vector can contain, for example, one or more cloning sites such as a multiple cloning site, which can, but need not be positioned such that a exogenous or endogenous polynucleotide can be inserted into the vector and operatively linked to a desired element. The vector also can contain a prokaryote origin of replication (ori), for example, an *E. coli* ori or a cosmid ori, thus allowing passage of the vector into a prokaryote host cell, as well as into a plant chloroplast.

A regulatory element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IRES. Additionally, a cell compartmentalization signal (i.e., a sequence that targets a polypeptide to the cytosol, nucleus, chloroplast membrane or cell membrane). In some aspects of the present disclosure, a cell compartmentalization signal (e.g., a cell membrane targeting sequence) may be ligated to a gene and/or transcript, such that translation of the gene occurs in the chloroplast. In other aspects, a cell compartmentalization signal may be ligated to a gene such that, following translation of the gene, the protein is transported to the cell membrane.

A vector, or a linearized portion thereof, may include a nucleotide sequence encoding a reporter polypeptide or other selectable marker. The term "reporter" or "selectable marker" refers to a polynucleotide (or encoded polypeptide) that confers a detectable phenotype, A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (for example, as described in Giacomin, *Plant Sci.* 116:59-72, 1996; Scikantha, *J. Bacteriol.* 178:121, 1996; Gerdes, *FEBS Lett.* 389:44-47, 1996; and Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain, for example, prokaryotic cells or plant cells or both that express the marker and, therefore, can be useful as a component of a vector of the disclosure. One class of selectable markers are native or modified genes which restore a biological or physiological function to a host cell (e.g., restores photosynthetic capability or restores a metabolic pathway). Other examples of selectable markers include, but are not limited to, those that confer antimetabolite resistance, for example, dihydrofolate reductase, which confers resistance to methotrexate (for example, as described in Reiss, *Plant Physiol.* (*Life Sci. Adv.*) 13:143-149, 1994); neomycin phosphotransferase, which confers resistance to the aminoglycosides neomycin, kanamycin and paromycin (for example, as described in Herrera-Estrella, *EMBO J.* 2:987-995, 1983), hygro, which confers resistance to hygromycin (for example, as described in Marsh, *Gene* 32:481-485, 1984), trpB, which allows cells to utilize indole in place of tryptophan; hisD, which allows cells to utilize histinol in place of histidine (for example, as described in Hartman, *Proc. Natl. Acad. Sci., USA* 85:8047, 1988); mannose-6-phosphate isomerase which allows cells to utilize mannose (for example, as described in PCT Publication Application No. WO 94/20627); ornithine decarboxylase, which confers resistance to the ornithine decarboxylase inhibitor, 2-(difluoromethyl)-DL-ornithine (DFMO; for example, as described in McConlogue, 1987, In: Current Communications in Molecular Biology, Cold Spring Harbor Laboratory ed.); and deaminase from *Aspergillus terreus*, which confers resistance to Blasticidin S (for example, as described in Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (for example, as described in White et al., *Nucl. Acids Res.* 18:1062, 1990; and Spencer et al., *Theor. Appl. Genet.* 79:625-631, 1990), a mutant EPSPV-synthase, which confers glyphosate resistance (for example, as described in Hinchee et al., *BioTechnology* 91:915-922, 1998), a mutant acetolactate synthase, which confers imidazolione or sulfonylurea resistance (for example, as described in Lee et al., *EMBO J.* 7:1241-1248, 1988), a mutant psbA, which confers resistance to atrazine (for example, as described in Smeda et al., *Plant Physiol.* 103:911-917, 1993), or a mutant protoporphyrinogen oxidase (for example, as described in U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells; ampicillin resistance for prokaryotes such as *E. coli*; and bleomycin, gentamycin, glyphosate, hygronmycin, kanamycin, methotrexate, phleomycin, phosphinotricin, spectinomycin, streptomycin, sulfonamide and sulfonylurea resistance in plants (for example, as described in Maliga et al., Methods in Plant Molecular Biology, Cold Spring Harbor Laboratory Press, 1995, page 39).

Reporter genes have been successfully used in chloroplasts of higher plants, and high levels of recombinant protein expression have been reported. In addition, reporter genes have been used in the chloroplast of *C. reinhardtii*. Reporter genes greatly enhance the ability to monitor gene expression in a number of biological organisms. In chloroplasts of higher plants, β-glucuronidase (uidA, for example, as described in Staub and Maliga, *EMBO J.* 12:601-606, 1993), neomycin phosphotransferase (nptII, for example, as described in Carrer et al., *Mol. Gen. Genet.* 241:49-56, 1993), adenosyl-3-adenyltransf-erase (aadA, for example, as described in Svab and Maliga, *Proc. Natl. Acad. Sci.*, USA 90:913-917, 1993), and the *Aequorea victoria* GFP (for example, as described in Sidorov et al., *Plant J.* 19:209-216, 1999) have been used as reporter genes (for example, as described in Heifetz, *Biochemie* 82:655-666, 2000). Each of these genes has attributes that make them useful reporters of chloroplast gene expression, such as ease of analysis, sensitivity, or the ability to examine expression in situ. Based upon these studies, other exogenous proteins have been expressed in the chloroplasts of higher plants such as *Bacillus thuringiensis* Cry toxins, conferring resistance to insect herbivores (for example, as described in Kota et al., *Proc. Natl. Acad. Sci.*, USA 96:1840-1845, 1999), or human somatotropin (for example, as described in Staub et al., *Nat. Biotechnol.* 18:333-338, 2000), a potential biopharmaceutical. Several reporter genes have been expressed in the chloroplast of the eukaryotic green alga, *C. reinhardtii*, including aadA (for example, as described in Goldschmidt-Clermont, *Nucl. Acids Res.* 19:4083-4089 1991; and Zerges and Rochaix, *Mol. Cell Biol.* 14:5268-5277, 1994), uidA (for example, as described in Sakamoto et al., *Proc. Nat. Acad. Sci.*, USA 90:477-501, 1993; and Ishikura et al., *J. Biosci. Bioeng.* 87:307-314 1999), *Renilla* luciferase (for example, as described in Minko et al., *Mol. Gen. Genet.* 262:421-425, 1999) and the amino glycoside phosphotransferase from *Acinetobacter baumnanii*, aphA6 (for example, as described in Bateman and Purton, *Mol. Gen. Genet.* 263:404-410, 2000).

In some instances, the vectors of the present disclosure will contain elements such as an *E. coli* or *S. cerevisiae* origin of replication. Such features, combined with appropriate selectable markers, allows for the vector to be "shuttled" between the target host cell and a bacterial and/or yeast cell. The ability to passage a shuttle vector of the disclosure in a secondary host may allow for more convenient manipulation of the features of the vector. For example, a reaction mixture containing the vector and putative inserted polynucleotides of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant cell chloroplasts, wherein a polypeptide of interest can be expressed and, if desired, isolated according to a method of the disclosure.

Knowledge of the chloroplast or nuclear genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, *J. Mol. Biol.* 312:425-438, 2001; Staub and Maliga, *Plant Cell* 4:39-45, 1992; and Kavanagh et al., *Genetics* 152:1111-1122, 1999, each of which is incorporated herein by reference). The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link; J. Maul, J. W. Lilly, and D. B. Stern, unpublished results; revised Jan. 28, 2002; to be published as GenBank Acc. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast, In this respect, the website containing the *C. reinhardtii* chloroplast genome sequence also provides maps showing coding and non-coding regions of the chloroplast genome, thus facilitating selection of a sequence useful for constructing a vector (also described in Maul, J. E., et al. (2002) The Plant Cell, Vol. 14 (2659-2679)). For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chlorol40.html").

The entire nuclear genome of *C. reinhardtii* is described in Merchant, S. S., et al., Science (2007), 318(5848):245-250, thus facilitating one of skill in the art to select a sequence or sequences useful for constructing a vector.

For expression of the polypeptide in a host, an expression cassette or vector may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous or endogenous proteins. A selectable marker operative in the expression host may be present.

The description herein provides that host cells may be transformed with vectors. One of skill in the art will recognize that such transformation includes transformation with circular or linearized vectors, or linearized portions of a vector. Thus, a host cell comprising a vector may contain the entire vector in the cell (in either circular or linear form), or may contain a linearized portion of a vector of the present disclosure. In some instances 0.5 to 1.5 kb flanking nucleotide sequences of chloroplast genomic DNA may be used. In some instances 0.5 to 1.5 kb flanking nucleotide sequences of nuclear genomic DNA may be used, or 2.0 to 5.0 kb may be used.

Production of Products or Compounds

The modified host organisms disclosed herein are useful in the production of a desired compound or product. Compounds and products are used interchangeably throughout the disclosure. The present disclosure provides methods of producing, for example, an isoprenoid or isoprenoid precursor compound in a host cell. One such method involves, culturing a modified host cell in a suitable culture medium under conditions that promote synthesis of a product, for example, an isoprenoid compound or isoprenoid precursor compound, where the isoprenoid compound is generated by the expression of a variant enzyme of the present disclosure, wherein the variant enzyme uses a substrate present in the host cell. In some embodiments, a method further comprises isolating the isoprenoid compound from the cell and/or from the culture medium.

In some embodiments, the compound, for example, an isoprenoid or isoprenoid compound is produced in a genetically modified host cell at a level that is at least about 2-fold, at least about 5-fold, at least about 10-fold, at least about 25-fold, at least about 50-fold, at least about 100-fold, at least about 500-fold, at least about 1000-fold, at least about 2000-fold, at least about 3000-fold, at least about 4000-fold, at least about 5000-fold, or at least about 10,000-fold, or more, higher than the level of the isoprenoid or isoprenoid precursor compound produced in an unmodified host cell that produces the isoprenoid or isoprenoid precursor compound via the same biosynthetic pathway.

In some embodiments, a genetically modified host cell is cultured in a suitable medium (e.g., Luria-Bertoni broth, optionally supplemented with one or more additional agents, such as an inducer (e.g., where the variant isoprenoid synthase is under the control of an inducible promoter); and the culture medium is overlaid with an organic solvent, e.g. dodecane, forming an organic layer. The compound produced by the genetically modified host partitions into the organic layer, from which it can then be purified. In some embodiments, where a variant prenyl transferase, isoprenoid synthase or mevalonate synthesis-encoding nucleotide sequence is operably linked to an inducible promoter, an inducer is added to the culture medium; and, after a suitable time, the isoprenoid compound is isolated from the organic layer overlaid on the culture medium.

In some embodiments, the compound or product, for example, an isoprenoid compound will be separated from other products which may be present in the organic layer. Separation of the compound from other products that may be present in the organic layer is readily achieved using, e.g., standard chromatographic techniques.

In some embodiments, the compound, for example, an isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure. "Pure" in the context of an isoprenoid compound refers to an isoprenoid compound that is free from other isoprenoid compounds, portions of compounds, contaminants, and unwanted byproducts, for example.

Examples of products contemplated herein include hydrocarbon products and hydrocarbon derivative products. A hydrocarbon product is one that consists of only hydrogen molecules and carbon molecules. A hydrocarbon derivative product is a hydrocarbon product with one or more heteroatoms, wherein the heteroatom is any atom that is not hydrogen or carbon. Examples of heteroatoms include, but are not limited to, nitrogen, oxygen, sulfur, and phosphorus. Some products can be hydrocarbon-rich, wherein, for example, at least 50%, at least 60%, at least 70%, at least 80%, at least 90%, or at least 95% of the product by weight is made up of carbon and hydrogen.

One exemplary group of hydrocarbon products are isoprenoids. Isoprenoids (including terpenoids) are derived from isoprene subunits, but are modified, for example, by the addition of heteroatoms such as oxygen, by carbon skeleton rearrangement, and by alkylation. Isoprenoids generally have a number of carbon atoms which is evenly divisible by five, but this is not a requirement as "irregular" terpenoids are known to one of skill in the art. Carotenoids, such as carotenes and xanthophylls, are examples of isoprenoids that are useful products. A steroid is an example of a terpenoid. Examples of isoprenoids include, but are not limited to, hemiterpenes (C5), monoterpenes (C10), sesquiterpenes (C15), diterpenes (C20), triterpenes (C30), tetraterpenes (C40), polyterpenes ($C_n$, wherein "n" is equal to or greater than 45), and their derivatives. Other examples of isoprenoids include, but are not limited to, limonene, 1,8-cineole, α-pinene, camphene, (+)-sabinene, myrcene, abietadiene, taxadiene, farnesyl pyrophosphate, fusicoccadiene, amorphadiene, (E)-α-bisabolene, zingiberene, or diapophytoene, and their derivatives.

Useful products include, but are not limited to, terpenes and terpenoids as described above. An exemplary group of terpenes are diterpenes (C20). Diterpenes are hydrocarbons that can be modified (e.g. oxidized, methyl groups removed, or cyclized); the carbon skeleton of a diterpene can be rearranged, to form, for example, terpenoids, such as fusicoccadiene. Fusicoccadiene may also be formed, for example, directly from the isoprene precursors, without being bound by the availability of diterpene or GGDP. Genetic modification of organisms, such as algae, by the methods described herein, can lead to the production of fusicoccadiene, for example, and other types of terpenes, such as limonene, for example. Genetic modification can also lead to the production of modified terpenes, such as methyl squalene or hydroxylated and/or conjugated terpenes such as paclitaxel.

Other useful products can be, for example, a product comprising a hydrocarbon obtained from an organism expressing a diterpene synthase. Such exemplary products include ent-kaurene, casbene, and fusicocaccadiene, and may also include fuel additives.

The products produced by the present disclosure may be naturally, or non-naturally (e.g., as a result of transformation) produced by the host cell(s) and/or organism(s) transformed. For example, products not naturally produced by algae may include non-native terpenes/terpenoids such as fusicoccadiene. The host cell may be genetically modified, for example, by transformation of the cell with a sequence encoding a protein, wherein expression of the protein results in the secretion of a non-naturally produced product or products.

Examples of useful products include petrochemical products and their precursors and all other substances that may be useful in the petrochemical industry. Products include, for example, petroleum products, precursors of petroleum, as well as petrochemicals and precursors thereof. The fuel or fuel products may be used in a combustor such as a boiler, kiln, dryer or furnace. Other examples of combustors are internal combustion engines such as vehicle engines or generators, including gasoline engines, diesel engines, jet engines, and other types of engines. Products described herein may also be used to produce plastics, resins, fibers, elastomers, pharmacuticals, neutraceuticals, lubricants, and gels, for example.

Isoprenoid precursors are generated by one of two pathways; the mevalonate pathway or the methylerythritol phosphate (MEP) pathway (FIG. 2 and FIG. 3). Both pathways generate dimethylallyl pyrophosphate (DMAPP) and isopentyl pyrophosphate (IPP), the common C5 precursor for isoprenoids. The DMAPP and IPP are condensed to form geranyl-diphosphate (GPP), or other precursors, such as farnesyl-diphosphate (FPP) or geranylgeranyl-diphosphate (GGPP), from which higher isoprenoids are formed.

Useful products can also include small alkanes (for example, 1 to approximately 4 carbons) such as methane, ethane, propane, or butane, which may be used for heating (such as in cooking) or making plastics. Products may also include molecules with a carbon backbone of approximately 5 to approximately 9 carbon atoms, such as naptha or ligroin, or their precursors. Other products may be about 5 to about 12 carbon atoms, or cycloalkanes used as gasoline or motor fuel. Molecules and aromatics of approximately 10 to approximately 18 carbons, such as kerosene, or its precursors, may also be useful as products. Other products include lubricating oil, heavy gas oil, or fuel oil, or their precursors, and can contain alkanes, cycloalkanes, or aromatics of approximately 12 to approximately 70 carbons. Products also include other residuals that can be derived from or found in crude oil, such as coke, asphalt, tar, and waxes, generally containing multiple rings with about 70 or more carbons, and their precursors.

Modified organisms can be grown, in some embodiments in the presence of $CO_2$, to produce the variant polypeptide. In some embodiments, the products produced by the modified organism are isolated or collected. Collected products, such as terpenes and terpenoids, may then be further modified, for example, by refining and/or cracking to produce fuel molecules or components.

The various products may be further refined to a final product for an end user by a number of processes. Refining can, for example, occur by fractional distillation. For example, a mixture of products, such as a mix of different hydrocarbons with various chain lengths may be separated into various components by fractional distillation.

Refining may also include any one or more of the following steps, cracking, unifying, or altering the product. Large products, such as large hydrocarbons (e.g. ≥C10), may be broken down into smaller fragments by cracking. Cracking may be performed by heat or high pressure, such as by steam, visbreaking, or coking. Products may also be refined by visbreaking, for example by thermally cracking large hydrocarbon molecules in the product by heating the product in a furnace. Refining may also include coking, wherein a heavy, almost pure carbon residue is produced. Cracking may also be performed by catalytic means to enhance the rate of the cracking reaction by using catalysts such as, but not limited to, zeolite, aluminum hydrosilicate, bauxite, or silica-alumina. Catalysis may be by fluid catalytic cracking, whereby a hot catalyst, such as zeolite, is used to catalyze cracking reactions. Catalysis may also be performed by hydrocracking, where lower temperatures are generally used in comparison to fluid catalytic cracking. Hydrocracking can occur in the presence of elevated partial pressure of hydrogen gas. Products may be refined by catalytic cracking to generate diesel, gasoline, and/or kerosene.

The products may also be refined by combining them in a unification step, for example by using catalysts, such as platinum or a platinum-rhenium mix. The unification process can produce hydrogen gas, a by-product, which may be used in cracking.

The products may also be refined by altering, rearranging, or restructuring hydrocarbons into smaller molecules. There are a number of chemical reactions that occur in catalytic reforming processes which are known to one of ordinary skill in the arts. Catalytic reforming can be performed in the presence of a catalyst and a high partial pressure of hydrogen. One common process is alkylation. For example, propylene and butylene are mixed with a catalyst such as hydrofluoric acid or sulfuric acid, and the resulting products are high octane hydrocarbons, which can be used to reduce knocking in gasoline blends.

The products may also be blended or combined into mixtures to obtain an end product. For example, the products may be blended to form gasoline of various grades, gasoline with or without additives, lubricating oils of various weights and grades, kerosene of various grades, jet fuel, diesel fuel, heating oil, and chemicals for making plastics and other polymers. Compositions of the products described herein may be combined or blended with fuel products produced by other means.

Some products produced from the host cells of the disclosure, especially after refining, will be identical to existing petrochemicals, i.e. contain the same chemical structure. For instance, crude oil contains the isoprenoid pristane, which is thought to be a breakdown product of phytol, which is a component of chlorophyll. Some of the products may not be the same as existing petrochemicals. However, although a molecule may not exist in conventional petrochemicals or refining, it may still be useful in these industries. For example, a hydrocarbon could be produced that is in the boiling point range of gasoline, and that could be used as gasoline or an additive, even though the hydrocarbon does not normally occur in gasoline.

Also disclosed is a method of producing a product, comprising: a) transforming a host with a polynucleotide comprising a nucleic acid encoding a variant enzyme, for example, a variant prenyl transferase or a variant isoprenoid synthase, capable of being expressed in the host, wherein the variant enzyme is involved in isoprenoid production, wherein the transformation results in the expression of the variant enzyme, wherein the host is a photosynthetic bacterium, a yeast, an alga, or a vascular plant; and wherein the variant enzyme has at least one altered property as compared to a parent polypeptide; and b) isolating the product from the transformed host.

Assays for Determining Variant Protein Activity

Methods for screening for various enzyme activities are known to those of skill in the art and are discussed throughout the disclosure.

Screening of products, for example, isoprenoid products may be done using a commercially available kit to detect pyrophosphate released from the substrates (DMAPP & IPP). For example, the EnzCheck kit (Molecular Probes) may be used to measure inorganic pyrophosphate. Alternatively, isoprenoid products may be analyzed using GC/MS procedures well known in the art. The GC/MS methods may be used to detect products following phosphatase treatment (e.g., FPP and GPP are treated to yield farnesol or geraniol). Alternatively, thin layer chromatography methods well known in the art may be used.

A high-throughput assay for quantitating inorganic pyrophosphate in solution, which allows for the straightforward determination of, for example, a prenyl transferase (e.g. FPP synthase, GPP synthase or GGPP synthase) or isoprenoid synthase activity in a multiwell (e.g. 96 or 384 or higher) plate format, can be used. An assay can include, for example: (i) tagging the variant polypeptide with a tag that allows for the purification of the variant polypeptide from a reaction mixture; (ii) reacting the purified variant polypeptide in a isoprenoid producing reaction; (iii) isolating pyrophosphate from the reaction mixture, for example, by removal of the variant polypeptide; and (iv) quantitating the amount of pyrophosphate, where an increase in the amount of pyrophosphate compared to the amount of pyrophosphate generated by a parent polypeptide over a period of time indicates an increased enzyme flux.

For example, the PPiLight kit (Lonza) may be used to determine the amount of inorganic pyrophosphate produced in the isoprenoid synthesis reaction. This method removes the polypeptides from the reaction mixture following the reaction. Thus, prior to running the pyrophosphate detection reaction, the variant polypeptide which has been tagged with an affinity tag is removed by adsorption to the appropriate affinity media.

For example, a FLAG tag, 6×His, Strep-TagII, MBP (maltose binding protein) or other tag may be used. Methods for designing tags are well known in the art. The tag may be attached at the C-terminus, N-terminus or any other region that allows for proper purification without interfering with enzyme activity. For example, the C-terminus of FPP and GPP were tagged using a FLAG tag and shown to retain enzyme activity. By attaching the tag, methods of removing the polypeptide are well known in the art. This assay allows for rapid, high-throughput screening of variant polypeptides for generation of isoprenoid products.

Other assays that can be used to quantitate the pyrophosphate are, for example, the EnzCheck Pyrophosphate Assay kit (Life Technologies) or the PiPer Pyrophosphate Assay Kit (Life Technologies).

The following examples are intended to provide illustrations of the application of the present disclosure. The following examples are not intended to completely define or otherwise limit the scope of the disclosure.

EXAMPLES

Example 1

Production of Variant Polypeptide in C. reinhardtii

In this example a polynucleotide encoding a variant prenyl transferase from A. thaliana (Genbank accession number CAC16849, Table 2) is introduced into C. reinhardtii. Transforming DNA comprises a gene encoding a variant prenyl transferase FPP synthase from A. thaliana, which is regulated by the 5' UTR and promoter sequence for the psbA gene from C. reinhardtii and the 3' UTR for the psbA gene from C. reinhardtii, and a kanamycin resistance encoding gene from bacteria, which is regulated by the 5' UTR and promoter sequence for the atpA gene from C. reinhardtii and the 3' UTR sequence for the rbcL gene from C. reinhardtii. The transgene cassette is targeted to the psbA loci of C. reinhardtii via segments identical to sequences of DNA flanking the psbA locus on the 5' and 3' sides, respectively. All DNA manipulations carried out in the construction of this transforming DNA are essentially as described by Sambrook et al., Molecular Cloning: A Laboratory Manual (Cold Spring Harbor Laboratory Press 1989) and Cohen et al., Meth. Enzymol. 297, 192-208, 1998.

For these experiments, all transformations are carried out on C. reinhardtii strain 137c (mt+). Cells are grown to late log phase (approximately 7 days) in the presence of 0.5 mM 5-fluorodeoxyuridine in TAP medium (Gorman and Levine, Proc. Natl. Acad. Sci., USA 54:1665-1669, 1965, which is incorporated herein by reference) at 23° C. under constant illumination of 450 Lux on a rotary shaker set at 100 rpm. Fifty ml of cells are harvested by centrifugation at 4,000×g at 23° C. for 5 min. The supernatant is decanted and cells resuspended in 4 ml TAP medium for subsequent chloroplast transformation by particle bombardment (Cohen et al., Meth. Enzymol. 297, 192-208, 1998). All transformations are carried out under kanamycin selection (100 µg/ml). (Chlamydomonas Stock Center, Duke University).

PCR is used to identify transformed strains. For PCR analysis, $10^6$ algae cells (from agar plate or liquid culture) are suspended in 10 mM EDTA and heated to 95° C. for 10 minutes, then cooled to near 23° C. A PCR cocktail consisting of reaction buffer, MgCl2, dNTPs, PCR primer pair(s), DNA polymerase, and water is prepared. Algae lysate in EDTA is added to provide template for reaction. Magnesium concentration is varied to compensate for amount and concentration of algae lysate in EDTA added. Annealing temperature gradients are employed to determine optimal annealing temperature for specific primer pairs.

To identify strains that contain the variant prenyl transferase gene, a primer pair is used in which one primer anneals to a site within the psbA 5'UTR and the other primer anneals within the variant prenyl transferase coding segment. Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector and consists of a primer that anneals within the psbA 5'UTR and one that anneals within the psbA coding region. The second pair of primers amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used is >30 to increase sensitivity.

Cultivation of C. reinhardtii transformants for expression of variant prenyl transferase is carried out in liquid TAP medium at 23° C. in the dark on a rotary shaker set at 100 rpm, unless stated otherwise. Cultures are maintained at a density of $1 \times 10^7$ cells per ml for at least 48 hr prior to harvest.

To determine if the variant prenyl transferase gene led to expression of the variant prenyl transferase in transformed algae cells, both soluble proteins are immunoprecipitated and visualized by Western blot. Briefly, 500 ml of algae cell culture is harvested by centrifugation at 4000×g at 4° C. for 15 min. The supernatant is decanted and the cells resuspended in 10 ml of lysis buffer (100 mM Tris-HCl, pH==8.0, 300 mM NaCl, 2% Tween-20). Cells are lysed by sonication (10×30 sec at 35% power). Lysate is clarified by centrifugation at 14,000×g at 4° C. for 1 hour. The supernatant is removed and incubated with anti-FLAG antibody-conjugated agarose resin at 4° C. for 10 hours. Resin is separated from the lysate by gravity filtration and washed 3× with wash buffer ((100 mM Tris-HCl, pH=8.0, 300 mM NaCl, 2% Tween-20).

Example 2

Mutagenesis of Prenyl Transferase Using Directed Mutagenesis

Generation of Random Size Polynucleotides Using U.V. Induced Photoproducts

One microgram samples of template DNA are obtained and treated with U.V. light to cause the formation of dimers, including TT dimers, for example, purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

Isolation of Random Size Polynucleotides

Polynucleotides of interest which are generated according to the protocol above are gel isolated on a 1.5% agarose gel. Polynucleotides in the 100-300 bp range are cut out of the gel and 3 volumes of 6 M NaI is added to the gel slice. The mixture is incubated at 50° C. for 10 minutes and 10 µl of glass milk (Bio 101) is added. The mixture is spun for 1 minute and the supernatant is decanted. The pellet is washed with 500 µl of Column Wash (Column Wash is 50% ethanol, 10 mM Tris-HCl pH 7.5, 100 mM NaCl and 2.5 mM EDTA) and spin for 1 minute, after which the supernatant is decanted. The washing, spinning and decanting steps are then repeated. The glass milk pellet is resuspended in 20 µl of $H_2O$ and spun for 1 minute. DNA remains in the aqueous phase.

Shuffling of Isolated Random Size 100-300 bp Polynucleotides

The 100-300 bp polynucleotides obtained above are recombined in an annealing mixture (0.2 mM each dNTP, 2.2 mM $MgCl_2$, 50 mM KCl, 10 mM Tris-HCl ph 8.8, 0.1% Triton X-100, 0.3 µl Taq DNA polymerase, 50 µl total volume) without adding primers. A Robocycler by Stratagene is used for the annealing step with the following program: 95° C. for 30 seconds, 25-50 cycles of (95° C. for 30 seconds, 50-60° C. (for example, 58° C.) for 30 seconds, and 72° C. for 30 seconds) and 5 minutes at 72° C. Thus, the 100-300 bp polynucleotides combine to yield double-stranded polynucleotides having a longer sequence. After separating out the reassembled double-stranded polynucleotides and denaturing them to form single stranded polynucleotides, the cycling is optionally again repeated with some samples utilizing the single strands as template and primer DNA and other samples utilizing random primers in addition to the single strands.

Screening of Polypeptides from Shuffled Polynucleotides

The polynucleotides generated above are separated and polypeptides are expressed there from. The original template DNA is utilized as a comparative control by obtaining comparative polypeptides there from. The polypeptides obtained from the shuffled polynucleotides above are screened for the activity of the polypeptides obtained from the original template and compared with the activity levels of the control. The shuffled polynucleotides coding for interesting polypeptides discovered during screening are compared further for secondary desirable traits. Some shuffled polynucleotides corresponding to less interesting screened polypeptides are subjected to reshuffling.

Directed Evolution an Enzyme by Saturation Mutagenesis

Site-Saturation Mutagenesis: To accomplish site-saturation mutagenesis every residue of a prenyl transferase enzyme is converted into all 20 amino acids by site directed mutagenesis using 32-fold degenerate oligonucleotide primers, as follows: 1. A culture of the prenyl transferase expression construct is grown and a preparation of the plasmid is made; 2. Primers are made to randomize each codon—they have the common structure $X_{20}$ NN(G/T)$X_{20}$; and 3. A reaction mix of 25 µl is prepared containing about 50 ng of plasmid template, 125 ng of each primer, 1× native Pfu buffer, 200 uM each dNTP and 2.5 U native Pfu DNA polymerase 4. The reaction is cycled in a Robo96 Gradient Cycler as follows: Initial denaturation at 95° C. for 1 min cycles of 95° C. for 45 sec, 53° C. for 1 min and 72° C. for 11 min Final elongation step of 72° C. for 10 min 5. The reaction mix is digested with 10 U of DpnI at 37° C. for 1 hour to digest the methylated template DNA 6. Two µl of the reaction mix are used to transform 50 µl of XL1-Blue MRF' cells and the entire transformation mix is plated on a large LB-Amp-Met plate yielding 200-1000 colonies 7. Individual colonies are tooth picked into the wells of 96-well microtiter plates containing LB-Amp-IPTG and grown overnight 8. The clones on these plates are assayed the following day.

Example 3

Mutagenesis of Prenyl Transferase Using DNA Shuffling

The minimum inhibitory concentration (MIC) of cefotaxime on bacterial cells lacking a plasmid is determined by plating 10 µl of a $10^{-2}$ dilution of an overnight bacterial culture (about 1000 cfu) of *E. coli* XL1-blue cells (Stratagene, San Diego Calif.) on plates with varying levels of cefotaxime (Sigma, St. Louis Mo.), followed by incubation for 24 hours at 37° C.

Growth on cefotaxime is sensitive to the density of cells, and therefore similar numbers of cells needed to be plated on each plate (obtained by plating on plain LB plates). Platings of 1000 cells are consistently performed.

Initial Plasmid Construction

A pUC18 derivative carrying the prenyl transferase is used. The prenyl transferase gene confers resistance to bacteria, against approximately 0.02 µg/ml of cefotaxime. SfiI restriction sites are added 5' of the promoter and 3' of the end of the gene by PCR of the vector sequence with two primers:

```
Exemplary Primer A (SEQ ID NO: 25):
5'TTCTATTGACGGCCTGTCAGGCCTCATATATACTTTAGATTGATTT3'
and Exemplary Primer B (SEQ ID NO: 26):
5'TTGACGCACTGGCCATGGTGGCCAAAAATAAACAAATAGGGGTTCCGCGCACATTT3'
``` and by PCR of the betalactamase gene sequence with two other primers:

```
Exemplary Primer C (SEQ ID NO: 27):
5'AACTGACCACGGCCTGACAGGCCGGTCTGACAGTTACCAATGCTT,
and Exemplary Primer D (SEQ ID NO: 28):
5'AACCTGTCCTGGCCACCATGGCCTAAATACATTCAAATATGTAT.
```

The two reaction products are digested with SfiI, mixed, ligated and used to transform bacteria.

The substrate for the first shuffling reaction is dsDNA of 0.9 kb obtained by PCR of pUC182Sfi with primers C and D, both of which contain a SfiI site.

The free primers from the PCR product are removed by Wizard PCR prep (Promega, Madison Wis.) at every cycle.

About 5 µg of the DNA substrate(s) is digested with 0.15 units of DNAseI (Sigma, St. Louis Mo.) in 100 µl of 50 mM Tris-HCl pH 7.4, 1 mM MgCl$_2$, for 10 min at room temperature. Fragments of 100-300 bp are purified from 2% low melting point agarose gels by electrophoresis onto DE81 ion exchange paper (Whatman, Hillsborough Oreg.), elution with 1 M NaCl and ethanol precipitation.

Gene Shuffling

The purified fragments are resuspended in PCR mix (0.2 mM each dNTP, 2.2 mM MgCl$_2$, 50 mM KCl, 10 mM Tris-HCl pH 9.0, 0.1% Triton X-100), at a concentration of 10-30 ng/µl. No primers are added at this point. A reassembly program of 94° C. for 60 seconds, then 40 cycles of (94° C. for 30 seconds, 50-55° C. for 30 seconds, 72° C. for 30 seconds) and then 72° C. for minutes is used in an MJ Research (Watertown Mass.) PTC-150 thermocycler.

Amplification of Reassembly Product with Primers

After dilution of the reassembly product into the PCR mix with 0.8 µM of each primer (C and D) and 20 PCR cycles (94° C. for 30 seconds, 50° C. for 30 seconds, 72° C. for 30 seconds) a single product 900 bp in size is obtained.

Cloning and Analysis

After digestion of the 900 bp product with the terminal restriction enzyme SfiI and agarose gel purification, the 900 bp product is ligated into the vector pUC182Sfi at the unique SfiI site with T4 DNA ligase (BRL, Gaithersburg Md.). The mixture is electroporated into *E. coli* XL1-blue cells and plated on LB plates with 0.32-0.64 µg/ml of cefotaxime (Sigma, St. Louis Mo.). The cells were grown for up to 24 hours at 37° C. and the resulting colonies are scraped off the plate as a pool and used as the PCR template for the next round of shuffling.

Subsequent Reassembly Rounds

The transformants obtained after each of three rounds of shuffling are plated on increasing levels of cefotaxime. The colonies (>100, to maintain diversity) from the plate with the highest level of cefotaxime are pooled and used as the template for the PCR reaction for the next round.

A mixture of the cefotaxime colonies obtained at 0.32-0.64 µg/ml in the Cloning and Analysis step above are used as the template for the next round of shuffling. 10 ul of cells in LB broth are used as the template in a reassembly program of 10 minutes at 99° C., then 35 cycles of (94° C. for 30 seconds, 52° C. for 30 seconds, 72° C. for 30 seconds) and then 5 minutes at 72° C. as described above.

The reassembly products are digested and ligated into pUC182Sfi as described in the Cloning and Analysis step above. The mixture is electroporated into *E. coli* XL1-blue cells and plated on LB plates having 5-10 µg/ml of cefotaxime.

Colonies obtained at 5-10 µg/ml are used for a third round similar to the first and second rounds except the cells are plated on LB plates having 80-160 µg/ml of cefotaxime. After the third round, colonies are obtained at 80-160 µg/ml, and after replating on increasing concentrations of cefotaxime, colonies could be obtained at up to 320 µg/ml after 24 hours at 37° C. (MIC=320 µg/ml).

Growth on cefotaxime is dependent on the cell density, requiring that all the MICs be standardized (in our case to about 1,000 cells per plate). At higher cell densities, growth at up to 1280 µg/ml is obtained. The 5 largest colonies grown at 1,280 µg/ml are plated for single colonies twice, and the SfiI inserts are analyzed by restriction mapping of the colony PCR products.

One mutant is obtained with a 16,000 fold increased resistance to cefotaxime (MIC=0.02 µg/ml to MIC=320 µg/ml).

After selection, the plasmid of selected clones is transferred back into wild-type *E. coli* XL1-blue cells (Stratagene, San Diego Calif.) to ensure that none of the measured drug resistance is due to chromosomal mutations.

Example 4

Mutagenesis of Prenyl Transferase Using Look-Through Mutagenesis

In this example, the improved look-through mutagenesis of a prenyl transferase is described.

Look-through mutagenesiscan be applied to identify variants of a protein, for example an enzyme that has increased activity, thermal stability, or some other desired improvement over the native or parent enzyme. The purpose of look-through mutagenesis (LTM) is to introduce selected substitutions at targeted positions in a region of a polypeptide, e.g., the substrate binding regions of a prenyl transferase. Look-through mutagenesis can be applied to either an entire protein, or to selected regions of a protein. In this example, LTM is applied to a prenyl transferase in order to identify variant proteins that have higher activity, as measured by product produced in a standard reaction. This method for mutagenesis using PCR based gene assembly is described in detail in Rajpal, et al. (2005), PNAS 102(24): 8466-8471.

The native sequence of *Gallus gallus* FPP synthase (Genbank Accession No. P08836) (SEQ ID NO: 1) was used as the native or parent sequence (FPPS). The native sequence was codon-optimized for the nuclear genome of *Chlamydomonas* (SEQ ID NO: 21). This gene is 1.2 kb long, and was synthesized using 53 oligonucleotides. Each oligonucleotide is comprised of 63 nucleotides, 21 constant native sequence nucleotides, followed by 21 nucleotides that are varied to encode the mutant sequences, followed by 21 constant native sequence nucleotides. The two native regions of sequential oligonucleotides anneal together, and thermostable polymerases are used to complete the synthesis of the gene as described. Three regions of the native FPPS protein sequence (SEQ ID NO: 1) were selected for treatment by LTM. The regions are amino acid residues 93-141; residues 163-202, and residues 247-295. These three regions were selected through examination of the enzyme's three dimensional structure (as described in Tarshis, et al. (1994), Biochemistry 33(36):10871-10877; and the three dimensional structure from the Protein Data Bank, PDB ID 1FPS) as regions expected to be involved in substrate binding, product release, and/or catalysis.

In order to synthesize the FPPS gene, 1240 oligonucleotides were synthesized, encoding the entire wild type or parent gene, and 20 mutagenesis windows (region one, residues 93-141, is encoded by seven windows of seven amino acids; region two, residues 163-202, is encoded by six windows of seven amino acids, and region three, residues 247-295, is encoded by seven windows of seven amino acids).

For the mutagenesis windows, each oligonucleotide encodes one amino acid as a mutant. At each position, the wild type sequence is mutated to glycine, serine, histidine, leucine, proline, tyrosine, aspartic acid, glutamine, and lysine in the individual mutants. Each pool of 63 variants, therefore, is composed of these nine variants at each position over a seven amino acid window.

These oligonucleotides were used in a series of PCR reactions to assemble the libraries of variant FPP synthases. Sequential PCR reactions were run to assemble the mutant libraries in regions 1, 2, and 3 along with the remainder of the constant, wild type nucleic acid sequence, according to the method of Reisinger, et al. (2007) Nature Protocols 1:2596-2603. An oligonucleotide encoding the bacteriophage T7 promoter was included in the PCR primer encoding the 5' end of the synthesized gene (according to instructions from New England Biolabs for use with the PURExpress in vitro protein synthesis kit (New England Biolabs, Ipswich, Mass.)). Also included in the primer was a nucleic acid sequence encoding a Strep-Tag (WSHPQFEK) useful for protein purification (using the Streptactin system, IBA GmbH, Goettingen, Germany).

After gene assembly was completed, the NEB PURExpress in vitro protein synthesis kit was used according to the manufacturer's instructions to produce the variant FPP synthase proteins. After protein synthesis, Strep-Tag magnetic beads (IBA GmbH) were used to isolate the synthesized proteins, after washing the beads with assay buffer (25 mm HEPES pH 7.4, 10 mM $MgCl_2$).

Figure 7:
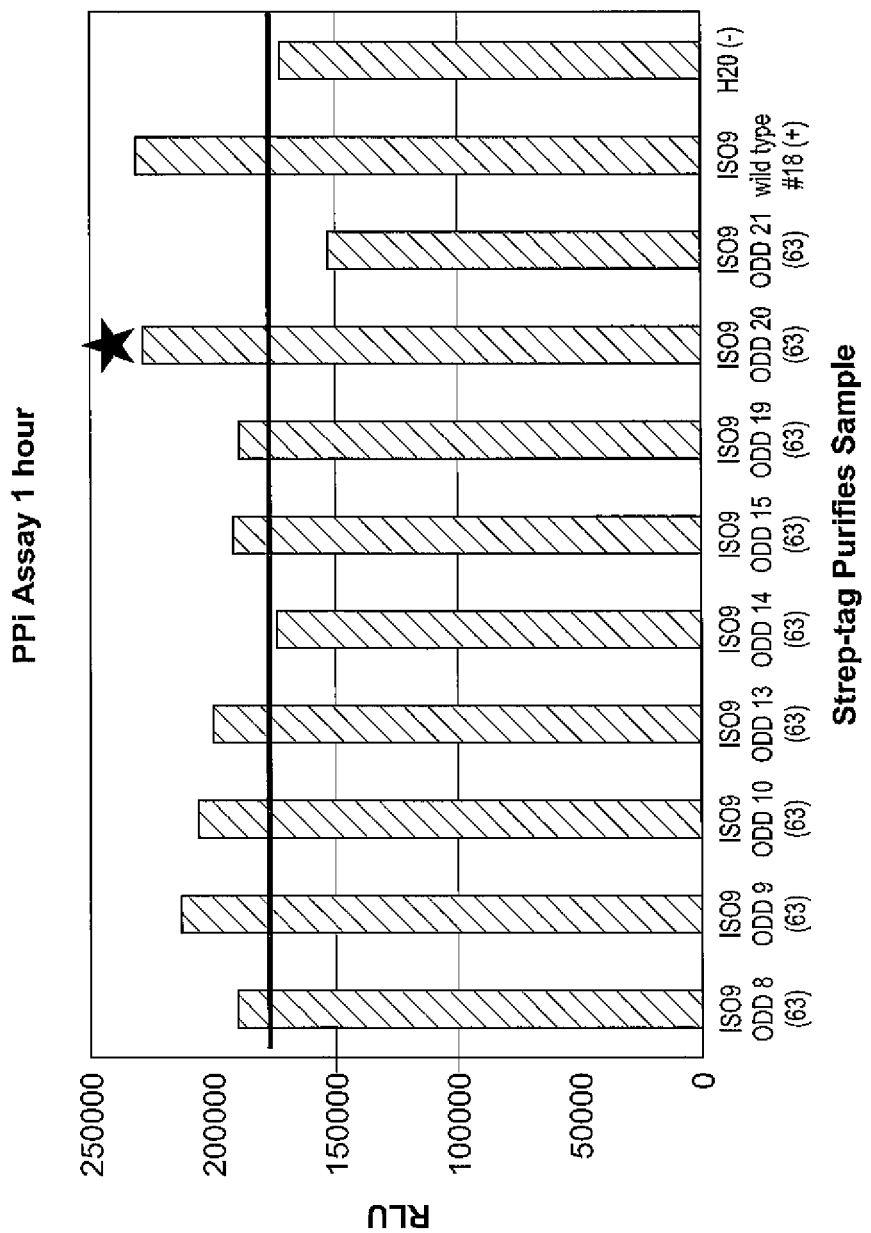
FIG. 7 shows the activity levels, as measured by luminescence, of 9 pools of 63 variant prenyl transferases.

After synthesis, the activity level of the synthesized protein was measured as described in Example 5 by luminescence. Pools of 63 variants with similar activity were identified as shown in FIG. 7. Because most mutations are anticipated to be detrimental, it is unlikely for any pool of mutants to have a higher activity than the wild-type protein; pools with higher activity than average must be deconvoluted to identify individual beneficial mutants.

Figure 8:
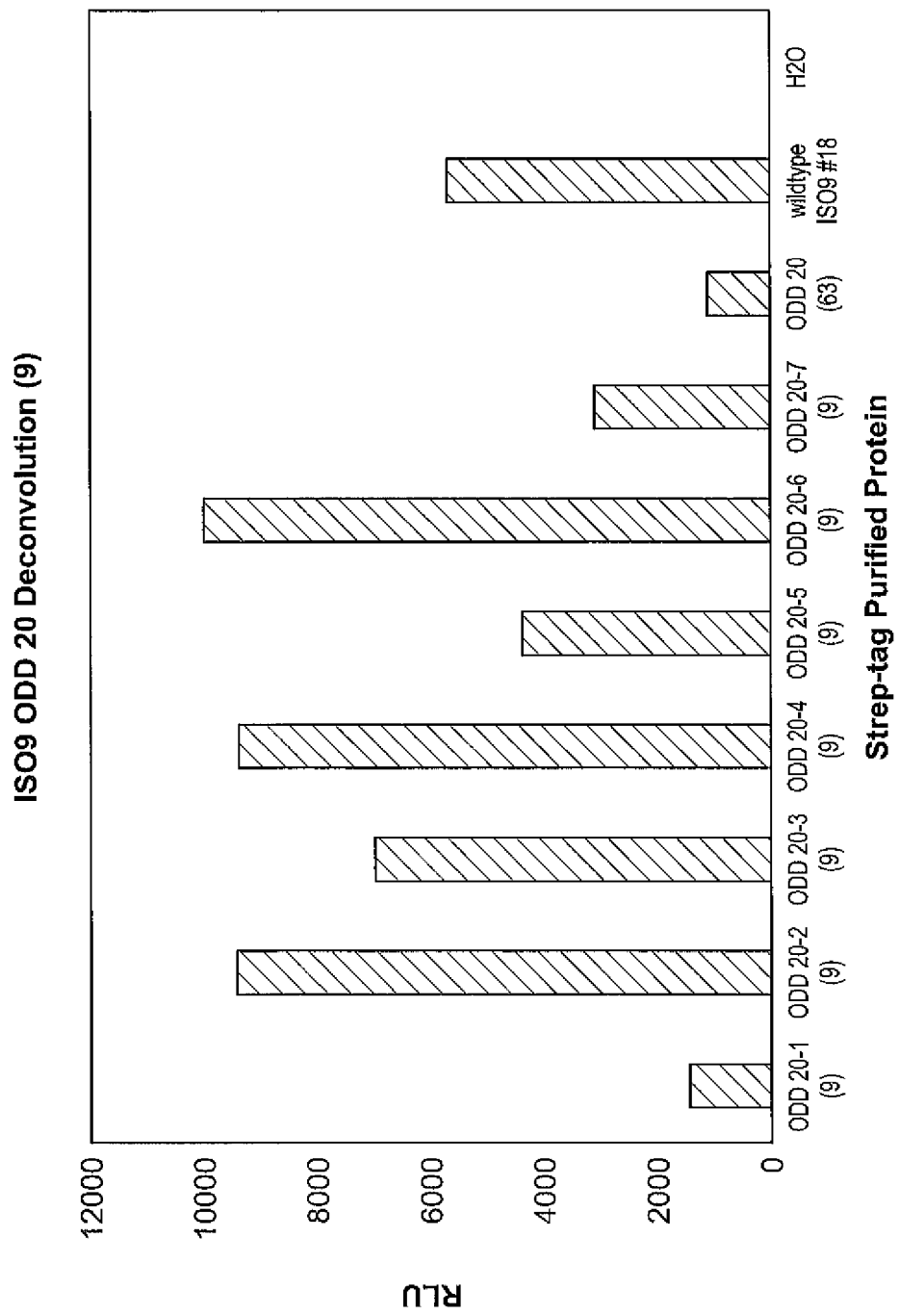
FIG. 8 shows the activity levels, as measured by luminescence, of 7 pools of variant prenyl transferases, each containing 9 variants of an individual amino acid residue.

After pools containing comparable activity were identified, the 63 member pool is resynthesized into seven pools, each containing the nine variants of an individual amino acid residue. The activity of these pools are again measured, and individual pools with activity greater than wild type are identified (FIG. 8). The residue numbers are reported using the wild-type sequence numbering (SEQ ID NO: 1). The winning pools of nine variants are again resynthesized as discrete mutants and activity measurements are repeated. At this point, individual beneficial mutations were identified (FIG. 9), such as Thr_269_Tyr; Thr_269_Asp; or Thr_269_Gln, all of which have more activity than the wild type protein sequence in this assay.

Example 5

Detection of Prenyltransferase Activity by Luminescence Measurement

This example describes the detection of prenyl transferase activity by luminescence measurement. In this example, an avian FPP synthase (Genbank Accession No. P08836) (SEQ ID NO: 1) was used as the parent prenyl transferase. The parent prenyl transferase was codon-optimized (SEQ ID NO: 21) and inserted into a vector. The nucleic acid sequence of SEQ ID NO: 22 was cloned into the bacterial expression vector pET-21a(+) (FIG. 10) under the control of a T7 promoter. A reaction buffer was produced by mixing 4 µl of 10× reaction buffer (250 mM HEPES pH 7.4, 100 mM $MgCl_2$), 0.2 µl of 1M dithiothreitol, 1 µl of 10 mM DMAPP, 2 µl of 10 mM IPP, and 31.8 µl of water. 1 ng of the Avian FPP synthase (SEQ ID NO: 22) was added to the 39 µl of reaction buffer in a white 96 well microplate. The reaction was sealed with an adhesive plastic cover and allowed to progress for two hours at room temperature.

Figure 9:
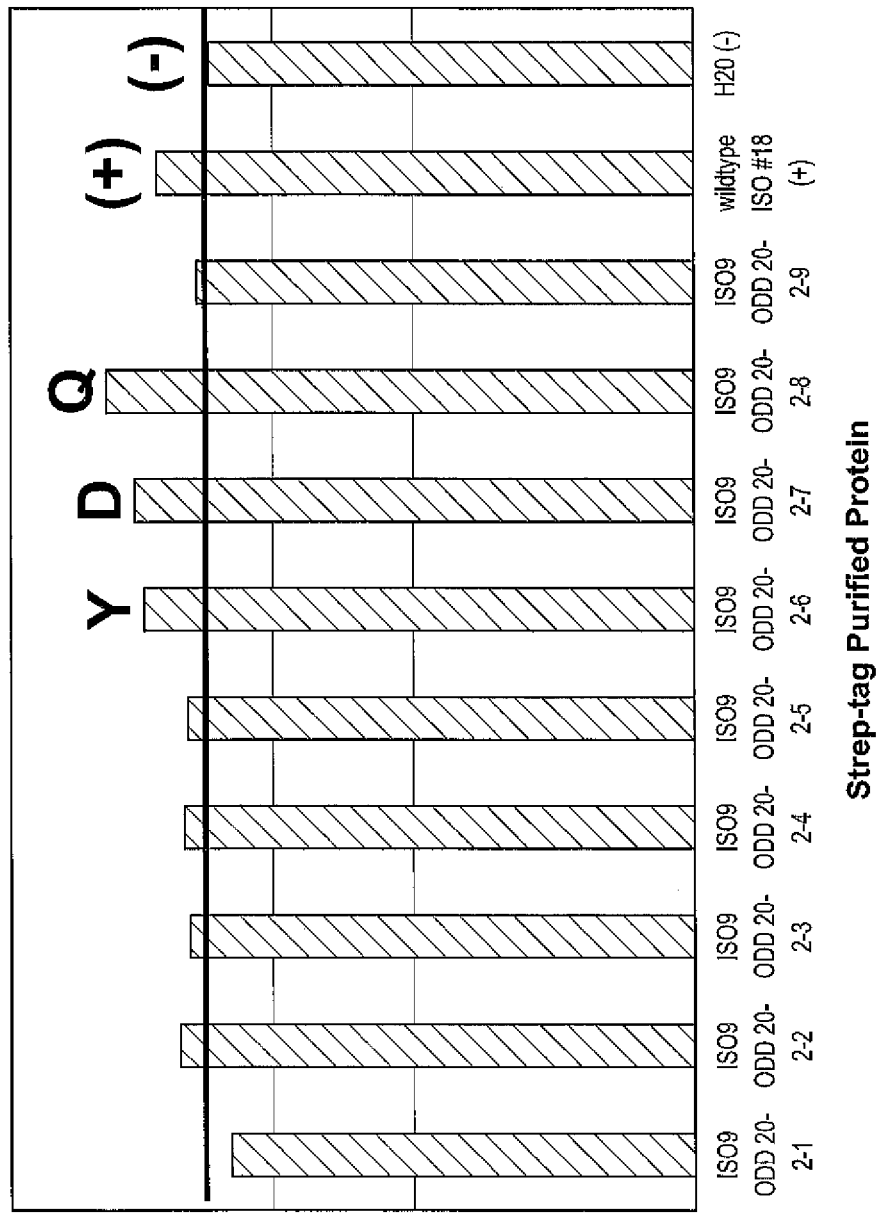
FIG. 9 shows individual beneficial mutations found in the variant prenyl transferases.

The PPi light detection and conversion reagents were prepared as instructed by the manufacturer (Lonza Group Ltd., Basel, Switzerland). After the two hour incubation, 40 µl of the conversion reagent, and 40 µl of the detection reagent were added to the wells of the microplate, and the microplate was sealed with an aluminum foil cover. After sixty minutes, the aluminum cover was removed, and the luminescence emitted from each well was measured with a 96 well plate reader in glow luminescence mode. The total luminescence is reported as Relative Luminescence Units (RLU). Results are shown in FIGS. 7-9. FIG. 7 shows the PPI assay results of nine pools of 63 variants each, along with the wild type control. As most mutants are anticipated to reduce activity, pools with near wild-type activity were selected for deconvolution (e.g. IS09 Pool Odd 20, marked with a star). FIG. 8 shows the deconvolution of pool Odd 20, broken into seven pools of nine. For this study, each pool is a mixture of variants at a single amino acid position. The positions with activity greater than wild type (e.g. pools Odd 20-2, Odd 20-4, and Odd 20-6) were selected for deconvolution to single residues. FIG. 9 shows the individual mutants in pool Odd 20-2, which corresponds to residue Thr269. The individual mutants with activity greater than wild-type are Odd 20-2-6, Odd 20-2-7, and Odd 20-2-8, corresponding to the point mutations Thr269Tyr, Thr269Asp, and Thr269Gln.

Example 6

Mutagenesis of Prenyl Transferase Using Look-Through Mutagenesis

In this example, the improved look-through mutagenesis of another prenyl transferase is described.

The native sequence of the *Myzus persicae* bifunctional GPP/FPP synthase (Genbank Accession No. AAY33491 (SEQ ID NO: 5) can be used as the parent sequence for Look-through Mutagenesis. This gene is 1.2 kb long, and can be synthesized using 57 oligonucleotides. Each oligonucleotide is comprised of 63 nucleotides, 21 constant native sequence nucleotides, followed by 21 nucleotides that are varied to encode the mutant sequences, followed by 21 constant native sequence nucleotides. The two constant native regions of adjacent oligonucleotides anneal together, and thermostable polymerases are used to complete the synthesis of the gene as described in Example 4.

In this example, Look-through mutagenesis of the entire gene is conducted. In order to synthesize the FPPS gene, 3591 oligonucleotides are synthesized, encoding the entire wild type or parent gene, and all 57 oligonucleotide windows are treated as mutagenesis windows. For the mutagenesis windows, each oligonucleotide encodes one amino acid as a mutant. At each position, the wild type sequence is mutated to glycine, serine, histidine, leucine, proline, tyrosine, aspartic acid, glutamine, and lysine in the individual mutants. Each pool of 63 variants, therefore, is composed of these nine variants at each position over a seven amino acid window.

These oligonucleotides are used in a series of PCR reactions to assemble the libraries of variant bifunctional synthases. Sequential PCR reactions are run to assemble the mutant libraries, according to the method of Reisinger, et al. (2007) Nature Protocols 1:2596-2603. An oligonucleotide encoding the bacteriophage T7 promoter is included in the PCR primer encoding the 5' end of the synthesized gene (according to instructions from New England Biolabs for use with the PURExpress in vitro protein synthesis kit (New England Biolabs, Ipswich, Mass.)). Also included in the 3' primer was a nucleic acid sequence encoding a Strep-Tag (WSHPQFEK) useful for protein purification (using the Streptactin system, IBA GmbH, Goettingen, Germany).

After gene assembly is completed, the NEB PURExpress in vitro protein synthesis kit is used according to the manufacturer's instructions to produce the variant synthase proteins. After protein synthesis, Strep-Tag magnetic beads (IBA GmbH) are used to isolate the synthesized proteins, after washing the beads with assay buffer (25 mm HEPES pH 7.4, 10 mM $MgCl_2$).

After synthesis, the activity level of the synthesized protein is measured as described in Example 5 by luminescence. Pools of 63 variants with similar activity are identified. Because most mutations are anticipated to be detrimental, it is unlikely for any pool of mutants to a have higher activity than the wild-type protein; pools with higher activity than average must be deconvoluted to identify individual beneficial mutants.

After pools containing comparable activity are identified, the 63 member pool is resynthesized into seven pools, each containing the nine variants of an individual amino acid residue. The activity of these pools are again measured, and individual pools with activity greater than wild type are identified. The winning pools of nine variants are again resynthesized as discrete mutants and activity measurements are repeated. At this point, individual beneficial mutations are identified.

Example 7

Mutagenesis of Terpene Cyclase Using Look-Through Mutagenesis

In this example, the improved look-through mutagenesis of a terpene cyclase is described.

The native nucleic acid sequence of the *Mentha spicata* limonene synthase (Table 2) (Genbank Accession No. 2ONH_A) can be used as the parent sequence for Look-through Mutagenesis. Optionally, the nucleic acid can be codon-optimized to a host genome in which the syanthase is to be expressed. This gene is 1.8 kb long, and can be synthesized using 86 oligonucleotides. Each oligonucleotide is comprised of 63 nucleotides, 21 constant native sequence nucleotides, followed by 21 nucleotides that are varied to encode the mutant sequences, followed by 21 constant native sequence nucleotides. The two constant native regions of adjacent oligonucleotides anneal together, and thermostable polymerases are used to complete the synthesis of the gene as described in Example 4.

In this example, Look-through mutagenesis of the entire gene is described. In order to synthesize the FPPS gene, 5418 oligonucleotides are synthesized, encoding the entire wild type or parent gene, and all 84 oligonucleotide windows are treated as mutagenesis windows. For the mutagenesis windows, each oligonucleotide encodes one amino acid as a mutant. At each position, the wild type sequence is mutated to glycine, serine, histidine, leucine, proline, tyrosine, aspartic acid, glutamine, and lysine in the individual mutants. Each pool of 63 variants, therefore, is composed of these nine variants at each position over a seven amino acid window.

These oligonucleotides are used in a series of PCR reactions to assemble the libraries of variant synthases. Sequential PCR reactions are run to assemble the mutant libraries, according to the method of Reisinger, et al. (2007) Nature Protocols 1:2596-2603. An oligonucleotide encoding the bacteriophage T7 promoter is included in the PCR primer encoding the 5' end of the synthesized gene (according to instructions from New England Biolabs for use with the PURExpress in vitro protein synthesis kit (New England Biolabs, Ipswich, Mass.)). Also included in the 3' primer was a nucleic acid sequence encoding a Strep-Tag (WSHPQFEK) useful for protein purification (using the Streptactin system, IBA GmbH, Goettingen, Germany).

After gene assembly is completed, the NEB PURExpress in vitro protein synthesis kit is used according to the manufacturer's instructions to produce the variant synthase proteins. After protein synthesis, Strep-Tag magnetic beads (IBA GmbH) are used to isolate the synthesized proteins, after washing the beads with assay buffer (25 mm HEPES pH 7.4, 10 mM $MgCl_2$).

After synthesis, the activity level of the synthesized protein is measured as described in Example 5 by luminescence. Pools of 63 variants with similar activity are identified. Because most mutations are anticipated to be detrimental, it is unlikely for any pool of mutants to have higher activity than the wild-type protein; pools with higher activity than average must be deconvoluted to identify individual beneficial mutants.

After pools containing comparable activity are identified, the 63 member pool is resynthesized into seven pools, each containing the nine variants of an individual amino acid residue. The activity of these pools are again measured, and individual pools with activity greater than wild type are identified. The winning pools of nine variants are again resynthesized as discrete mutants and activity measurements are repeated. At this point, individual beneficial mutations are identified.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An isolated polynucleotide comprising:
   a) nucleic acid sequence SEQ ID NO: 21, wherein nucleotides 802, 803, and 804 of SEQ ID NO: 21 encode Tyrosine, Aspartic Acid, or Glutamine.

2. The isolated polynucleotide of claim 1, wherein nucleotides 802, 803, and 804 of SEQ ID NO: 21 encode Tyrosine.

3. The isolated polynucleotide of claim 1, wherein nucleotides 802, 803, and 804 of SEQ ID NO: 21 encode Aspartic Acid.

4. The isolated polynucleotide of claim 1, wherein nucleotides 802, 803, and 804 of SEQ ID NO: 21 encode Glutamine.

* * * * *

SEQUENCE LISTING

```
<160> NUMBER OF SEQ ID NOS: 29

<210> SEQ ID NO 1
<211> LENGTH: 367
<212> TYPE: PRT
<213> ORGANISM: Gallus gallus

<400> SEQUENCE: 1

Met His Lys Phe Thr Gly Val Asn Ala Lys Phe Gln Gln Pro Ala Leu
1               5                   10                  15

Arg Asn Leu Ser Pro Val Val Val Glu Arg Glu Arg Glu Glu Phe Val
```

```
            20                  25                  30
Gly Phe Phe Pro Gln Ile Val Arg Asp Leu Thr Glu Asp Gly Ile Gly
            35                  40                  45
His Pro Glu Val Gly Asp Ala Val Ala Arg Leu Lys Glu Val Leu Gln
50                  55                  60
Tyr Asn Ala Pro Gly Lys Cys Asn Arg Gly Leu Thr Val Val Ala
65                  70                  75                  80
Ala Tyr Arg Glu Leu Ser Gly Pro Gly Gln Lys Asp Ala Glu Ser Leu
                85                  90                  95
Arg Cys Ala Leu Ala Val Gly Trp Cys Ile Glu Leu Phe Gln Ala Phe
            100                 105                 110
Phe Leu Val Ala Asp Asp Ile Met Asp Gln Ser Leu Thr Arg Arg Gly
            115                 120                 125
Gln Leu Cys Trp Tyr Lys Lys Glu Gly Val Gly Leu Asp Ala Ile Asn
            130                 135                 140
Asp Ser Phe Leu Leu Glu Ser Ser Val Tyr Arg Val Leu Lys Lys Tyr
145                 150                 155                 160
Cys Arg Gln Arg Pro Tyr Tyr Val His Leu Leu Glu Leu Phe Leu Gln
                165                 170                 175
Thr Ala Tyr Gln Thr Glu Leu Gly Gln Met Leu Asp Leu Ile Thr Ala
            180                 185                 190
Pro Val Ser Lys Val Asp Leu Ser His Phe Ser Glu Glu Arg Tyr Lys
            195                 200                 205
Ala Ile Val Lys Tyr Lys Thr Ala Phe Tyr Ser Phe Tyr Leu Pro Val
            210                 215                 220
Ala Ala Ala Met Tyr Met Val Gly Ile Asp Ser Lys Glu Glu His Glu
225                 230                 235                 240
Asn Ala Lys Ala Ile Leu Leu Glu Met Gly Glu Tyr Phe Gln Ile Gln
                245                 250                 255
Asp Asp Tyr Leu Asp Cys Phe Gly Asp Pro Ala Leu Thr Gly Lys Val
            260                 265                 270
Gly Thr Asp Ile Gln Asp Asn Lys Cys Ser Trp Leu Val Val Gln Cys
            275                 280                 285
Leu Gln Arg Val Thr Pro Glu Gln Arg Gln Leu Leu Glu Asp Asn Tyr
            290                 295                 300
Gly Arg Lys Glu Pro Glu Lys Val Ala Lys Val Lys Glu Leu Tyr Glu
305                 310                 315                 320
Ala Val Gly Met Arg Ala Ala Phe Gln Gln Tyr Glu Glu Ser Ser Tyr
                325                 330                 335
Arg Arg Leu Gln Glu Leu Ile Glu Lys His Ser Asn Arg Leu Pro Lys
            340                 345                 350
Glu Ile Phe Leu Gly Leu Ala Gln Lys Ile Tyr Lys Arg Gln Lys
            355                 360                 365

<210> SEQ ID NO 2
<211> LENGTH: 376
<212> TYPE: PRT
<213> ORGANISM: Bos taurus

<400> SEQUENCE: 2

Glu Tyr Pro Ser Asn Asn Leu Asp Leu Gln Pro Ala Ser Arg Asn Arg
1               5                   10                  15
Ala Phe Tyr Ser Ser Leu Arg Val Asn Gly Asp Gln Lys Leu Asp Ala
            20                  25                  30
```

Tyr Ala Gln Glu Arg Gln Asp Phe Ile Gln His Phe Ser Gln Ile Val
            35                  40                  45

Lys Val Leu Thr Glu Glu Asp Ile Gly His Pro Glu Ile Gly Asp Ala
 50                  55                  60

Ile Thr Arg Leu Lys Glu Val Leu Glu Tyr Asn Ala Ile Gly Gly Lys
 65                  70                  75                  80

Tyr Asn Arg Gly Leu Thr Val Val Ile Thr Phe Arg Glu Leu Val Glu
                85                  90                  95

Pro Gly Lys Gln Asp Pro Asp Ser Leu Gln Arg Ala Leu Thr Val Gly
            100                 105                 110

Trp Cys Val Glu Leu Leu Gln Ala Phe Phe Leu Val Ser Asp Asp Ile
            115                 120                 125

Met Asp Ser Ser Leu Thr Arg Arg Gly Gln Thr Cys Trp Tyr Gln Lys
 130                 135                 140

Pro Gly Ile Gly Leu Asp Ala Ile Asn Asp Ala Phe Leu Leu Glu Ser
145                 150                 155                 160

Ser Ile Tyr Arg Leu Leu Lys Leu Tyr Cys Arg Glu Gln Pro Tyr Tyr
                165                 170                 175

Leu Asp Leu Ile Glu Leu Phe Leu Gln Ser Ser Tyr Gln Thr Glu Ile
            180                 185                 190

Gly Gln Thr Leu Asp Leu Ile Thr Ala Pro Gln Gly Asn Val Asp Leu
            195                 200                 205

Gly Arg Phe Thr Glu Lys Arg Tyr Lys Ser Ile Val Lys Tyr Lys Thr
210                 215                 220

Ala Phe Tyr Ser Phe Tyr Leu Pro Val Ala Ala Met Tyr Met Ala
225                 230                 235                 240

Gly Ile Asp Gly Glu Lys Glu His Ala His Ala Lys Lys Ile Leu Leu
                245                 250                 255

Glu Met Gly Glu Phe Phe Gln Ile Gln Asp Asp Tyr Leu Asp Leu Phe
            260                 265                 270

Gly Asp Pro Ser Met Thr Gly Lys Ile Gly Thr Asp Ile Gln Asp Asn
            275                 280                 285

Lys Cys Ser Trp Leu Val Val Gln Cys Leu Gln Arg Ala Ser Pro Glu
290                 295                 300

Gln Arg Gln Ile Leu Gln Glu Asn Tyr Gly Gln Lys Glu Ala Glu Lys
305                 310                 315                 320

Val Ala Arg Val Lys Ala Leu Tyr Glu Glu Met Asn Leu Ser Ala Val
                325                 330                 335

Tyr Met Gln Tyr Glu Glu Asp Ser Tyr Asn His Ile Met Gly Leu Ile
            340                 345                 350

Glu Gln Tyr Ala Ala Pro Leu Pro Pro Ala Ile Phe Leu Gly Leu Ala
            355                 360                 365

Gln Lys Ile Tyr Lys Arg Lys Lys
370                 375

<210> SEQ ID NO 3
<211> LENGTH: 438
<212> TYPE: PRT
<213> ORGANISM: Anthonomus grandis

<400> SEQUENCE: 3

Met Phe Ser Val Lys Leu Cys Arg Asn Arg Ser Cys Arg Glu Leu Ile
1               5                   10                  15

Lys Asn Ile Arg Arg Gly Ile Thr Lys Thr Ser Thr Asp Ser Asn Ser
            20                  25                  30

```
Asp Ala Ile Ser Arg Ala Gln Asp His Asn Gln Met Asn Asn Phe Asn
         35                  40                  45

Leu Glu Gly Pro Ser Ser Gln Tyr His Thr Asn Val Asn Asn Lys Arg
 50                  55                  60

Trp His Lys Gln Met Gln Phe Asn Asn Leu Arg Ala Leu Ser Thr Ile
 65                  70                  75                  80

Gln Gln Thr Ile Pro Lys Pro Ser His Ser Ser Thr Leu Val Ser Lys
                 85                  90                  95

Glu Gln Ser Arg Asp Phe Met Ala Leu Phe Pro Asp Leu Val Arg Glu
                100                 105                 110

Leu Thr Glu Leu Gly Arg Asn Pro Glu Leu Pro Asp Val Met Arg Arg
         115                 120                 125

Val Ala Arg Val Leu Gln Tyr Asn Val Pro Asn Gly Lys Lys Asn Arg
130                 135                 140

Gly Leu Ile Leu Ile Ser Ala Tyr Lys Met Leu Glu Asp Pro Lys Asn
145                 150                 155                 160

Leu Thr Pro Glu Asn Ile Lys Leu Ala Ser Val Leu Gly Trp Cys Leu
                165                 170                 175

Glu Met Ile His Ser Cys Phe Leu Val Leu Asp Asp Ile Met Asp Asn
                180                 185                 190

Ser Glu Thr Arg Arg Gly Ser Leu Cys Trp Tyr Arg Gln Asn Gly Ile
         195                 200                 205

Gly Leu Ser Ala Ile Asn Asp Gly Leu Ile Leu Glu Asn Ala Val Tyr
210                 215                 220

Thr Leu Leu Lys Met His Leu Arg Asp His Pro Ala Tyr Val Pro Ile
225                 230                 235                 240

Ile Glu Leu Phe His Glu Thr Val Ser Lys Thr Thr Leu Gly Gln Cys
                245                 250                 255

Leu Asp Ser Met Cys Leu Asp Ser Asp Gly Lys Pro Lys Leu Glu Met
                260                 265                 270

Phe Ser Met Ser Arg Tyr Thr Ser Ile Val Lys Tyr Lys Thr Ala Tyr
         275                 280                 285

Tyr Ser Phe His Met Pro Val Ala Val Ala Met Tyr Leu Ala Gly Met
290                 295                 300

Asn Asp Pro Glu Gln His Arg Gln Ala Lys Thr Ile Leu Leu Glu Met
305                 310                 315                 320

Gly Glu Phe Phe Gln Ile Gln Asp Asp Phe Leu Asp Cys Phe Gly Asp
                325                 330                 335

Pro Ala Val Thr Gly Lys Lys Gly Thr Asp Ile Gln Glu Gly Lys Cys
                340                 345                 350

Ser Trp Leu Ala Val Val Ala Leu Gln Arg Ala Ser Ala Ala Gln Arg
         355                 360                 365

Lys Ile Met Glu Glu His Tyr Gly Val Asp Asp Pro Asn Ser Val Ala
370                 375                 380

Ile Ile Lys Lys Leu Tyr Glu Asp Leu Ser Leu Pro Asn Thr Tyr Ala
385                 390                 395                 400

Ile Tyr Glu Glu Glu Ser Tyr Asn Ile Ile Lys Thr His Ile Gln Gln
                405                 410                 415

Ile Ser Lys Gly Leu Arg His Asp Leu Phe Phe Ser Ile Met Glu Lys
         420                 425                 430

Leu Tyr Lys Arg Glu Cys
         435
```

<210> SEQ ID NO 4
<211> LENGTH: 394
<212> TYPE: PRT
<213> ORGANISM: Myzus persicae

<400> SEQUENCE: 4

```
Met Asn Lys Met Leu Thr Phe Thr Arg Ala Leu Ser Arg Arg Ser Ala
1               5                   10                  15

Phe Leu Leu Cys Asp Ser Ala Val Val Arg Asn Asn Asn Phe Arg Ala
            20                  25                  30

Met Ser Thr Val Arg Ala Pro Pro Val Pro Pro Val Ile Thr Gly Thr
        35                  40                  45

Ala Val Ser Lys Asp Glu Thr Arg Asp Phe Met Ala Val Phe Pro Asp
    50                  55                  60

Val Val Arg Asp Leu Thr Asp Thr Gly Arg Asn Leu Asp Val Pro Asp
65                  70                  75                  80

Val Thr Lys Trp Leu Ala Lys Leu Leu Gln Tyr Asn Val Pro Gly Gly
                85                  90                  95

Lys Lys Asn Arg Gly Leu Ala Leu Val Leu Ser Tyr Lys Met Leu Ser
            100                 105                 110

Ser Pro Ser Asp Gln Thr Asp Glu Asn Leu Lys Leu Ser Tyr Ile Leu
        115                 120                 125

Gly Trp Cys Val Glu Ile Leu Gln Ala Tyr Gln Leu Val Leu Asp Asp
    130                 135                 140

Ile Met Asp Asn Ala Ile Thr Arg Arg Gly Arg Pro Cys Trp Tyr Arg
145                 150                 155                 160

His Asn Asp Ile Gly Leu Met Ala Val Asn Asp Gly Val Leu Leu Glu
                165                 170                 175

Gln Ala Ile Tyr Gln Leu Ile Lys Lys Tyr Phe Lys Asp Lys Pro Tyr
            180                 185                 190

Tyr Thr His Ile Leu Glu Leu Phe Phe Asp Val Thr Met Lys Thr Ala
        195                 200                 205

Met Gly Gln Cys Leu Asp Met Leu Thr Ala Asn Ser Phe Lys Ser Lys
    210                 215                 220

Lys Leu Glu Lys Tyr Thr Met Glu Asn Tyr Thr Ala Ile Val Lys Tyr
225                 230                 235                 240

Lys Thr Ala Tyr Tyr Ser Phe Phe Leu Pro Val Cys Leu Ala Met Arg
                245                 250                 255

Met Thr Asn Ile Asn Asp Pro Glu Ile Phe Arg Gln Ala Lys Thr Ile
            260                 265                 270

Leu Leu Glu Met Gly His Phe Phe Gln Val Gln Asp Asp Phe Leu Asp
        275                 280                 285

Cys Tyr Gly Asp Pro Asp Val Met Gly Lys Ile Gly Thr Asp Ile Glu
    290                 295                 300

Asp Gly Lys Cys Ser Trp Leu Ala Val Val Ala Leu Gln Lys Val Asn
305                 310                 315                 320

Ser Glu Gln Lys Lys Ile Met Glu Asp Asn Tyr Gly Ile Asp Asp Pro
                325                 330                 335

Ala Asn Val Ala Ile Ile Lys Asp Leu Tyr Ala Gln Leu Lys Leu Ala
            340                 345                 350

Asp Thr Phe His Leu Tyr Glu Glu Ser Tyr Lys Leu Ile Cys Thr
        355                 360                 365

His Ile Gln Gln Leu Ser Arg Gly Leu Ser Gln Asp Met Phe Phe Lys
    370                 375                 380
```

Phe Leu Glu Lys Ile Tyr Lys Arg Thr Leu
385                 390

<210> SEQ ID NO 5
<211> LENGTH: 362
<212> TYPE: PRT
<213> ORGANISM: Myzus persicae

<400> SEQUENCE: 5

Met Ser Thr Val Arg Ala Pro Pro Val Pro Val Ile Thr Gly Thr
1               5                   10                  15

Ala Val Ser Lys Asp Glu Thr Arg Asp Phe Met Ala Val Phe Pro Asp
                20                  25                  30

Val Val Arg Asp Leu Thr Asp Thr Gly Arg Asn Leu Asp Val Pro Asp
            35                  40                  45

Val Thr Lys Trp Leu Ala Lys Leu Leu Gln Tyr Asn Val Pro Gly Gly
        50                  55                  60

Lys Lys Asn Arg Gly Leu Ala Leu Val Leu Ser Tyr Lys Met Leu Ser
65                  70                  75                  80

Ser Pro Ser Asp Gln Thr Asp Glu Asn Leu Lys Leu Ser Tyr Ile Leu
                85                  90                  95

Gly Trp Cys Val Glu Ile Leu Gln Ala Tyr Gln Leu Val Leu Asp Asp
            100                 105                 110

Ile Met Asp Asn Ala Ile Thr Arg Arg Gly Arg Pro Cys Trp Tyr Arg
        115                 120                 125

His Asn Asp Ile Gly Leu Met Ala Val Asn Asp Gly Val Leu Leu Glu
130                 135                 140

Gln Ala Ile Tyr Gln Leu Ile Lys Lys Tyr Phe Lys Asp Lys Pro Tyr
145                 150                 155                 160

Tyr Thr His Ile Leu Glu Leu Phe Phe Asp Val Thr Met Lys Thr Ala
                165                 170                 175

Met Gly Gln Cys Leu Asp Met Leu Thr Ala Asn Ser Phe Lys Ser Lys
            180                 185                 190

Lys Leu Glu Lys Tyr Thr Met Glu Asn Tyr Thr Ala Ile Val Lys Tyr
        195                 200                 205

Lys Thr Ala Tyr Tyr Ser Phe Phe Leu Pro Val Cys Leu Ala Met Arg
210                 215                 220

Met Thr Asn Ile Asn Asp Pro Glu Ile Phe Arg Gln Ala Lys Thr Ile
225                 230                 235                 240

Leu Leu Glu Met Gly His Phe Phe Gln Val Gln Asp Asp Phe Leu Asp
                245                 250                 255

Cys Tyr Gly Asp Pro Asp Val Met Gly Lys Ile Gly Thr Asp Ile Glu
            260                 265                 270

Asp Gly Lys Cys Ser Trp Leu Ala Val Val Ala Leu Gln Lys Val Asn
        275                 280                 285

Ser Glu Gln Lys Lys Ile Met Glu Asp Asn Tyr Gly Ile Asp Asp Pro
290                 295                 300

Ala Asn Val Ala Ile Ile Lys Asp Leu Tyr Ala Gln Leu Lys Leu Ala
305                 310                 315                 320

Asp Thr Phe His Phe Tyr Glu Glu Ser Tyr Lys Leu Ile Cys Thr
                325                 330                 335

His Ile Gln Gln Leu Ser Arg Gly Leu Ser Gln Asp Met Phe Phe Lys
            340                 345                 350

Phe Leu Glu Lys Ile Tyr Lys Arg Thr Leu

<210> SEQ ID NO 6
<211> LENGTH: 349
<212> TYPE: PRT
<213> ORGANISM: Kluyveromyces lactis

<400> SEQUENCE: 6

```
Met Ser Asp Asn Arg Ala Gln Phe Leu Glu Val Phe Pro Ser Leu Val
1               5                   10                  15

Gln Glu Leu Arg Asp Ile Leu Ala Gly Tyr Gly Met Pro Glu Glu Ala
            20                  25                  30

Ile Glu Trp Tyr Glu Lys Ser Leu Asn Tyr Asn Thr Pro Gly Gly Lys
        35                  40                  45

Leu Asn Arg Gly Leu Ser Val Val Asp Thr Tyr Ala Leu Leu Lys Gly
    50                  55                  60

Tyr Lys Ser Val Ser Glu Leu Ser Ala Glu Glu Tyr Lys Lys Val Ala
65                  70                  75                  80

Ile Leu Gly Trp Cys Ile Glu Leu Leu Gln Ala Tyr Phe Leu Val Ala
                85                  90                  95

Asp Asp Met Met Asp Gln Ser Ile Thr Arg Arg Gly Gln Pro Cys Trp
            100                 105                 110

Tyr Lys Val Glu Asn Val Gly Asp Ile Ala Ile Asn Asp Ala Phe Met
        115                 120                 125

Leu Glu Gly Ala Ile Tyr Cys Leu Leu Lys Lys His Phe Arg Thr Glu
    130                 135                 140

Pro Tyr Tyr Val Asp Leu Leu Glu Leu Phe His Asp Val Thr Phe Gln
145                 150                 155                 160

Thr Glu Leu Gly Gln Leu Leu Asp Leu Ile Thr Ala Pro Glu Asp Lys
                165                 170                 175

Val Asp Leu Ser Lys Phe Ser Leu Glu Lys His Ser Phe Ile Val Ile
            180                 185                 190

Phe Lys Thr Ala Tyr Tyr Ser Phe Tyr Leu Ala Val Ala Leu Ala Met
        195                 200                 205

Phe Ala Ala Gly Ile Thr Asp Ser Lys Asp Leu Lys Gln Ala Ser Asp
    210                 215                 220

Val Leu Ile Pro Leu Gly Glu Tyr Phe Gln Ile Gln Asp Asp Phe Leu
225                 230                 235                 240

Asp Cys Phe Gly Lys Pro Glu Asp Ile Gly Lys Ile Gly Thr Asp Ile
                245                 250                 255

Gln Asp Asn Lys Cys Ser Trp Val Ile Asn Val Ala Leu Lys Asn Ala
            260                 265                 270

Thr Lys Glu Gln Arg Asp Ile Leu Asp Glu Asn Tyr Gly Arg Lys Asp
        275                 280                 285

Ser Glu Lys Glu Gln Lys Cys Arg Ala Val Phe Asn Glu Leu Asn Ile
    290                 295                 300

Gln Asp Ile Tyr His Lys Tyr Glu Glu Thr Ala Ser Asn Leu Arg
305                 310                 315                 320

Glu Lys Ile Ala Asn Ile Asp Glu Ser Arg Gly Phe Lys Ala Glu Val
                325                 330                 335

Leu Thr Leu Phe Leu Asn Lys Ile Tyr His Arg Lys Lys
            340                 345
```

<210> SEQ ID NO 7
<211> LENGTH: 394

<212> TYPE: PRT
<213> ORGANISM: Artemisia spiciformis

<400> SEQUENCE: 7

Met Ala Ser Phe Ile Ser Leu Ser Ser Lys Ser Ala Ser Trp Asn Ala
1               5                   10                  15

Ser Ser Cys Pro His Pro Ser Val Gln Pro Phe Val Thr Arg Lys Asn
            20                  25                  30

Val Val Arg Tyr His Lys Pro Thr Ser Ser Glu Pro Ser Tyr Ser Pro
        35                  40                  45

Leu Thr Thr Thr Leu Ser Ser Asn Leu Asn Ser Gln Phe Met Gln Val
    50                  55                  60

Tyr Glu Thr Leu Lys Ser Glu Leu Ile His Asp Pro Leu Phe Glu Phe
65                  70                  75                  80

Asp Asp Asp Ser Arg Gln Trp Val Glu Arg Met Ile Asp Tyr Thr Val
                85                  90                  95

Pro Gly Gly Lys Met Val Arg Gly Tyr Ser Val Val Asp Ser Tyr Gln
            100                 105                 110

Leu Leu Lys Gly Glu Glu Leu Thr Glu Glu Glu Ala Phe Leu Ala Cys
        115                 120                 125

Ala Leu Gly Trp Cys Thr Glu Trp Phe Gln Ala Phe Ile Leu Leu His
    130                 135                 140

Asp Asp Met Met Asp Gly Ser His Thr Arg Arg Gly Gln Pro Cys Trp
145                 150                 155                 160

Phe Arg Leu Pro Glu Val Gly Ala Val Ala Ile Asn Asp Gly Val Leu
                165                 170                 175

Leu Arg Asn His Val His Arg Ile Leu Lys Lys His Phe Gln Gly Lys
            180                 185                 190

Ala Tyr Tyr Val His Leu Val Asp Leu Phe Asn Glu Thr Glu Phe Gln
        195                 200                 205

Thr Ile Ser Gly Gln Met Ile Asp Thr Ile Ser Arg Leu Ala Gly Gln
    210                 215                 220

Lys Glu Leu Ser Lys Tyr Ser Met Ser Leu Asn Arg Arg Ile Val Gln
225                 230                 235                 240

Tyr Lys Gly Ala Tyr Tyr Ser Cys Tyr Leu Pro Ile Ala Cys Ala Leu
                245                 250                 255

Leu Met Phe Gly Glu Asn Leu Asp Asp Tyr Val Gln Val Lys Asp Ile
            260                 265                 270

Leu Val Glu Leu Gly Met Tyr Tyr Gln Ile Gln Asn Asp Tyr Leu Asp
        275                 280                 285

Thr Phe Gly Asp Pro Asn Val Phe Gly Lys Thr Gly Thr Asp Ile Glu
    290                 295                 300

Glu Cys Lys Cys Ser Trp Leu Ile Ala Lys Ala Leu Glu Leu Ala Asn
305                 310                 315                 320

Glu Glu Gln Lys Lys Ile Leu Ser Glu Asn Tyr Gly Ile Lys Asp Pro
                325                 330                 335

Ala Lys Val Ala Lys Val Lys Glu Ile Tyr His Ala Leu Asn Leu Lys
            340                 345                 350

Gly Ala Tyr Glu Asp Tyr Glu Thr Asn Leu Tyr Glu Asn Ser Met Lys
        355                 360                 365

Ala Ile Lys Ala His Pro Ser Ile Ala Val Gln Ala Val Leu Lys Ser
    370                 375                 380

Cys Leu Glu Lys Met Tyr Lys Gly His Lys
385                 390

<210> SEQ ID NO 8
<211> LENGTH: 346
<212> TYPE: PRT
<213> ORGANISM: Artificial Sequence
<220> FEATURE:
<223> OTHER INFORMATION: Chimeric protein

<400> SEQUENCE: 8

Thr Thr Thr Leu Ser Ser Asn Leu Asn Ser Gln Phe Met Gln Val Tyr
1               5                   10                  15

Glu Thr Leu Lys Ser Glu Leu Ile His Asp Pro Leu Phe Glu Phe Asp
            20                  25                  30

Asp Asp Ser Arg Gln Trp Val Glu Arg Met Ile Asp Tyr Thr Val Pro
        35                  40                  45

Gly Gly Lys Met Val Arg Gly Tyr Ser Val Val Asp Ser Tyr Gln Leu
    50                  55                  60

Leu Lys Gly Glu Glu Leu Thr Glu Glu Glu Ala Phe Leu Ala Cys Ala
65                  70                  75                  80

Leu Gly Trp Cys Thr Glu Trp Phe Gln Ala Phe Ile Leu Leu His Asp
                85                  90                  95

Asp Met Met Asp Gly Ser His Thr Arg Arg Gly Gln Pro Cys Trp Phe
            100                 105                 110

Arg Leu Pro Glu Val Gly Ala Val Ala Ile Asn Asp Gly Val Leu Leu
        115                 120                 125

Arg Asn His Val His Arg Ile Leu Lys Lys His Phe Gln Gly Lys Ala
    130                 135                 140

Tyr Tyr Val His Leu Val Asp Leu Phe Asn Glu Thr Glu Phe Gln Thr
145                 150                 155                 160

Ile Ser Gly Gln Met Ile Asp Leu Ile Thr Thr Leu Val Gly Glu Lys
                165                 170                 175

Asp Leu Ser Lys Tyr Ser Leu Ser Ile His Arg Arg Ile Val Gln Tyr
            180                 185                 190

Lys Thr Ala Tyr Tyr Ser Phe Tyr Leu Pro Val Ala Cys Ala Leu Leu
        195                 200                 205

Met Phe Gly Glu Asp Leu Asp Lys His Val Glu Val Lys Asn Val Leu
    210                 215                 220

Val Glu Met Gly Thr Tyr Phe Gln Val Gln Asp Asp Tyr Leu Asp Cys
225                 230                 235                 240

Phe Gly Ala Pro Glu Val Ile Gly Lys Ile Gly Thr Asp Ile Glu Asp
                245                 250                 255

Phe Lys Cys Ser Trp Leu Val Val Lys Ala Leu Glu Leu Ala Asn Glu
            260                 265                 270

Glu Gln Lys Lys Thr Leu His Glu Asn Tyr Gly Lys Lys Asp Pro Ala
        275                 280                 285

Ser Val Ala Lys Val Lys Glu Val Tyr His Thr Leu Asn Leu Gln Ala
    290                 295                 300

Val Phe Glu Asp Tyr Glu Ala Thr Ser Tyr Lys Lys Leu Ile Thr Ser
305                 310                 315                 320

Ile Glu Asn His Pro Ser Lys Ala Val Gln Ala Val Leu Lys Ser Phe
                325                 330                 335

Leu Gly Lys Ile Tyr Lys Arg Gln Lys Gly
            340                 345

<210> SEQ ID NO 9

```
<211> LENGTH: 352
<212> TYPE: PRT
<213> ORGANISM: Saccharomyces cerevisiae

<400> SEQUENCE: 9

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Asp Thr Tyr Ala
    50                  55                  60

Ile Leu Ser Lys Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

<210> SEQ ID NO 10
<211> LENGTH: 350
<212> TYPE: PRT
<213> ORGANISM: Zea mays

<400> SEQUENCE: 10
```

```
Met Ala Ala Gly Gly Asn Gly Ala Gly Gly Asp Thr Arg Ala Ala Phe
1               5                   10                  15

Ala Arg Ile Tyr Lys Thr Leu Lys Glu Glu Leu Leu Thr Asp Pro Ala
            20                  25                  30

Phe Glu Phe Thr Glu Glu Ser Arg Gln Trp Ile Asp Arg Met Val Asp
        35                  40                  45

Tyr Asn Val Leu Gly Gly Lys Cys Asn Arg Gly Leu Ser Val Val Asp
    50                  55                  60

Ser Tyr Lys Leu Leu Lys Gly Ala Asp Ala Leu Gly Glu Glu Glu Thr
65                  70                  75                  80

Phe Leu Ala Cys Thr Leu Gly Trp Cys Ile Glu Trp Leu Gln Ala Phe
            85                  90                  95

Phe Leu Val Leu Asp Asp Ile Met Asp Asp Ser His Thr Arg Arg Gly
        100                 105                 110

Gln Pro Cys Trp Phe Arg Val Pro Gln Val Gly Leu Ile Ala Ala Asn
    115                 120                 125

Asp Gly Ile Ile Leu Arg Asn His Ile Ser Arg Ile Leu Arg Arg His
130                 135                 140

Phe Lys Gly Lys Pro Tyr Tyr Ala Asp Leu Leu Asp Leu Phe Asn Glu
145                 150                 155                 160

Val Glu Phe Lys Thr Ala Ser Gly Gln Leu Leu Asp Leu Ile Thr Thr
            165                 170                 175

His Glu Gly Glu Lys Asp Leu Thr Lys Tyr Asn Ile Thr Val His Gly
        180                 185                 190

Arg Ile Val Gln Tyr Lys Thr Ala Tyr Tyr Ser Phe Tyr Leu Pro Val
    195                 200                 205

Ala Cys Ala Leu Leu Leu Ser Gly Glu Asn Leu Asp Asn Tyr Gly Asp
210                 215                 220

Val Glu Asn Ile Leu Val Glu Met Gly Thr Tyr Phe Gln Val Gln Asp
225                 230                 235                 240

Asp Tyr Leu Asp Cys Tyr Gly Asp Pro Glu Phe Ile Gly Lys Ile Gly
            245                 250                 255

Thr Asp Ile Glu Asp Tyr Lys Cys Ser Trp Leu Val Val Gln Ala Leu
        260                 265                 270

Glu Arg Ala Asp Glu Ser Gln Lys Arg Ile Leu Phe Glu Asn Tyr Gly
    275                 280                 285

Lys Lys Asp Pro Ala Cys Val Ala Lys Val Lys Asn Leu Tyr Lys Glu
290                 295                 300

Leu Asp Leu Glu Ala Val Phe Gln Glu Tyr Glu Asn Glu Ser Tyr Lys
305                 310                 315                 320

Lys Leu Ile Ala Asp Ile Glu Ala Gln Pro Ser Ile Ala Val Gln Lys
            325                 330                 335

Val Leu Lys Ser Phe Leu His Lys Ile Tyr Lys Arg Gln Lys
        340                 345                 350

<210> SEQ ID NO 11
<211> LENGTH: 343
<212> TYPE: PRT
<213> ORGANISM: Artemisia annua

<400> SEQUENCE: 11

Met Ser Ser Thr Asp Leu Lys Ser Lys Phe Leu Lys Val Tyr Asp Thr
1               5                   10                  15

Leu Lys Ser Glu Leu Ile Asn Asp Pro Ala Phe Glu Phe Asp Asp Asp
```

```
                20                  25                  30
Ser Arg Gln Trp Ile Glu Lys Met Leu Asp Tyr Asn Val Pro Gly Gly
             35                  40                  45

Lys Leu Asn Arg Gly Leu Ser Val Val Asp Ser Tyr Gln Leu Leu Lys
 50                  55                  60

Gly Gly Glu Leu Ser Asp Glu Ile Phe Leu Ser Ser Ala Leu Gly
 65                  70                  75                  80

Trp Cys Ile Glu Trp Leu Gln Ala Tyr Phe Leu Val Leu Asp Asp Ile
                 85                  90                  95

Met Asp Glu Ser His Thr Arg Arg Gly Gln Pro Cys Trp Phe Arg Leu
            100                 105                 110

Pro Lys Val Gly Met Ile Ala Ala Asn Asp Gly Ile Leu Leu Arg Asn
            115                 120                 125

His Val Pro Arg Ile Leu Lys Lys His Phe Arg Gly Lys Pro Tyr Tyr
            130                 135                 140

Val Asp Leu Val Asp Leu Phe Asn Glu Val Glu Phe Gln Thr Ala Ser
145                 150                 155                 160

Gly Gln Met Ile Asp Leu Ile Thr Thr Leu Val Gly Glu Lys Asp Leu
                165                 170                 175

Ser Lys Tyr Ser Leu Ser Ile His Arg Arg Ile Val Gln Tyr Lys Thr
                180                 185                 190

Ala Tyr Tyr Ser Phe Tyr Leu Pro Val Ala Cys Ala Leu Leu Met Phe
            195                 200                 205

Gly Glu Asp Leu Asp Lys His Val Glu Val Lys Asn Val Leu Val Glu
            210                 215                 220

Met Gly Thr Tyr Phe Gln Val Gln Asp Asp Tyr Leu Asp Cys Phe Gly
225                 230                 235                 240

Ala Pro Glu Val Ile Gly Lys Ile Gly Thr Asp Ile Glu Asp Phe Lys
                245                 250                 255

Cys Ser Trp Leu Val Val Lys Ala Leu Glu Leu Pro Asn Glu Glu Gln
            260                 265                 270

Lys Lys Thr Leu His Glu Asn Tyr Gly Lys Lys Asp Pro Ala Ser Val
            275                 280                 285

Ala Lys Val Lys Glu Val Tyr His Thr Leu Asn Leu Gln Ala Val Phe
            290                 295                 300

Glu Asp Tyr Glu Ala Thr Ser Tyr Lys Lys Leu Ile Thr Ser Ile Glu
305                 310                 315                 320

Asn His Pro Ser Lys Ala Val Gln Ala Val Leu Lys Ser Phe Leu Gly
                325                 330                 335

Lys Ile Tyr Lys Arg Gln Lys
            340

<210> SEQ ID NO 12
<211> LENGTH: 1138
<212> TYPE: DNA
<213> ORGANISM: Bos taurus

<400> SEQUENCE: 12
atgaatggag accagaaatt ggacgcttac gcccaagaaa ggcaggattt catccagcac      60
ttctcccaga ttgtcaaggt gctgactgag gaggacattg gcatccaga gataggagat     120 gccattaccc gactcaagga ggtcctggag tacaatgcca tcggaggcaa gtacaatcgg     180 ggtttgacg tggtaataac cttccgggag cttgtggagc tgggaaaaca agatcctgac     240
agtctccagc gggccctgac tgtgggctgg tgtgtggaac tgctccaagc cttcttcctg     300
```

| | | | |
|---|---|---|---|
| gtgtcagatg | acattatgga | ctcatccctc acccgacggg ggcagacctg ctggtatcag | 360 |
| aagccaggca | taggtttgga | tgccatcaat gatgctttcc ttctggaatc atccatctac | 420 |
| cgcctgttga | agctgtactg | tcgggagcag ccctattacc tggacctgat cgagctcttc | 480 |
| ctgcagagtt | cttatcaaac | tgagatcgga cagaccttgg acctcatcac agctccccag | 540 |
| ggcaacgtgg | atcttggcag | attcacagaa agaggtata agtctattgt caagtacaag | 600 |
| acagctttct | actccttta | ccttcctgta gctgctgcca tgtatatggc gggcattgat | 660 |
| ggggagaagg | agcatgccca | tgccaagaag atcctgctag agatgggaga gttctttcag | 720 |
| attcaggatg | attacctcga | tctctttggg accccagca tgacgggtaa gatcggcaca | 780 |
| gacatccagg | acaacaagtg | cagctggctg gtggtccagt gtctgcagcg ggcctctcca | 840 |
| gagcagcgcc | aaatcctgca | ggagaactat gggcagaagg aggctgagaa ggtggcccga | 900 |
| gtgaaggcgc | tctacgagga | gatgaatctg tcggctgtgt acatgcaata cgaggaagac | 960 |
| agttacaacc | acattatggg | tctcattgag cagtatgctg cgcccctgcc cccagccatc | 1020 |
| ttcctggggt | tagcacaaaa | gatctacaag cggaaaaagt gacctagagt ctgtgaaggt | 1080 |
| ggggaaagga | ggcttcttaa | taaattattg tctaacctgt aaaaaaaaaa aaaaaaaa | 1138 |

<210> SEQ ID NO 13
<211> LENGTH: 1317
<212> TYPE: DNA
<213> ORGANISM: Anthonomus grandis

<400> SEQUENCE: 13

| | | | |
|---|---|---|---|
| atgttttcgg | tgaaattgtg | ccgaaaccgg tcttgccggg agttaatcaa aaacattaga | 60 |
| cggggtatta | cgaaaacttc | gacggatagt aatagcgacg cgatctcgcg ggcacaggac | 120 |
| cataaccaaa | tgaataattt | taatttggag gggccgagta gtcaatacca cacgaatgtt | 180 |
| aacaacaaaa | ggtggcataa | acaaatgcaa tttaataatt taagggccct ttcaacaatc | 240 |
| caacaaacga | tcccaaaacc | gtcacactcc agcaccttgg tgtccaagga caatccagg | 300 |
| gactttatgg | ctctatttcc | agacttggtg agagaactca ccgaactggg aaggaatcca | 360 |
| gagttgcccg | atgtgatgcg | cagagttgct agggtactgc aatataatgt tccaaacggg | 420 |
| aagaaaaata | gaggcttaat | actaattagt gcgtacaaga tgttggaaga tcccaagaat | 480 |
| ttaacaccgg | agaatattaa | gcttgctagc gttttgggat ggtgtttgga atgattcat | 540 |
| tcctgttttcc | ttgttctgga | cgatataatg gacaattcgg agacccgtag ggggtcattg | 600 |
| tgctggtacc | gccaaaacgg | cattgggtta tcggcaataa acgacggact catactggaa | 660 |
| aacgctgttt | acaccctact | taaaatgcac cttagggacc atccagcgta cgtcccaata | 720 |
| atagaactct | tccatgaaac | tgtttccaag accaccttgg gtcagtgctt agactctatg | 780 |
| tgtctagatt | ccgatggaaa | acccaagtta gaaatgtttt ccatgagcag atacacctcg | 840 |
| atcgtaaaat | acaagactgc | ttactatagt ttccatatgc ctgtggctgt ggcgatgtac | 900 |
| ttggctggaa | tgaacgatcc | agagcagcac aggcaagcga agaccatttt gctggaaatg | 960 |
| ggcgaatttt | tccagattca | ggacgacttc ctggattgtt tcggtgatcc agctgtaact | 1020 |
| ggcaaaaaag | gcaccgatat | ccaagagggc aaatgctcct ggttggccgt ggtagctctc | 1080 |
| caaagagctt | cggccgccca | aggaagatc atggaggaac actatggagt ggatgatccc | 1140 |
| aattctgtgg | cgatcattaa | gaaactttat gaagatttga gcttacccaa cacatatgcc | 1200 |
| atttatgagg | aggaatctta | caatatcatt aagactcaca ttcagcaaat ttctaaaggg | 1260 |

```
ctgcgtcacg acctgttctt tagtataatg gagaagttgt acaaacggga gtgttaa    1317

<210> SEQ ID NO 14
<211> LENGTH: 1185
<212> TYPE: DNA
<213> ORGANISM: Myzus persicae

<400> SEQUENCE: 14
atgaacaaaa tgctgacttt tacgagagcc ctaagtcgcc ggagcgcgtt tttgctctgt     60
gactcggctg tcgttcggaa taataacttt cgggctatga gtacagttcg cgcaccgcca    120
gtccctccgg tcataactgg tacagccgtc agcaaggacg agaccaggga tttcatggca    180
gtgttcccag atgtagtcag ggatctgacg gacaccggcc gtaacttaga cgtgcccgat    240
gttaccaagt ggctcgcaaa gctgttgcaa tacaatgtgc ccggtggtaa gaaaaaccga    300
ggattggctt tggtactgtc atacaaaatg ttatcctcgc cttctgatca gactgatgaa    360
aaccttaaat tgtcttacat actgggatgg tgtgttgaaa ttctgcaagc ctatcaatta    420
gtgttagatg acataatgga taacgcaata actagacgag gacgtccatg ttggtatcgg    480
cacaatgata ttggtctaat ggcagtgaac gatggtgttc tcctcgaaca ggccatttac    540
cagttgatta aaaagtactt caaggataag ccttactaca cacatatttt ggagctgttc    600
tttgacgtta caatgaaaac tgcgatgggt cagtgtcttg atatgttaac cgccaatagc    660
ttcaagtcaa aaaaacttga aaatatacc atggaaaatt atacagctat gtgaaatat    720 aagactgctt attattcttt ttttcttcca gtatgtcttg caatgcgcat gacaaacatc    780
aatgacccag aaatctttcg acaagcaaag actatactgc ttgaaatggg acacttcttt    840
caagttcaag atgactttt agactgttat ggagatccag acgtcatggg aaaaattggc    900
acagacatag aagatggtaa atgttcatgg ttagctgtag tggctttgca aaaagtcaat    960
tctgaacaaa agaaaattat ggaggacaac tatggtattg atgatccagc caatgttgca   1020
atcatcaaag atttgtatgc acagttgaaa ttagcagaca catttcatct ctacgaagaa   1080
gaaagttata aattaatatg cactcatatt caacagttgt cacgaggttt gtcacaagac   1140 atgttttttca aattttggga aaagatttac aagagaacac tctaa                  1185

<210> SEQ ID NO 15
<211> LENGTH: 1185
<212> TYPE: DNA
<213> ORGANISM: Myzus persicae

<400> SEQUENCE: 15
atgaacaaaa tgctgacttt tacgagagcc ctaagtcgcc ggagcgcgtt tttgctctgt     60
gactcggctg tcgttcggaa taataacttt cgggctatga gtacagttcg cgcaccgcca    120
gtccctccgg tcataactgg tacagccgtc agcaaggacg agaccaggga tttcatggca    180
gtgttcccag atgtagtcag ggatctgacg gacaccggcc gtaacttaga cgtgcccgat    240
gttaccaagt ggctcgcaaa gctgttgcaa tacaatgtgc ccggtggtaa gaaaaaccga    300
ggattggctt tggtactgtc atacaaaatg ttatcctcgc cttctgatca gactgatgaa    360
aaccttaaat tgtcttacat actgggatgg tgtgttgaaa ttctgcaagc ctatcaatta    420
gtgttagatg acataatgga taacgcaata actagacgag gacgtccatg ttggtatcgg    480
cacaatgata ttggtctaat ggcagtgaac gatggtgttc tcctcgaaca ggccatttac    540
cagttgatta aaaagtactt caaggataag ccttactaca cacatatttt ggagctgttc    600
tttgacgtta caatgaaaac tgcgatgggt cagtgtcttg atatgttaac cgccaatagc    660
```

```
ttcaagtcaa aaaaacttga aaaatatacc atggaaaatt atacagctat tgtgaaatat      720
aagactgctt attattcttt ttttcttcca gtatgtcttg caatgcgcat gacaaacatc      780
aatgacccag aaatctttcg acaagcaaag actatactgc ttgaaatggg acacttcttt      840
caagttcaag atgactttt agactgttat ggagatccag acgtcatggg aaaaattggc       900
acagacatag aagatggtaa atgttcatgg ttagctgtag tggctttgca aaaagtcaat      960
tctgaacaaa agaaaattat ggaggacaac tatggtattg atgatccagc caatgttgca     1020
atcatcaaag atttgtatgc acagttgaaa ttagcagaca catttcattt ttacgaagaa     1080
gaaagttata aattaatatg cactcatatt caacagttgt cacgaggttt gtcacaagac     1140 atgttttca aattttgga aaagatttac aagagaacac tttaa                       1185
```

<210> SEQ ID NO 16
<211> LENGTH: 1050
<212> TYPE: DNA
<213> ORGANISM: Kluyveromyces lactis

<400> SEQUENCE: 16

```
atgagtgata acagagccca gttttttggaa gtgttcccat cattagtaca agagcttaga      60
gacatcttgg ccgggtacgg tatgcccgaa gaagccatcg aatggtacga aaaatcattg     120
aactacaaca ccccaggtgg taagttgaac cgtggtcttt ctgtcgttga cacatacgcg     180
cttttgaaag gttacaagtc agtgagcgaa ctatctgcag aagagtacaa gaaggttgcc     240
atccttggtt ggtgtattga actgttgcaa gcgtacttct tggttgctga tgacatgatg     300
gaccaatcga tcacaagaag aggacaacca tgttggtaca agtggaaaa cgtcggcgac      360 attgcgatca acgatgcatt catgttggaa ggtgccatct actgtctgtt gaagaaacac     420
ttcagaacag agccatacta cgtcgatcta ttggaattgt tccatgacgt tacttttcaa     480
accgaattgg gtcagttgtt ggatttgatc actgcaccag aggacaaagt cgacttatcc     540
aagttctctt tggaaaagca ttccttcatc gttatcttca agactgcata ctactctttc     600
tacttagcag tggcactggc catgtttgct gccggtatta ccgactcaaa ggacttgaaa     660
caggccagcg acgtattgat cccattggga gaatatttcc aaatccaaga cgatttcttg     720
gattgtttcg gtaaaccaga agatatcggt aagattggta ccgatatcca agacaacaaa     780
tgttcttggg tcatcaacgt tgcattgaag aatgctacaa agaacaaag agatatcttg      840 gacgaaaact acggtagaaa ggattctgaa aaggaacaaa aatgtagagc tgtattcaac     900
gaattgaaca tccaagacat ctaccacaag tacgaagaag aaaccgcttc aacttaaga      960 gagaaaatcg ctaacatcga cgaatcccgt gggttcaagg ccgaagttct aaccttgttc    1020
ttgaacaaaa tataccacag aaagaagtag                                      1050
```

<210> SEQ ID NO 17
<211> LENGTH: 1185
<212> TYPE: DNA
<213> ORGANISM: Artemisia spiciformis

<400> SEQUENCE: 17

```
atggcatcct ttattagtct ttcttccaaa tcggcttctt ggaatgcctc ttcttgtccg       60
cacccatcag ttcaaccttt tgtgactcgg aagaatgtgg tacggtatca taaaccaact     120
tcttctgagc ccagctattc tccgctcact acaacattga gcagcaatct gaactcacaa     180
ttcatgcaag tttacgagac tttgaaatcg gagctaattc acgacccgtt atttgagttt     240
```

| | |
|---|---|
| gatgacgatt ctcgtcagtg ggtggagcgg atgatcgact acactgtacc tggaggaaag | 300 |
| atggtccgag gctattctgt tgttgacagc taccaattgc ttaaaggaga agaattgaca | 360 |
| gaagaagaag cttttctcgc atgtgctctt ggttggtgca ctgaatggtt tcaagcattt | 420 |
| attcttctac atgatgacat gatggatggc tcgcacacac ggagaggtca accctgttgg | 480 |
| ttcagactac ccgaggttgg agcagttgct ataaatgatg gtgttcttct tcgcaaccat | 540 |
| gtccacagaa tcctaaagaa acacttccaa ggaaaggctt attacgtgca tcttgtggac | 600 |
| ctcttcaatg agaccgaatt caaacaatc tctggacaaa tgattgatac gatctctaga | 660 |
| ctagctggac agaaagagct ctcaaagtat tctatgtctc ttaaccgtcg gattgttcag | 720 |
| tacaaaggtg cttactactc atgttacctt ccaattgcgt gtgcactcct tatgtttgga | 780 |
| gagaatctgg atgattatgt tcaagtgaaa gacatccttg tagaattggg tatgtattat | 840 |
| caaattcaga atgattatct cgacactttc ggcgatccta atgttttgg caagactgga | 900 |
| acagatattg aagaatgcaa gtgttcatgg ttgattgcga aagcactgga acttgccaat | 960 |
| gaggaacaaa agaaaatttt aagcgaaaac tatgggataa aagatccagc aaaggtagca | 1020 |
| aaagtgaagg aaatatacca tgctctcaat ctaaagggtg cgtatgaaga ttatgagaca | 1080 |
| aatctgtatg agaattcgat gaaagcaatt aaagctcatc caagcattgc agtgcaagcg | 1140 |
| gtgttgaaat cttgtctgga aaagatgtat aagggacata agtaa | 1185 |

```
<210> SEQ ID NO 18
<211> LENGTH: 1059
<212> TYPE: DNA
<213> ORGANISM: Saccharomyces cerevisiae

<400> SEQUENCE: 18
```

| | |
|---|---|
| atggcttcag aaaagaaat taggagagag agattcttga acgttttccc taaattagta | 60 |
| gaggaattga acgcatcgct tttggcttac ggtatgccta aggaagcatg tgactggtat | 120 |
| gcccactcat tgaactacaa cactccaggc ggtaagctaa atagaggttt gtccgttgtg | 180 |
| gacacgtatg ctattctctc caacaagacc gttgaacaat tggggcaaga agaatacgaa | 240 |
| aaggttgcca ttctaggttg gtgcattgag ttgttgcagg cttacttctt ggtcgccgat | 300 |
| gatatgatgg acaagtccat taccagaaga ggccaaccat gttggtacaa ggttcctgaa | 360 |
| gttgggggaaa ttgccatcaa tgacgcattc atgttagagg ctgctatcta caagcttttg | 420 |
| aaatctcact tcagaaacga aaaatactac atagatatca ccgaattgtt ccatgaggtc | 480 |
| accttccaaa ccgaattggg ccaattgatg gacttaatca ctgcacctga agacaaagtc | 540 |
| gacttgagta agttctccct aaagaagcac tccttcatag ttacttttcaa gactgcttac | 600 |
| tattctttct acttgcctgt cgcattggcc atgtacgttg ccggtatcac ggatgaaaag | 660 |
| gatttgaaac aagccagaga tgtcttgatt ccattgggtg aatacttcca aattcaagat | 720 |
| gactacttag actgcttcgg tacccccagaa cagatcggta agatcggtac agatatccaa | 780 |
| gataacaaat gttcttgggt aatcaacaag gcattggaac ttgcttccgc agaacaaaga | 840 |
| aagactttag acgaaaatta cggtaagaag gactcagtcg cagaagccaa atgcaaaaag | 900 |
| atttcaatg acttgaaaat tgaacagcta taccacgaat atgaagagtc tattgccaag | 960 |
| gatttgaagg ccaaaatttc tcaggtcgat gagtctcgtg gcttcaaagc tgatgtctta | 1020 |
| actgcgttct gaacaaagt ttacaagaga agcaaatag | 1059 |

```
<210> SEQ ID NO 19
<211> LENGTH: 1053
```

```
<212> TYPE: DNA
<213> ORGANISM: Zea mays

<400> SEQUENCE: 19
atggcggcgg gcgggaatgg cgccggcggg gacaccaggg cggccttcgc gcggatctac      60
aagacgctca aggaggagct gctcaccgac ccggccttcg agttcaccga ggagtcacgc     120
cagtggatcg accgcatggt tgactacaat gtactcggag gcaagtgtaa ccgtgggctc     180
tctgtggtcg acagctacaa gctgctcaag gcgctgatgc tctgggcga ggaggaaacg      240 ttccttgctt gcaccctcgg ctggtgcatt gaatggcttc aggctttctt tcttgtgctt     300
gatgatatca tggatgactc tcacactcgt cgcggccagc cttgctggtt cagggtgcct     360
caggttggct taattgctgc gaatgacggg atcatccttc gcaaccatat ctcacggatc     420
cttcggcgcc actttaaggg caaaccttac tatgctgatc ccttgatttt gttcaatgag     480
gttgagttca agacagcttc aggtcagctg ctggacctta tcactaccca tgagggagaa     540
aaagatctaa caaagtataa cataacagtt cacggtcgaa ttgttcaata caagacagcc     600
tattattcat tttatctgcc ggttgcatgt gccctgctgc tctctggcga aatttggac      660 aattatggtg atgtagagaa catccttgtt gaaatgggaa catactttca agtccaggat     720
gactatctgg attgttatgg tgatcctgaa tttatcggca agattggaac ggacattgaa     780
gattacaagt gctcatggct agttgtgcaa gcccttgagc gtgctgatga gagccaaaag     840
cgcattctat ttgaaaatta tggcaagaaa gatccagcct gtgtggcaaa agtgaagaac     900
ctctacaaag aacttgacct agaggcggta tttcaggagt acgagaatga gagctacaag     960
aagctgattg cagacattga agcccagcca agcattgcgg ttcagaaagt gctgaaatcc    1020
ttcttgcaca agatctacaa gaggcagaag tag                                 1053

<210> SEQ ID NO 20
<211> LENGTH: 1032
<212> TYPE: DNA
<213> ORGANISM: Artemisia annua

<400> SEQUENCE: 20
atgagtagca tcgatctgaa atccaagttt ttaaaagtgt atgatacact taaatcagag      60
cttattaacg atcccgcctt cgaattcgac gatgattccc gtcaatggat tgaaaagatg     120
cttgactaca acgtacctgg aggaaagctg aaccggggat tatctgttgt cgacagttat     180
cagcttctta aaggaggaga actgtctgat gacgagattt tcctttcatc tgcccttggt     240
tggtgtattg aatggcttca agcatacttt cttgtgcttg atgatatcat ggacgagtct     300
catacacgca gagggcaacc ctgttggttt agattactca aggttggtat gattgctgcg     360
aacgatggaa ttcttcttcg caaccatgtc ccaagaattc ttaagaaaca tttccgtgga     420
aagccttact atgtggatct tgtggacctg ttcaacgagg ttgaattcca aacagcctct     480
ggtcagatga ttgatttgat cactacactt gttggagaga agatctctc gaagtattca      540 ttgtctattc accgccgaat tgttcaatac aaaacagctt actactcatt ttaccttcca     600
gttgcctgtg cactccttat gtttggagag atcttgaca agcacgttga agtgaagaac      660
atgctcgttg aaatgggtac ctattttcaa gttcaggacg attatctaga ctgttttggt     720
gctcccgagg tgattggaaa gattggaact gatattgaag actttaagtg ctcctggtta     780
gttgtcaagg cattgaaact cgccaatgag gaacaaaaga agtcctaca tgagaactat       840 gggaaaaagg accccgcgtc tgttgctaaa gtgaaggaag tataccacac tctcaatctt     900
```

| | |
|---|---|
| caggctgtat tcgaagatta cgaggccaca agttacaaga agcttatcac atcgattgaa | 960 |
| aatcgcccaa gcaaagcagt ccaagcggtg ctgaaatctt tcttgggtaa aatctacaag | 1020 |
| aggcaaaagt ag | 1032 |

```
<210> SEQ ID NO 21
<211> LENGTH: 1101
<212> TYPE: DNA
<213> ORGANISM: Artificial Sequence
<220> FEATURE:
<223> OTHER INFORMATION: Codon optimized sequence

<400> SEQUENCE: 21
```

| | |
|---|---|
| cacaagttca caggtgttaa cgctaaattc cagcaaccag cattaagaaa tttatctcca | 60 |
| gtggtagttg agcgcgaacg tgaggaattt gtaggattct ttccacaaat tgttcgtgac | 120 |
| ttaactgaag atggtattgg tcatccagaa gtaggtgacg ctgtagctcg tcttaaagaa | 180 |
| gtattacaat acaacgcacc tggtggtaaa tgcaatagag gtttaacagt tgttgcagct | 240 |
| taccgtgaac tttctggacc aggtcaaaaa gacgctgaaa gtcttcgttg tgctttagca | 300 |
| gtaggatggt gtattgaatt attccaagcc ttttttcttag ttgctgacga tataatggac | 360 |
| cagtcattaa ctagacgtgg tcaattatgt tggtacaaga agaaggtgt tggtttagat | 420 |
| gcaataaatg attcttttct tttagaaagc tctgtgtatc gcgttcttaa aaagtattgc | 480 |
| cgtcaacgtc catattatgt acatttatta gagcttttttc ttcaaacagc ttaccaaaca | 540 |
| gaattaggac aaatgttaga tttaatcact gctcctgtat ctaaggtaga tttaagccat | 600 |
| ttctcagaag aacgttacaa agctattgtt aagtataaaa ctgctttcta ttcattctat | 660 |
| ttaccagttg cagcagctat gtatatggtt ggtatagatt ctaaagaaga acatgaaaac | 720 |
| gcaaaagcta ttttacttga gatgggtgaa tacttccaaa ttcaagatga ttatttagat | 780 |
| tgttttggcg atcctgcttt aacaggtaaa gtaggtactg atattcaaga taacaaatgt | 840 |
| tcatggttag ttgtgcaatg cttacaaaga gtaacaccag aacaacgtca acttttagaa | 900 |
| gataattacg gtcgtaaaga accagaaaaa gttgctaaag ttaaagaatt atatgaggct | 960 |
| gtaggtatga gagccgcctt tcaacaatac gaagaaagta gttaccgtcg tcttcaagag | 1020 |
| ttaattgaga acattctaa tcgtttacca aaagaaattt tcttaggttt agctcagaaa | 1080 |
| atatacaaac gtcaaaaagg t | 1101 |

```
<210> SEQ ID NO 22
<211> LENGTH: 1191
<212> TYPE: DNA
<213> ORGANISM: Artificial Sequence
<220> FEATURE:
<223> OTHER INFORMATION: Codon optimized sequence
<220> FEATURE:
<221> NAME/KEY: misc_feature
<222> LOCATION: (4)..(9)
<223> OTHER INFORMATION: Tag
<220> FEATURE:
<221> NAME/KEY: misc_feature
<222> LOCATION: (1111)..(1191)
<223> OTHER INFORMATION: Tag

<400> SEQUENCE: 22
```

| | |
|---|---|
| atggtaccac acaagttcac aggtgttaac gctaaattcc agcaaccagc attaagaaat | 60 |
| ttatctccag tggtagttga gcgcgaacgt gaggaatttg taggattctt tccacaaatt | 120 |
| gttcgtgact taactgaaga tggtattggt catccagaag taggtgacgc tgtagctcgt | 180 |
| cttaaagaag tattacaata caacgcacct ggtggtaaat gcaatagagg tttaacagtt | 240 |

-continued

```
gttgcagctt accgtgaact ttctggacca ggtcaaaaag acgctgaaag tcttcgttgt    300
gctttagcag taggatggtg tattgaatta ttccaagcct tttcttagt tgctgacgat     360 ataatggacc agtcattaac tagacgtggt caattatgtt ggtacaagaa agaaggtgtt    420
ggtttagatg caataaatga ttcttttctt ttagaaagct ctgtgtatcg cgttcttaaa    480
aagtattgcc gtcaacgtcc atattatgta catttattag agcttttct tcaaacagct     540 taccaaacag aattaggaca aatgttagat ttaatcactg ctcctgtatc taaggtagat    600
ttaagccatt tctcagaaga acgttacaaa gctattgtta agtataaaac tgctttctat    660
tcattctatt taccagttgc agcagctatg tatatggttg gtatagattc taaagaagaa    720
catgaaaacg caaaagctat tttacttgag atgggtgaat acttccaaat tcaagatgat    780
tatttagatt gttttggcga tcctgcttta acaggtaaaa taggtactga tattcaagat    840
aacaaatgtt catggttagt tgtgcaatgc ttacaaagag taacaccaga acaacgtcaa    900
cttttagaag ataattacgg tcgtaaagaa ccagaaaaag ttgctaaagt taagaattaa    960
tatgaggctg taggtatgag agccgccttt caacaatacg aagaaagtag ttaccgtcgt    1020
cttcaagagt taattgagaa acattctaat cgtttaccaa aagaaatttt cttaggttta    1080
gctcagaaaa tatacaaacg tcaaaaaggt accggtgaaa acttatactt tcaaggctca    1140
ggtggcggtg aagtgatta caaagatgat gatgataaag gaaccggtta a              1191
```

<210> SEQ ID NO 23
<211> LENGTH: 396
<212> TYPE: PRT
<213> ORGANISM: Gallus gallus
<220> FEATURE:
<221> NAME/KEY: MISC_FEATURE
<222> LOCATION: (2)..(3)
<223> OTHER INFORMATION: Tag

<400> SEQUENCE: 23

```
Met Val Pro His Lys Phe Thr Gly Val Asn Ala Lys Phe Gln Gln Pro
1               5                   10                  15

Ala Leu Arg Asn Leu Ser Pro Val Val Glu Arg Glu Arg Glu Glu
            20                  25                  30

Phe Val Gly Phe Phe Pro Gln Ile Val Arg Asp Leu Thr Glu Asp Gly
        35                  40                  45

Ile Gly His Pro Glu Val Gly Asp Ala Val Ala Arg Leu Lys Glu Val
    50                  55                  60

Leu Gln Tyr Asn Ala Pro Gly Gly Lys Cys Asn Arg Gly Leu Thr Val
65                  70                  75                  80

Val Ala Ala Tyr Arg Glu Leu Ser Gly Pro Gly Gln Lys Asp Ala Glu
                85                  90                  95

Ser Leu Arg Cys Ala Leu Ala Val Gly Trp Cys Ile Glu Leu Phe Gln
            100                 105                 110

Ala Phe Phe Leu Val Ala Asp Asp Ile Met Asp Gln Ser Leu Thr Arg
        115                 120                 125

Arg Gly Gln Leu Cys Trp Tyr Lys Lys Glu Gly Val Gly Leu Asp Ala
    130                 135                 140

Ile Asn Asp Ser Phe Leu Leu Glu Ser Ser Val Tyr Arg Val Leu Lys
145                 150                 155                 160

Lys Tyr Cys Arg Gln Arg Pro Tyr Tyr Val His Leu Leu Glu Leu Phe
                165                 170                 175

Leu Gln Thr Ala Tyr Gln Thr Glu Leu Gly Gln Met Leu Asp Leu Ile
```

```
                180             185                 190
Thr Ala Pro Val Ser Lys Val Asp Leu Ser His Phe Ser Glu Glu Arg
                195                 200                 205
Tyr Lys Ala Ile Val Lys Tyr Lys Thr Ala Phe Tyr Ser Phe Tyr Leu
                210                 215                 220
Pro Val Ala Ala Ala Met Tyr Met Val Gly Ile Asp Ser Lys Glu Glu
225                 230                 235                 240
His Glu Asn Ala Lys Ala Ile Leu Leu Glu Met Gly Glu Tyr Phe Gln
                    245                 250                 255
Ile Gln Asp Asp Tyr Leu Asp Cys Phe Gly Asp Pro Ala Leu Thr Gly
                260                 265                 270
Lys Val Gly Thr Asp Ile Gln Asp Asn Lys Cys Ser Trp Leu Val Val
                275                 280                 285
Gln Cys Leu Gln Arg Val Thr Pro Glu Gln Arg Gln Leu Leu Glu Asp
                290                 295                 300
Asn Tyr Gly Arg Lys Glu Pro Glu Lys Val Ala Lys Val Lys Glu Leu
305                 310                 315                 320
Tyr Glu Ala Val Gly Met Arg Ala Ala Phe Gln Gln Tyr Glu Glu Ser
                    325                 330                 335
Ser Tyr Arg Arg Leu Gln Glu Leu Ile Glu Lys His Ser Asn Arg Leu
                340                 345                 350
Pro Lys Glu Ile Phe Leu Gly Leu Ala Gln Lys Ile Tyr Lys Arg Gln
                355                 360                 365
Lys Gly Thr Gly Glu Asn Leu Tyr Phe Gln Gly Ser Gly Gly Gly Gly
                370                 375                 380
Ser Asp Tyr Lys Asp Asp Asp Lys Gly Thr Gly
385                 390                 395

<210> SEQ ID NO 24
<211> LENGTH: 46
<212> TYPE: DNA
<213> ORGANISM: Artificial Sequence
<220> FEATURE:
<223> OTHER INFORMATION: Primer

<400> SEQUENCE: 24
ttctattgac ggcctgtcag gcctcatata tactttagat tgattt          46

<210> SEQ ID NO 25
<211> LENGTH: 56
<212> TYPE: DNA
<213> ORGANISM: Artificial sequence
<220> FEATURE:
<223> OTHER INFORMATION: Primer

<400> SEQUENCE: 25
ttgacgcact ggccatggtg gccaaaaata aacaaatagg ggttccgcgc acattt    56

<210> SEQ ID NO 26
<211> LENGTH: 45
<212> TYPE: DNA
<213> ORGANISM: Artificial sequence
<220> FEATURE:
<223> OTHER INFORMATION: Primer

<400> SEQUENCE: 26
aactgaccac ggcctgacag gccggtctga cagttaccaa tgctt         45

<210> SEQ ID NO 27
```

<210> SEQ ID NO 27
<211> LENGTH: 44
<212> TYPE: DNA
<213> ORGANISM: Artificial sequence
<220> FEATURE:
<223> OTHER INFORMATION: Primer

<400> SEQUENCE: 27

```
aacctgtcct ggccaccatg gcctaaatac attcaaatat gtat            44
```

<210> SEQ ID NO 28
<211> LENGTH: 1104
<212> TYPE: DNA
<213> ORGANISM: Artificial Sequence
<220> FEATURE:
<223> OTHER INFORMATION: Codon optimized sequence

<400> SEQUENCE: 28

```
atgcacaagt tcacaggtgt taacgctaaa ttccagcaac cagcattaag aaatttatct      60
ccagtggtag ttgagcgcga acgtgaggaa tttgtaggat tctttccaca aattgttcgt     120
gacttaactg aagatggtat tggtcatcca gaagtaggtg acgctgtagc tcgtcttaaa     180
gaagtattac aatacaacgc acctggtggt aaatgcaata gaggtttaac agttgttgca     240
gcttaccgtg aactttctgg accaggtcaa aagacgctg aaagtcttcg ttgtgcttta      300
gcagtaggat ggtgtattga attattccaa gccttttct tagttgctga cgatataatg      360
gaccagtcat taactagacg tggtcaatta tgttggtaca agaaagaagg tgttggttta     420
gatgcaataa atgattcttt tcttttagaa agctctgtgt atcgcgttct taaaaagtat     480
tgccgtcaac gtccatatta tgtacattta ttagagcttt tcttcaaac agcttaccaa      540
acagaattag acaaatgtt agatttaatc actgctcctg tatctaaggt agatttaagc     600
catttctcag aagaacgtta caaagctatt gttaagtata aaactgcttt ctattcattc    660
tatttaccag ttgcagcagc tatgtatatg gttggtatag attctaaaga agaacatgaa    720
aacgcaaaag ctatttact tgagatgggt gaatacttcc aaaattcaaga tgattattta    780
gattgttttg gcgatcctgc tttaacaggt aaagtaggta ctgatattca agataacaaa    840
tgttcatggt tagttgtgca atgcttacaa agagtaacac cagaacaacg tcaactttta    900
gaagataatt acggtcgtaa agaaccagaa aaagttgcta agttaaaga attatatgag     960
gctgtaggta tgagagccgc ctttcaacaa tacgaagaaa gtagttaccg tcgtcttcaa    1020
gagttaattg agaaacattc taatcgttta ccaaaagaaa ttttcttagg tttagctcag    1080
aaaatataca aacgtcaaaa aggt                                           1104
```

<210> SEQ ID NO 29
<211> LENGTH: 394
<212> TYPE: PRT
<213> ORGANISM: Gallus gallus

<400> SEQUENCE: 29

```
Met His Lys Phe Thr Gly Val Asn Ala Lys Phe Gln Gln Pro Ala Leu
1               5                   10                  15

Arg Asn Leu Ser Pro Val Val Glu Arg Glu Arg Glu Glu Phe Val
            20                  25                  30

Gly Phe Phe Pro Gln Ile Val Arg Asp Leu Thr Glu Asp Gly Ile Gly
        35                  40                  45

His Pro Glu Val Gly Asp Ala Val Ala Arg Leu Lys Glu Val Leu Gln
    50                  55                  60

Tyr Asn Ala Pro Gly Gly Lys Cys Asn Arg Gly Leu Thr Val Val Ala
```

-continued

```
             65                  70                  75                  80
Ala Tyr Arg Glu Leu Ser Gly Pro Gly Gln Lys Asp Ala Glu Ser Leu
                     85                  90                  95

Arg Cys Ala Leu Ala Val Gly Trp Cys Ile Glu Leu Phe Gln Ala Phe
                    100                 105                 110

Phe Leu Val Ala Asp Asp Ile Met Asp Gln Ser Leu Thr Arg Arg Gly
                115                 120                 125

Gln Leu Cys Trp Tyr Lys Lys Glu Gly Val Gly Leu Asp Ala Ile Asn
            130                 135                 140

Asp Ser Phe Leu Leu Glu Ser Ser Val Tyr Arg Val Leu Lys Lys Tyr
145                 150                 155                 160

Cys Arg Gln Arg Pro Tyr Tyr Val His Leu Leu Glu Leu Phe Leu Gln
                165                 170                 175

Thr Ala Tyr Gln Thr Glu Leu Gly Gln Met Leu Asp Leu Ile Thr Ala
                180                 185                 190

Pro Val Ser Lys Val Asp Leu Ser His Phe Ser Glu Glu Arg Tyr Lys
                195                 200                 205

Ala Ile Val Lys Tyr Lys Thr Ala Phe Tyr Ser Phe Tyr Leu Pro Val
            210                 215                 220

Ala Ala Ala Met Tyr Met Val Gly Ile Asp Ser Lys Glu Glu His Glu
225                 230                 235                 240

Asn Ala Lys Ala Ile Leu Leu Glu Met Gly Glu Tyr Phe Gln Ile Gln
                245                 250                 255

Asp Asp Tyr Leu Asp Cys Phe Gly Asp Pro Ala Leu Thr Gly Lys Val
                260                 265                 270

Gly Thr Asp Ile Gln Asp Asn Lys Cys Ser Trp Leu Val Val Gln Cys
        275                 280                 285

Leu Gln Arg Val Thr Pro Glu Gln Arg Gln Leu Leu Glu Asp Asn Tyr
        290                 295                 300

Gly Arg Lys Glu Pro Glu Lys Val Ala Lys Val Lys Glu Leu Tyr Glu
305                 310                 315                 320

Ala Val Gly Met Arg Ala Ala Phe Gln Gln Tyr Glu Glu Ser Ser Tyr
                325                 330                 335

Arg Arg Leu Gln Glu Leu Ile Glu Lys His Ser Asn Arg Leu Pro Lys
            340                 345                 350

Glu Ile Phe Leu Gly Leu Ala Gln Lys Ile Tyr Lys Arg Gln Lys Gly
            355                 360                 365

Thr Gly Glu Asn Leu Tyr Phe Gln Gly Ser Gly Gly Gly Ser Asp
    370                 375                 380

Tyr Lys Asp Asp Asp Asp Lys Gly Thr Gly
385                 390
```